United States Patent
Koh et al.

(10) Patent No.: US 11,680,946 B1
(45) Date of Patent: Jun. 20, 2023

(54) DETECTION OF CHOLINESTERASE INHIBITION WITH MICROFLUIDIC DEVICES AND SYSTEMS THEREOF

(71) Applicant: National Technology & Engineering Solutions of Sandia, LLC, Albuquerque, NM (US)

(72) Inventors: Chung-Yan Koh, Arlington, VA (US); Robert Meagher, Mountain House, CA (US); Tyler Phillips Eckles, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 185 days.

(21) Appl. No.: 17/143,363

(22) Filed: Jan. 7, 2021

Related U.S. Application Data

(60) Provisional application No. 62/961,800, filed on Jan. 16, 2020.

(51) Int. Cl.
*G01N 33/573* (2006.01)
*B01L 3/00* (2006.01)

(52) U.S. Cl.
CPC ...... *G01N 33/573* (2013.01); *B01L 3/502715* (2013.01); *B01L 3/502761* (2013.01); *B01L 2300/069* (2013.01); *B01L 2300/0636* (2013.01); *B01L 2300/0803* (2013.01); *G01N 2333/918* (2013.01)

(58) Field of Classification Search
CPC ............ G01N 33/573; G01N 2333/918; B01L 3/502715; B01L 3/502761; B01L 2300/0636; B01L 2300/069; B01L 2300/0803
See application file for complete search history.

(56) References Cited

U.S. PATENT DOCUMENTS

| | | | |
|---|---|---|---|
| 8,945,914 B1 | 2/2015 | Schaff et al. |
| 8,962,346 B2 | 2/2015 | Schaff et al. |
| 9,186,668 B1 | 11/2015 | Schaff et al. |
| 9,244,065 B1 | 1/2016 | Schaff et al. |
| 9,304,128 B1 | 4/2016 | Koh et al. |
| 9,304,129 B2 | 4/2016 | Schaff et al. |
| 9,500,579 B1 | 11/2016 | Sommer et al. |
| 9,702,871 B1 | 7/2017 | Koh et al. |
| 9,766,230 B1 | 9/2017 | Koh et al. |
| 9,795,961 B1 | 10/2017 | Koh et al. |
| 9,803,238 B1 | 10/2017 | Koh et al. |

(Continued)

OTHER PUBLICATIONS

Dafferner et al "Immunopurification of Acetylcholinesterase from Red Blood Cells for Detection of Nerve Agent Exposure" Chem. Res. Toxicol. 2017, 30, 1897-1910 (Year: 2017).*

(Continued)

*Primary Examiner* — Dennis White
(74) *Attorney, Agent, or Firm* — Madelynne J. Farber; Samantha Updegraff; Weaver Austin Villeneuve & Sampson LLP

(57) ABSTRACT

The present invention relates to methods of conducting cholinesterase inhibition assays. In one instance, the assays can be configured to determine the presence of inactivated and activated cholinesterases. Also described herein are microfluidic devices and systems for conducting such assays.

10 Claims, 25 Drawing Sheets

Specification includes a Sequence Listing.

(56) References Cited

U.S. PATENT DOCUMENTS

| | | | |
|---|---|---|---|
| 9,903,001 | B1 | 2/2018 | Koh et al. |
| 10,024,849 | B2 | 7/2018 | Schaff et al. |
| 10,254,298 | B1 | 4/2019 | Koh |
| 10,384,202 | B2 | 8/2019 | Koh et al. |
| 10,406,528 | B1 | 9/2019 | Phaneuf et al. |
| 10,590,477 | B2 | 3/2020 | Koh et al. |
| 10,724,091 | B1 | 7/2020 | Meagher et al. |
| 10,786,811 | B1 | 9/2020 | Koh et al. |
| 2014/0154816 | A1* | 6/2014 | Schaff .............. B01L 3/502753 422/69 |
| 2015/0360225 | A1 | 12/2015 | Schaff et al. |
| 2016/0377617 | A1* | 12/2016 | Basinger, Jr. .. C12Y 301/01008 435/7.4 |
| 2018/0037960 | A1 | 2/2018 | Koh et al. |
| 2018/0065118 | A1 | 3/2018 | Koh et al. |

OTHER PUBLICATIONS

Ahmadi-Motamayel F et al., "Evaluation of salivary acetylcholinesterase and pseudocholinesterase in patients with Alzheimer's disease: a case-control study," *Special Care Dentistry* 2019;39(1):39-44 [Abstract only, 2 pp.].

Carmany DO et al., "On-substrate enzymatic reaction to determine acetylcholinesterase activity in whole blood by paper spray mass spectrometry," *J. Am. Soc. Mass Spectrom.* 2018;29:2436-42.

Chen G et al., "Thiol-ene click reaction-induced fluorescence enhancement by altering the radiative rate for assaying butyrylcholinesterase activity," *Analyst* 2019;144:559-66 [Abstract only, 5 pp.].

Chowdhary S et al., "A novel fluorescence based assay for the detection of organophosphorus pesticide exposed cholinesterase activity using 1-naphthyl acetate," *Biochimie* 2019;160:100-12 [Abstract only, 1 p.].

Dafferner AJ et al., "Immunopurification of acetylcholinesterase from red blood cells for detection of nerve agent exposure," *Chem. Res. Toxicol.* 2017;30:1897-910.

Diao J et al., "Protein surface structural recognition in inactive areas: a new immobilization strategy for acetylcholinesterase," *Bioconjugate Chem.* 2018;29:1703-13 [Abstract only, 5 pp.].

Du D et al., "Integrated lateral flow test strip with electrochemical sensor for quantification of phosphorylated cholinesterase: biomarker of exposure to organophosphorous agents," *Anal. Chem.* 2012;84:1380-5 [Abstract only, 2 pp.].

Du D et al., "Magnetic electrochemical sensing platform for biomonitoring of exposure to organophosphorus pesticides and nerve agents based on simultaneous measurement of total enzyme amount and enzyme activity," *Anal. Chem.* 2011;83:3770-7 [Abstract only, 2 pp.].

EQM Research, Inc., "Test-mate ChE, cholinesterase test system (Model 400)," Instruction Manual-E, Apr. 2003, 32 pp.

Hadd AG et al., "Microfluidic assays of acetylcholinesterase inhibitors," *Anal. Chem.* 1999;71:5206-12 [Abstract only, 18 pp.].

Haigh JR et al., "Advantages of the WRAIR whole blood cholinesterase assay: comparative analysis to the micro-Ellman, Test-mate ChE™, and Michel (ΔpH) assays," *Chemico-Biol. Interact.* 2008;175:417-20 [Abstract only, 2 pp.].

He C et al., "A ratiometric fluorescence assay for acetylcholinesterase activity and inhibitor screening based on supramolecular assembly induced monomer-excimer emission transition of a perylene probe," *RSC Adv.* 2018;8:12785-90.

Kammer M et al., "Rapid quantification of two chemical nerve agent metabolites in serum," *Biosens. Bioelectron.* 2019;131:119-27.

Knechtges PL, "An evaluation of blood cholinesterase testing methods for military health surveillance," *United States Army Center for Environmental Health Research (USACEHR) Tech. Rep. No. 0801*, May 2008 (50 pp.).

Kostelnik A et al., "Construction of an acetylcholinesterase sensor based on synthesized paramagnetic nanoparticles, a simple tool for neurotoxic compounds assay," *Sensors* 2017;17:676 (12 pp.).

Lee S et al., "Foldable paper-based analytical device for the detection of an acetylcholinesterase inhibitor using an angle-based readout," *Sens. Actuat. B* 2018;273:322-7.

Lin YS et al., "CD-like centrifugal microfluidic device for organophosphorus pesticides (OPP) sensing," 2017 International Conference on Optical MEMS and Nanophotonics (OMN), held on Aug. 13-17, 2017 in Santa Fe, NM (2 pp.).

Liu R et al., "Application of gold-silver nanocluster based fluorescent sensors for determination of acetylcholinesterase activity and its inhibitor," *Mater. Res. Express* 2018;5:065027 (11 pp.) [Abstract only, 3 pp.].

Luo QJ et al., "An on-off-on gold nanocluster-based fluorescent probe for sensitive detection of organophosphorus pesticides," *RSC Adv.* 2017;7:55199-205.

Ma KK et al., "In situ induced metal-enhanced fluorescence: a new strategy for biosensing the total acetylcholinesterase activity in sub-microliter human whole blood," *Biosens. Bioelectron.* 2015;68:648-53 [Abstract only, 2 pp.].

Mertens MD et al., "A novel fluorogenic probe for the investigation of free thiols: application to kinetic measurements of acetylcholinesterase activity," *Toxicol. Lett.* 2016;244:161-6. [Abstract only, 1 p.].

Miao Y et al., "History and new development of assays for cholinesterase activity and inhibition," *Chem. Rev.* 2010;110:5216-34.

Mukhametshina AR et al., "Luminescent silica nanoparticles for sensing acetylcholinesterase-catalyzed hydrolysis of acetylcholine," *Biosens. Bioelectron.* 2016;77:871-8 [Abstract only, 1 p.].

Oliveira GH et al., "Cholinesterase measurements with an automated kit," *Am. J. Indust. Med.* 2002;Supp. 2:49-53 [Abstract only, 1 p.].

Peng H et al., "Comparison of 5 monoclonal antibodies for immunopurification of human butyrylcholinesterase on Dynabeads: $K_D$ values, binding pairs, and amino acid sequences," *Chem. Biol. Interact.* 2015;240:336-45.

Phaneuf CR et al., "Integrated LAMP and immunoassay platform for diarrheal disease detection," *Biosens. Bioelectron.* 2018;120:93-101.

Phaneuf CR et al., "Portable centrifugal microfluidic platform for nucleic acid detection," SAND Report No. SAND2016-7047C, 20th International Conference on Miniaturized Systems for Chemistry and Life Sciences, held on Oct. 9-13, 2016 in Dublin, Ireland, 2 pp.

Rajapakse BN et al., "Evaluation of the Test-mate ChE (cholinesterase) field kit in acute organophosphorous poisoning," *Ann. Emerg. Med.* 2011;58:559-64.

Ren X et al., "A sensitive biosensor for the fluorescence detection of the acetylcholinesterase reaction system based on carbon dots," *Colloids Surf. B* 2015;125:90-5 [Abstract only, 1 p.].

Rosenberry TL et al., "Comparison of the binding of reversible inhibitors to human butyrylcholinesterase and acetylcholinesterase: a crystallographic, kinetic and calorimetric study," *Molecules* 2017;22:2098 (21 pp.).

Schiedel M et al., "Synthesis and biological evaluation of 8-hydroxy-2,7-naphthyridin-2-ium salts as novel inhibitors of acetylcholinesterase (AChE) and butyrylcholinesterase (BChE)," *Med. Chem. Commun.* 2017;8:465-70.

Sorenson K et al., "An inhibitory monoclonal antibody to human acetylcholinesterases," *Biochim. Biophys. Acta* 1987;912:56-62 [Abstract only, 1 p.].

ŠtěpankováŠ et al., "Cholinesterase-based biosensors," *J. Enzyme Inhib. Med. Chem.* 2016;31:180-93.

Taylor PW et al., "Field verification of Test-Mate ChE," *Military Med.* 2003;168:314-9.

Trueblood AB et al., "Feasibility of portable fingerstick cholinesterase testing in adolescents in south Texas," *J. Primary Care Commun. Health* 2019;10:1-6.

Worek F et al., "On-site analysis of acetylcholinesterase and butyrylcholinesterase activity with the ChE check mobile test kit—determination of reference values and their relevance for diagnosis of exposure to organophosphorus compounds," *Toxicol. Lett.* 2016;249:22-8 [Abstract only, 1 p.].

(56) References Cited

OTHER PUBLICATIONS

Zhang RL et al., "Simple and sensitive fluorescence assay for acetylcholinesterase activity detection and inhibitor screening based on glutathione-capped gold nanoclusters," *Sens. Actuat. B* 2017;253:196-202 [Abstract only, 2 pp.].

* cited by examiner

UniProt Entry No. P22303; human AChE (hAChE, SEQ ID NO:2)
```
  1 MRPPQCLLHT PSLASPLLLL LLWLLGGGVG AEGREDAELL VTVRGGRLRG
 51 IRLKTPGGPV SAFLGIPFAE PPMGPRRFLP PEPKQPWSGV VDATTFQSVC
101 YQYVDTLYPG FEGTEMWNPN RELSEDCLYL NVWTPYPRPT SPTPVLVWIY
151 GGGFYSGASS LDVYDGRFLV QAERTVLVSM NYRVGAFGFL ALPGSREAPG
201 NVGLLDQRLA LQWVQENVAA FGGDPTSVTL FGESAGAASV GMHLLSPPSR
251 GLFHRAVLQS GAPNGPWATV GMGEARRRAT QLAHLVGCPP GGTGGNDTEL
301 VACLRTRPAQ VLVNHEWHVL PQESVFRFSF VPVVDGDFLS DTPEALINAG
351 DFHGLQVLVG VVKDEGSYFL VYGAPGFSKD NESLISRAEF LAGVRVGVPQ
401 VSDLAAEAVV LHYTDWLHPE DPARLREALS DVVGDHNVVC PVAQLAGRLA
451 AQGARVYAYV FEHRASTLSW PLWMGVPHGY EIEFIFGIPL DPSRNYTAEE
501 KIFAQRLMRY WANFARTGDP NEPRDPKAPQ WPPYTAGAQQ YVSLDLRPLE
551 VRRGLRAQAC AFWNRFLPKL LSATDTLDEA ERQWKAEFHR WSSYMVHWKN
601 QFDHYSKQDR CSDL
```

FIG. 8A

UniProt Entry No. P06276; human BChE (hBChE, SEQ ID NO:3)
```
  1 MHSKVTIICI RFLFWFLLLC MLIGKSHTED DIIIATKNGK VRGMNLTVFG
 51 GTVTAFLGIP YAQPPLGRLR FKKPQSLTKW SDIWNATKYA NSCCQNIDQS
101 FPGFHGSEMW NPNTDLSEDC LYLNVWIPAP KPKNATVLIW IYGGGFQTGT
151 SSLHVYDGKF LARVERVIVV SMNYRVGALG FLALPGNPEA PGNMGLFDQQ
201 LALQWVQKNI AAFGGNPKSV TLFGESAGAA SVSLHLLSPG SHSLFTRAIL
251 QSGSFNAPWA VTSLYEARNR TLNLAKLTGC SRENETEIIK CLRNKDPQEI
301 LLNEAFVVPY GTPLSVNFGP TVDGDFLTDM PDILLELGQF KKTQILVGVN
351 KDEGTAFLVY GAPGFSKDNN SIITRKEFQE GLKIFFPGVS EFGKESILFH
401 YTDWVDDQRP ENYREALGDV VGDYNFICPA LEFTKKFSEW GNNAFFYYFE
451 HRSSKLPWPE WMGVMHGYEI EFVFGLPLER RDNYTKAEEI LSRSIVKRWA
501 NFAKYGNPNE TQNNSTSWPV FKSTEQKYLT LNTESTRIMT KLRAQQCRFW
551 TSFFPKVLEM TGNIDEAEWE WKAGFHRWNN YMMDWKNQFN DYTSKKESCV
601 GL
```

FIG. 8B

UniProt Entry No. P21836; mouse AChE (mAChE, SEQ ID NO:4)
```
  1 MRPPWYPLHT PSLAFPLLFL LLSLLGGGAR AEGREDPQLL VRVRGGQLRG
 51 IRLKAPGGPV SAFLGIPFAE PPVGSRRFMP PEPKRPWSGV LDATTFQNVC
101 YQYVDTLYPG FEGTEMWNPN RELSEDCLYL NVWTPYPRPA SPTPVLIWIY
151 GGGFYSGAAS LDVYDGRFLA QVEGAVLVSM NYRVGTFGFL ALPGSREAPG
201 NVGLLDQRLA LQWVQENIAA FGGDPMSVTL FGESAGAASV GMHILSLPSR
251 SLFHRAVLQS GTPNGPWATV SAGEARRRAT LLARLVGCPP GGAGGNDTEL
301 IACLRTRPAQ DLVDHEWHVL PQESIFRFSF VPVVDGDFLS DTPEALINTG
351 DFQDLQVLVG VVKDEGSYFL VYGVPGFSKD NESLISRAQF LAGVRIGVPQ
401 ASDLAAEAVV LHYTDWLHPE DPTHLRDAMS AVVGDHNVVC PVAQLAGRLA
451 AQGARVYAYI FEHRASTLTW PLWMGVPHGY EIEFIFGLPL DPSLNYTTEE
501 RIFAQRLMKY WTNFARTGDN DPRDSKSPQ WPPYTTAAQQ YVSLNLKPLE
551 VRRGLRAQTC AFWNRFLPKL LSATDTLDEA ERQWKAEFHR WSSYMVHWKN
601 QFDHYSKQER CSDL
```

FIG. 8C

UniProt Entry No. Q03311; mouse BChE (mBChE, SEQ ID NO:5)
```
  1 MQTQHTKVTQ THFLLWILLL CMPFGKSHTE EDFIITTKTG RVRGLSMPVL
 51 GGTVTAFLGI PYAQPPLGSL RFKKPQPLNK WPDIHNATQY ANSCYQNIDQ
101 AFPGFQGSEM WNPNTNLSED CLYLNVWIPV PKPKNATVMV WIYGGGFQTG
151 TSSLPVYDGK FLARVERVIV VSMNYRVGAL GFLAFPGNPD APGNMGLFDQ
201 QLALQWVQRN IAAFGGNPKS ITIFGESAGA ASVSLHLLCP QSYPLFTRAI
251 LESGSSNAPW AVKHPEEARN RTLTLAKFTG CSKENEMEMI KCLRSKDPQE
301 ILRNERFVLP SDSILSINFG PTVDGDFLTD MPHTLLQLGK VKKAQILVGV
351 NKDEGTAFLV YGAPGFSKDN DSLITRKEFQ EGLNMYFPGV SRLGKEAVLF
401 YYVDWLGEQS PEVYRDALDD VIGDYNIICP ALEFTKKFAE LENNAFFYFF
451 EHRSSKLPWP EWMGVMHGYE IEFVFGLPLG RRVNYTRAEE IFSRSIMKTW
501 ANFAKYGHPN GTQGNSTMWP VFTSTEQKYL TLNTEKSKIY SKLRAPQCQF
551 WRLFFPKVLE MTGDIDETEQ EWKAGFHRWS NYMMDWQNQF NDYTSKKESC
601 TAL
```
FIG. 8D UniProt Entry No. P23795; bovine AChE (bAChE, SEQ ID NO:6)
```
  1 MRPPWCPLHT PSLTPPLLLL LFLIGGGAEA EGPEDPELLV MVRGGRLRGL
 51 RLMAPRGPVS AFLGIPFAEP PVGPRRFLPP EPKRPWPGVL NATAFQSVCY
101 QYVDTLYPGF EGTEMWNPNR ELSEDCLYLN VWTPYPRPSS PTPVLVWIYG
151 GGFYSGASSL DVYDGRFLTQ AEGTVLVSMN YRVGAFGFLA LPGSREAPGN
201 VGLLDQRLAL QWVQENVAAF GGDPTSVTLF GESAGAASVG MHLLSPPSRG
251 LFHRAVLQSG APNGPWATVG VGEARRRATL LARLVGCPPG GAGGNDTELV
301 ACLRARPAQD LVDHEWRVLP QESVFRFSFV PVVDGDFLSD TPEALINAGD
351 FHGLQVLVGV VKDEGSYFLV YGAPGFSKDN ESLISRAQFL AGVRVGVPQA
401 SDLAAEAVVL HYTDWLHPED PARLREALSD VVGDHNVVCP VAQLAGRLAA
451 QGARVYAYIF EHRASTLSWP LWMGVPHGYE IEFIFGLPLE PSLNYTIEER
501 TFAQRLMRYW ANFARTGDPN DPRDPKAPQW PPYTAGAQQY VSLNLRPLEV
551 RRGLRAQACA FWNRFLPKLL SATDTLDEAE RQWKAEFHRW SSYMVHWKNQ
601 FDHYSKQDRC SDL
```
FIG. 8E UniProt Entry No. P32749; bovine BChE (bBChE, SEQ ID NO:7)
```
  1 MQSRSTVIYI RFVLWFLLLW VLFEKSHTEE DIIITTKNGK VRGMHLPVLG
 51 GTVTAFLGIP YAQPPLGRLR FKKPQSLTKW PDIWNATKYA NSCYQNTDQS
101 FPGFLGSEMW NPNTDLSEDC LYLNVWIPTP KPKNATVMIW IYGGSFQTGT
151 SSLHVYDGKF LARVERVIVV SMNYRVGALG FLALPGNPEA PGNVGLFDQQ
201 LALQWVQKNI AAFGGNPKSV TLFGESAGAA SVSLHLLSPE SHPLFTRAIL
251 QSGSSNAPWA VTSRYEARNR TLTLAKFIGC SRENDTEIIK CLRNKDPQEI
301 LRHEVFVVPY GTLLSVNFGP TVDGDFLTDM PDTLLQLGQF KKTQILVGVN
351 KDEGTAFLVY GAPGFSKDNN SIITRKEFQE GLKIFFPGVS EFGKESILFH
401 YMDWLDDQRA EKYREALDDV VGDYNIICPA LEFTKKFSDM GNNAFFYYFE
451 HRSSKLPWPE WMGVMHGYEI EFVFGLPLER RVNYTKAEEI FSRSIMKRWA
501 NFAKYGNPNG TQNNSTRWPV FKSNEQKYFT LNTESPKVNT KLRAQQCRFW
551 TLFFPKVLEI TGNIDEVERE WKAGFHRWNN YMMDWKNQFN DYTSKKESCA
601 GL
```
FIG. 8F

```
UniProt Entry No. P37136; rat AChE (rAChE, SEQ ID NO:8)
    1 MRPPWYPLHT PSLASPLLFL LLSLLGGGAR AEGREDPQLL VRVRGGQLRG
   51 IRLKAPGGPV SAFLGIPFAE PPVGSRRFMP PEPKRPWSGI LDATTFQNVC
  101 YQYVDTLYPG FEGTEMWNPN RELSEDCLYL NVWTPYPRPT SPTPVLIWIY
  151 GGGFYSGASS LDVYDGRFLA QVEGTVLVSM NYRVGTFGFL ALPGSREAPG
  201 NVGLLDQRLA LQWVQENIAA FGGDPMSVTL FGESAGAASV GMHILSLPSR
  251 SLFHRAVLQS GTPNGPWATV SAGEARRRAT LLARLVGCPP GGAGGNDTEL
  301 ISCLRTRPAQ DLVDHEWHVL PQESIFRFSF VPVVDGDFLS DTPDALINTG
  351 DFQDLQVLVG VVKDEGSYFL VYGVPGFSKD NESLISRAQF LAGVRIGVPQ
  401 ASDLAAEAVV LHYTDWLHPE DPAHLRDAMS AVVGDHNVVC PVAQLAGRLA
  451 AQGARVYAYI FEHRASTLTW PLWMGVPHGY EIEFIFGLPL DPSLNYTVEE
  501 RIFAQRLMQY WTNFARTGDP NDPRDSKSPR WPPYTTAAQQ YVSLNLKPLE
  551 VRRGLRAQTC AFWNRFLPKL LSATDTLDEA ERQWKAEFHR WSSYMVHWKN
  601 QFDHYSKQER CSDL
```

FIG. 8G

```
CONS1                                            EXXXXXXXXXXXXXGXXRGXXXXXXXG  27
CONS2                                            EXXXXXXXXXXXXXGXXRGXXXXXXXG  27
hAChE  MRPPQCLLH--PSLASP L-L   LWLLGGGVGA GREDA L  TV GG R RGIRLKTPG   58
hBChE  MHSK----VT-IICIRF FWF   LCMLIGKSHT ----D I  AT N K RGMNLTVFG    51
mAChE  MRPPWYPLH--PSLAFP LFL  -SLLGGGARA GREDP L  RV GG Q RGIRLKAPG    58
mBChE  MQTQ----H-KVTQTHF LWI   LCMPFGKSHT ----E F  TT T GR RGLSMPVLG    52
bAChE  MRPPWCPLH--PSLTPP L-L  -FLIGGGAEA GPEDP L  MV GG P RGLRLMAPR    57
bBChE  MQSR----S -VIYIRF LWF   LWVLFEKSHT ----E I  TT N K RGMHLPVLG    51
rAChE  MRPPWYPLH--PSLASP LFL  -SLLGGGARA GREDP L  RV GG Q RGIRLKAPG    58

CONS1  XVXAFLGIPXAXPPXGXXRFXXPXXXXXWXXXXXATXXXXXCXQXXDXXXPGFXGXEMWN  87
CONS2  XVXAFLGIPXAXPPXGXXRFXXPXXXXXWXXXXXATXXXXXCXQXXDXXXPGFXGXEMWN  87
hAChE  PV AFLGIP A PE GPR  LP  PKQ WSG V ATT QSV Y YVDTL PG EG EMWN  118
hBChE  TV AFLGIP A PL GRL EKK  SLTK SD W ATK ANS C NID QS PG HG EMWN  111
mAChE  PV AFLGIP A PV GSR MPP PKRP WSG L ATT QNV Y YVDTL PG EG EMWN  118
mBChE  TV AFLGIP A PL GSL EKK  PLNK PD H ATQ ANS Y NID QA PG FQ EMWN  112
bAChE  PV AFLGIP A PV GPR LP  PKRE PG L ATA QSV Y YVDTL PG EG EMWN  117
bBChE  TV AFLGIP A PL GRL EKK  SLTK PD W ATK ANS Y NT QS PG LG EMWN  111
rAChE  PV AFLGIP A PV GSR MPE PKRP WSG L ATT QNV Y YVDTL PG EG EMWN  118

CONS1  PNXXLSEDCLYLNVWXPXPXPXXXTXVXXWIYGGXFXXGXXSLXVYDGXFLXXXEXXXXV 147
CONS2  PNXXLSEDCLYLNVWXPXPXPXXXTXVXXWIYGGXFXXGXXSLXVYDGXFLXXXEXXXXV 147
hAChE  PNR LSEDCLYLNVW PY  PTSP PVL  WIYGGG Y  ASS LDVYDG FLVQ ERT  V 178
hBChE  PNT LSEDCLYLNVW IPA  PKNA -VL WIYGGF Q  TS  LHVYDG FLAR ERV  V 170
mAChE  PNR LSEDCLYLNVW TP  ASP PVL  WIYGGG Y  AAS LDVYDG FLAQ EGA  V 178
mBChE  PNT LSEDCLYLNVW IP   PKNA -VM WIYGGF Q  TS  LPVYDG FLAR ERV  V 171
bAChE  PNR LSEDCLYLNVW P   SSP PVL  WIYGGG Y  AS  LDVYDG FLTQ EGT  V 177
bBChE  PNT LSEDCLYLNVW IPT  PKNA -VM WIYGGF Q  TS  LHVYDG FLAR ERV  V 170
rAChE  PNR LSEDCLYLNVW TP  PTSP PVL  WIYGGG Y  ASS LDVYDG FLAQ EGT  V 178
```

FIG. 9A

```
CONS1   SMNYRVGXXGFLAXPGXXXAPGNXGLXDQXLALQWVQXNXAAFGGXPXSXTXFGESAGAA  207
CONS2   SMNYRVGXXGFLAXPGXXXAPGNXGLXDQXLALQWVQXNXAAFGGXPXSXTXFGESAGAA  207
hAChE   SMNYRVGAFGFLALPGSRTAPGNVGLLDQRLALQWVQEN AAFGG PTS T FGESAGAA  238
hBChE   SMNYRVGALGFLALPGNPTAPGNMGLFDQQLALQWVQKN AAFGG PKS T FGESAGAA  230
mAChE   SMNYRVGTFGFLALPGSRTAPGNVGLLDQRLALQWVQEN AAFGG PMS T FGESAGAA  238
mBChE   SMNYRVGALGFLAFPGNPTAPGNMGLFDQQLALQWVQRN AAFGG PKS T FGESAGAA  231
bAChE   SMNYRVGAFGFLALPGSRTAPGNVGLLDQRLALQWVQEN AAFGG PTS T FGESAGAA  237
bBChE   SMNYRVGALGFLALPGNPTAPGNVGLFDQQLALQWVQKN AAFGG PKS T FGESAGAA  230
rAChE   SMNYRVGTFGFLALPGSRTAPGNVGLLDQRLALQWVQEN AAFGG PMS T FGESAGAA  238

CONS1   SVXXHXLXXXSXXLFXRAXLXSGXXNXPWAXXXXXEARXRXXXLAXXXGCXXXXXXXNXX  267
CONS2   SVXXHXLXXXSXXLFXRAXLXSGXXNXPWAXXXXXEARXRXXXLAXXXGCXXXXXXXNXX  267
hAChE   SVGMHLLSPPSRGLFHRAVLQSGAPN PWATVGMGEARRRATQLAHLVGCPPGGTGGN T  298
hBChE   SVSLHLLSPGSHSLFTRAILQSGSFN APWAVTSLYEAPNRTLN ALTGC----SREN T  286
mAChE   SVGMHLLSLPSRSLFHRAVLQSGTPN PWATVSAGEARRRATLLARLVGCPPGGAGGN T  298
mBChE   SVSLHLCPQSYPLLTRAILQSGSSN PWAVKHPEEARN PTLTLAFTGC----SKEN M  287
bAChE   SVGMHLLSPPSRGLFHRAVLQSGAPN PWATVGVGEARRRATLLARLVGCPPGGAGGN T  297
bBChE   SVSLHLLSPESHPLLTRAILQSGSSN PWAVTSRYEAPNRTLTLAFIGC----SREN T  286
rAChE   SVGMHLLSLPSRSLFHRAVLQSGTPN PWATVSAGEARRRATLLARLVGCPPGGAGGN T  298

CONS1   EXXXCLRXXXXQXXXXXEXXVXPXXXXXXXXXFXPXVDGDFLXDXPXXLXXXGXXXXXQXL  327
CONS2   EXXXCLRXXXXQXXXXXEXXVXPXXXXXXXXXFXPXVDGDFLXDXPXXLXXXGXXXXXQXL  327
hAChE   ELAACLRTTPAQVLVNHEWHVLPQESVFRFSFVPVVDGDFLLDTPEAL INAGDFHGLQVL  358
hBChE   EIKCLRNTDPQEILLNEAFVVPYGTPLSVNFGPTVDGDFLLDMPDIL LGQFKKTQIL  346
mAChE   ELAACLRTRPAQDLVDHEWHVLPQESIFRFSFVPVVDGDFLLDTPEAL INTGDFQDLQVL  358
mBChE   EMKCLRSRDPQELRNERFLLSDTILSINFGPTVDGDFLLDMPHTL LGKVKKAQIL  347
bAChE   ELACLRARPAQDLVDHEWRVLPQESVFRFSFVPVVDGDFLLDTPEAL INAGDFHGLQVL  357
bBChE   EIKCLRNTDPQEIRHEVFVVPYGLLSVNFGPTVDGDFLLDMPDTL LGQFKKTQIL  346
rAChE   ELSCLRTKPAQDLVDHEWHVLPQESIFRFSFVPVVDGDFLLDTPDAL ITGDFQDLQVL  358

CONS1   VGVXKDEGXXFLVYGXPGFSKDNXSXIXRXXFXXGXXXXXPXXSXXXXEXXXXXYXDWXX  387
CONS2   VGVXKDEGXXFLVYGXPGFSKDNXSXIXRXXFXXGXXXXXPXXSXXXXEXXXXXYXDWXX  387
hAChE   VGVVKDEGSYFLVYGAPGFSKDNESLISRAEFLAGVRVGVPQVSDLAAEAVLHYTDWLH  418
hBChE   VGVNKDEGTAFLVYGAPGFSKDNNSLISKFQEGKIFFPGVSEFHKESTFHYTDW D  406
mAChE   VGVVKDEGSYELVYGAPGFSKDNNSLISRAEFLAGRIGVPQVSDLAAEAVLHYTDWLH  418
mBChE   VGVNKDEGAFLVYGAPGFSKDNNSLISRKFQEGNMYFPGVSRLKEAFYYVDWTG  407
bAChE   VGVVKDEGSYFLVYGAPGFSKDNESLISRAEFLAGVRVGVPQVSDLAAEAVLHYTDW H  417
bBChE   VGVNKDEGAFLVYGAPGFSKDNNSLISRFQEGKIFFPGVSEFKESTFHYMDW D  406
rAChE   VGVVKDEGSYELVYGAPGFSKDNNSLISRAEFLAGRIGVPQVSDLAAEAVLHYTDW H  418

CONS1   XXXXXXXRXAXXXXVXGDXNXXCPXXXXXXXXXXXXXXXXXXXXYXFEHRXSXLXWPXWMGVXH  447
CONS2   XXXXXXXRXAXXXXVXGDXNXXCPXXXXXXXXXXXXXXXXXXXXYXFEHRXSXLXWPXWMGVXH  447
hAChE   PLDPARLRTALSDVVGDHNVICPLLAGLAAQGARVAYVFEHRASTLSWPLWMGVPH  478
hBChE   DERPENYRTALGDVVGDYNFICPVTFTKGFSEWGNNVFYYPEHRSSKLPWPEWMGVMH  466
mAChE   PLDPTHLRAMSAVVGDHNVICPLLAGLAAQGARVANIFEHRASTLTWPLWMGVPH  478
mBChE   EESPEVYRALDDVGDYLICPVTFTKGFAELENNVCYFPEHRSSKLPWPEWMGVMH  467
bAChE   PLDPARLRAALSDVVGDHNVICPVLAGLAAQGARVAYIFEHRASTLSWPLWMGVPH  477
bBChE   DERAEKYRTALDDVGDYIICPVTFTKGFSDMGNNVFYYPEHRSSKLPWPEWMGVMH  466
rAChE   PLDPAHLRAMSAVVGDHNVICPVLAGLAAQGARVAYIFEHRASTLTWPLWMGVPH  478
```

FIG. 9B

```
CONS1  GYEIEFXFGXPLXXXXKNYTXXEXXXXXXXXXXXWKNFAXXGKPNXXXXXXXXXXWPXXXXXX  507
CONS2  GYEIEFXFGXPLXXXXKNYTXXEXXXXXXXXXXXWKNFAXXGKPNXXXXXXXXXXWPXXXXXX  507
hAChE  GYEIEFVFGIPLDPSRNYTAEEKIFAQRMRYWANFARTGDPNEPRDPKAPQWPPTAGA      538
hBChe  GYEIEFVFGLPLERRDNYTKAEEILSRSVKRWANFAKYGNPNETQN-NSTSWPVKSTE      525
mAChE  GYEIEFVFGIPLDPSLNYTTEERIFAQRMKYWTNFARTGDPNDPRDSKSPQWPPTTAA      538
mBChE  GYEIEFVFGLPLGRRVNYTRAEEIFSRSMKTWANFAKYGHPNGTQG--NSTMWPVTSTE     526
bAChE  GYEIEFVFGLPLEPSLNYTIEERTFAQRMRYWANFARTGDPNDPRDPKAPQWPPTAGA      537
bBChE  GYEIEFVFGLPLERRVNYTKAEEIFSRSMKRWANFAKYGNPNGTQN-NSTRWPVKSNE      525
rAChE  GYEIEFVFGIPLDPSLNYTVEERIFAQRMQYWTNFARTGDPNDPRDSKSPRWPPTTAA      538

CONS1  QXYXXLXXXXXXXXXXLRAXXCXFWXXFXPKXLXXTXXXDEXEXXWKAXFHRWXXYMXXW    567
CONS2  QXYXXLXXXXXXXXXXLRAXXCXFWXXFXPKXLXXTXXXDEXEX                    551
hAChE  QQYVTLRPLEQRRGLRAQACAFWNRFLPKLLSATDTLDEAERQWKAEFHRWSSYMVHW    598
hBChe  QKYLTLTESTRIMTKLRAQQCRFWTSFFPKVLEMTGNIDEAEWEWKAGFHRWNNYMMDW    585
mAChE  QQYVTLKPLEQRRGLRAQTCAFWNRFLPKLLSAIDTLDEAERQWKAEFHRWSSYMVHW    598
mBChE  QKILTLTEKSKVYSKLRAPQCQWRLEFPKLLEMTGDIDETEQKWKAGFHRWSNYMMDW    586
bAChE  QQYVTLRPLEQRRGLRAQACAFWNRFLPKLLSATDTLDEAERQWKAEFHRWSSYMVHW    597
bBChE  QKYFTLTESPKINTKLRAQQCRFWTLFPKLLEITGNIDEVERKWKAGFHRWNNYMMDW    585
rAChE  QQYVTLKPLERRGLRAQTCAFWNRFLPKLLSATDTLDEAERQWKAEFHRWSSYMVHW    598

CONS1  XNQFXDXXSKXXXCXXL  584   (SEQ ID NO:10)
CONS2                           (SEQ ID NO:11)
hAChE  KNQF-DHYSKQDRCSDL  614   (SEQ ID NO:2)
hBChe  KNQFNDYTSKKESCVGL  602   (SEQ ID NO:3)
mAChE  KNQF-DHYSKQDRCSDL  614   (SEQ ID NO:4)
mBChE  QNQFNDYTSKKESCTAL  603   (SEQ ID NO:5)
bAChE  KNQF-DHYSKQDRCSDL  613   (SEQ ID NO:6)
bBChE  KNQFNDYTSKKESCAGL  602   (SEQ ID NO:7)
rAChE  KNQF-DHYSKQDRCSDL  614   (SEQ ID NO:8)
```

FIG. 9C

```
GenBank: ARX71332.1; anti-ChE monoclonal antibody 1G, HC (SEQ ID NO:20)
    1 DVQLVESGGG LVQPGGSRKL SCAASGFTFS SFGMHWVRQA PEKGLEWVAY
   51 ISSGSDTIYY ADTVKGRFTI SRDNPKNTLF LQMTSLRSED TAMYFCARPL
  101 YGSSPGWFAY WGQGTLVTVS AAKTTPPSVY PLAPGSAAQT NSMVTLGCLV
  151 KGYFPEPVTV TWNSGSLSSG VHTFPAVLQS DLYTLSSSVT VPSSTWPSET
  201 VTCNVAHPAS STKVDKKIVP RDCGCKPCIC TVPEVSSVFI FPPKPKDVLT
  251 ITLTPKVTCV VVDISKDDPE VQFSWFVDDV EVHTAQTQPR EEQFNSTFRS
  301 VSELPIMHQD WLNGKEFKCR VNSAAFPAPI EKTISKTKGR PKAPQVYTIP
  351 PPKEQMAKDK VSLTCMITDF FPEDITVEWQ WNGQPAENYK NTQPIMDTDG
  401 SYFVYSKLNV QKSNWEAGNT FTCSVLHEGL HNHHTEKSLS HSPGK
```

FIG. 10A

```
GenBank: ARX71334.1; anti-ChE monoclonal antibody 6A, HC (SEQ ID NO:21)
    1 DVQLVESGGG LVQPGGSRKL SCAASGFTFS SFGMHWVRQA PEKGLEWVAY
   51 ISSGSDTIYY ADTVKGRFTI SRDNPKNTLF LQMTSLRSED TAMYYCARPL
  101 YGSSPGWFAY WGQGTLVTVT AAKTTPPSVY PLAPGSAAQT NSMVTLGCLV
  151 KGYFPEPVTV TWNSGSLSSG VHTFPAVLQS DLYTLSSSVT VPSSTWPSET
  201 VTCNVAHPAS STKVDKKIVP RDCGCKPCIC TVPEVSSVFI FPPKPKDVLT
  251 ITLTPKVTCV VVDISKDDPE VQFSWFVDDV EVHTAQTQPR EEQFNSTFRS
  301 VSELPIMHQD WLNGKEFKCR VNSAAFPAPI EKTISKTKGR PKAPQVYTIP
  351 PPKEQMAKDK VSLTCMITDF FPEDITVEWQ WNGQPAENYK NTQPIMDTDG
  401 SYFVYSKLNV QKSNWEAGNT FTCSVLHEGL HNHHTEKSLS HSPGK
```

FIG. 10B

```
GenBank: ARX71330.1; anti-ChE monoclonal antibody 10D, HC (SEQ ID NO:22)
    1 EVQLQQSGPE LVKTGASVKI SCKASYSSFT SYYIHWVKQS HGKSLEWIGY
   51 ISCYNGATTY NQKFKGKATF TVDTSSNTAY MQFNSLTSED SAVYYCARWF
  101 GSTGAMDYWG QGTSVTVSSA KTTPPSVYPL APGSAAQTNS MVTLGCLVKG
  151 YFPEPVTVTW NSGSLSSGVH TFPAVLQSDL YTLSSSVTVP SSTWPSETVT
  201 CNVAHPASST KVDKKIVPRD CGCKPCICTV PEVSSVFIFP PKPKDVLTIT
  251 LTPKVTCVVV DISKDDPEVQ FSWFVDDVEV HTAQTQPREE QFNSTFRSVS
  301 ELPIMHQDWL NGKEFKCRVN SAAFPAPIEK TISKTKGRPK APQVYTIPPP
  351 KEQMAKDKVS LTCMITDFFP EDITVEWQWN GQPAENYKNT QPIMDTDGSY
  401 FVYSKLNVQK SNWEAGNTFT CSVLHEGLHN HHTEKSLSHS PGK
```

FIG. 10C

```
GenBank: ARX71336.1; anti-ChE monoclonal antibody AE1, HC (SEQ ID NO:23)
    1 EVQLQQSGPE VVKTGASVKI SCKASGYSFT GYYIHWVKQS HGKSLEWIGY
   51 ISCYNGAASY NQRFKGKATF TVDTSSSTAY MQFNSLTSED SAVYYCARFE
  101 SMTTGAMDYW GQGTSVTVSS AKTTPPSVYP LAPGSAAQTN SMVTLGCLVK
  151 GYFPEPVTVT WNSGSLSSGV HTFPAVLQSD LYTLSSSVTV PSSTWPSETV
  201 TCNVAHPASS TKVDKKIVPR DCGCKPCICT VPEVSSVFIF PPKPKDVLTI
  251 TLTPKVTCVV VDISKDDPEV QFSWFVDDVE VHTAQTQPRE EQFNSTFRSV
  301 SELPIMHQDW LNGKEFKCRV NSAAFPAPIE KTISKTKGRP KAPQVYTIPP
  351 PKEQMAKDKV SLTCMITDFF PEDITVEWQW NGQPAENYKN TQPIMDTDGS
  401 YFVYSKLNVQ KSNWEAGNTF TCSVLHEGLH NHHTEKSLSH SPGK
```

FIG. 10D

GenBank: ARX71338.1; anti-ChE monoclonal antibody AE2, HC (SEQ ID NO:24)
```
  1 DVKVVESGGG LVKPGGSLKL SCAASGFTFS RFTMSWVRQT PEKRLEWVAT
 51 ISSGGSYIYY ADSVKGRFTI SRDNAKNTLY LQMNSLKSED TGMYYCTRDA
101 HFDYWGQGTT LTVSSAKTTP PSVYPLAPGS AAQTNSMVTL GCLVKGYFPE
151 PVTVTWNSGS LSSGVHTFPA VLQSDLYTLS SSVTVPSSTW PSETVTCNVA
201 HPASSTKVDK KIVPRDCGCK PCICTVPEVS SVFIFPPKPK DVLTITLTPK
251 VTCVVVDISK DDPEVQFSWF VDDVEVHTAQ TQPREEQFNS TFRSVSELPI
301 MHQDWLNGKE FKCRVNSAAF PAPIEKTISK TKGRPKAPQV YTIPPPKEQM
351 AKDKVSLTCM ITDFFPEDIT VEWQWNGQPA ENYKNTQPIM DTDGSYFVYS
401 KLNVQKSNWE AGNTFTCSVL HEGLHNHHTE KSLSHSPGK
```
FIG. 10E

GenBank: AHN49951.1; anti-ChE monoclonal antibody mAb2, HC (SEQ ID NO:25)
```
  1 QVQLQQSGAE LVRPGSSVKI SCKASGYAFS SYWMNWVKQR PGQGLEWIGQ
 51 IYPGDSDTNY NGKFKGKATL TADKSSSTAY MQLSSLTSED SAVYFCARDY
101 GKDHFDYWGQ GTTLTVSSAK TTPPSVYPLA PGSAAQTNSM VTLGCLVKGY
151 FPEPVTVTWN SGSLSSGVHT FPAVLQSDLY TLSSSVTVPS SPRPSETVTC
201 NVAHPASSTK VDKKIVPRDC GCKPCICTVP EVSSVFIFPP KPKDVLTITL
251 TPKVTCVVVD ISKDDPEVQF SWFVDDVEVH TAQTQPREEQ FNSTFRSVSE
301 LPIMHQDWLN GKEFKCRVNS AAFPAPIEKT ISKTKGRPKA PQVYTIPPPK
351 EQMAKDKVSL TCMITDFFPE DITVEWQWNG QPAENYKNTQ PIMNTNGSYF
401 VYSKLNVQKS NWEAGNTFTC SVLHEGLHNH HTEKSLSHSP GK
```
FIG. 10F

GenBank: ALD84361.1; anti-ChE monoclonal antibody B2_18-5, HC (SEQ ID NO:26)
```
  1 QVQLQQSGAE LVRPGSSVKI SCKASGYAFS DYWMNWVKQR PGQGLEWIGQ
 51 IYPGDGDTYY NGKFKGKATL TADKSSSTAY MQLSSLISED SAVYFCARSR
101 PLLDYSMHYW GQGASVTVSS AKTTPPSVYP LAPGSAAQTN SMVTLGCLVK
151 GYFPEPVTVT WNSGSLSSGV HTFPAVLQSD LYTLSSSVTV PSSPRPSETV
201 TCNVAHPASS TKVDKKIVPR DCGCKPCICT VPEVSSVFIF PPKPKDVLTI
251 TLTPKVTCVV VDISKDDPEV QFSWFVDDVE VHTAQTQPRE EQFNSTFRSV
301 SELPIMHQDW LNGKEFKCRV NSAAFPAPIE KTISKTKGRP KAPQVYTIPP
351 PKEQMAKDKV SLTCMITDFF PEDITVEWQW NGQPAENYKN TQPIMNTNGS
401 YFVYSKLNVQ KSNWEAGNTF TCSVLHEGLH NHHTEKSLSH SPGK
```
FIG. 10G

GenBank: ALD84363.1; anti-ChE monoclonal antibody B2_12-1, HC (SEQ ID NO:27)
```
  1 EVQLQQSGPE LVKPGASVKI SCKASGYTFT DYSMHWVKLS HGKSLEWIGY
 51 IYPYNDDTDY NQKFKTKATL TVDSSSSITY LELRSLTSED SAVYYCARSD
101 GYSYYFDYWG QGTTLTVSSA KTTPPSVYPL APGSAAQTNS MVTLGCLVKG
151 YFPEPVTVTW NSGSLSSGVH TFPAVLQSDL YTLSSSVTVP SSPRPSETVT
201 CNVAHPASST KVDKKIVPRD CGCKPCICTV PEVSSVFIFP PKPKDVLTIT
251 LTPKVTCVVV DISKDDPEVQ FSWFVDDVEV HTAQTQPREE QFNSTFRSVS
301 ELPIMHQDWL NGKEFKCRVN SAAFPAPIEK TISKTKGRPK APQVYTIPPP
351 KEQMAKDKVS LTCMITDFFP EDITVEWQWN GQPAENYKNT QPIMNTNGSY
401 FVYSKLNVQK SNWEAGNTFT CSVLHEGLHN HHTEKSLSHS PGK
```
FIG. 10H

```
GenBank: ALD84365.1; anti-ChE monoclonal antibody 11D8, HC (SEQ ID NO:28)
    1 MECNWILPFI LSVTSGVYSQ VQLQQSGAEL ARPGASVKLS CKASGYTFTS
   51 QWLQWVKQRP GQGLEWIGAI YPGDGDTRYT QKFKGKATLT ADKSSSTAYM
  101 QLTNLAPEDS AVYYCARSSM DYWGQGTSVT VSSAKTTPPS VYPLAPGSAA
  151 QTNSMVTLGC LVKGYFPEPV TVTWNSGSLS SGVHTFPAVL QSDLYTLSSS
  201 VTVPSSTWPS ETVTCNVAHP ASSTKVDKKI VPRDCGCKPC ICTVPEVSSV
  251 FIFPPKPKDV LTITLTPKVT CVVVDISKDD PEVQFSWFVD DVEVHTAQTQ
  301 PREEQFNSTF RSVSELPIMH QDWLNGKEFK CRVNSAAFPA PIEKTISKTK
  351 GRPKAPQVYT IPPPKEQMAK DKVSLTCMIT DFFPEDITVE WQWNGQPAEN
  401 YKNTQPIMDT DGSYFVYSKL NVQKSNWEAG NTFTCSVLHE GLHNHHTEKS
  451 LSHSPGK
```

FIG. 10I

```
Heavy chain variable regions
CONS1                         XVXXXXSGXXXXXXGXSXKXSCXASXXXFXXXXXXWVXXXX
CONS2                                           XXXFXXXX  (SEQ ID NO:30)
1G       ------------------------VQ V SGGG QPGGSR  CAAS GFT SFGMH  QAP  41
6A       ------------------------VQ V SGGG QPGGSR  CAAS GFT SFGMH  QAP  41
10D      ------------------------VQ Q SGPE KTGASV  CKAS YSS SYYIH  QSH  41
AE1      ------------------------VQ Q SGPE KTGASV  CKAS GYS GYYIH  QSH  41
AE2      ------------------------MK V SGGG KPGGSL  CAAS GFT RFTMS  QTP  41
mAb2     ------------------------VQ Q SGAE RPGSSV  CKAS GYA SYWMN  QRP  41
B2_18-5  ------------------------VQ Q SGAE RPGSSV  CKAS GYA DYWMN  QRP  41
B2_12-1  ------------------------VQ Q SGPE KPGASV  CKAS GYT DYSMH  LSH  41
11D8     MECNWILPFILSVTSGVYS     VQ Q SGAE RPGASV  CKAS GYT SQWLQ  QRP  60
                                                       CDR1

CONS1    XXXLEWXXXIXXXXXXXXYXXXXKXXXTXXDXXXXXXXXXXXXLXXEDXXXYXCXRXXX
CONS3/4        IXXXXXXX  (SEQ ID NO:31)                    XRXXX
1G       EKG EW  Y SSGSDT YADTV G F I RNPKNTL L MTS RS    MY  ARPLY 101
6A       EKG EW  Y SSGSDT YADTV G F I RNPKNTL L MTS RS    MY  ARPLY 101
10D      GKS EW  Y SCYNGAT YNQKF G A F VDTSSNTA M FNS TS    V  APWF- 100
AE1      GKS EW  Y SCYNGAA SNQRF G A F VDTSSSTA M FNS TS    V  ARFE- 100
AE2      EKR EW  T SSGGSYI YADSV G F I RDNAKNTL L MNS KS    MY  TRDA- 100
mAb2     GQG EW   YPGDSDT NYNGKF G A L ADKSSSTA M LSS TS    V  ARDY- 100
B2_18-5  GQG EW   YPGDGDT YNGKF G A L ADKSSSTA M LSS ISL   VT  ARSR- 100
B2_12-1  GKS EW   YPYNDDT YNQKF T A L VDSSSSIT L LRS TS    V  ARSD- 100
11D8     GQG EW  A YPGDGDT RYTQKF G A L ADKSSSTA M LTN APED V  AKS-- 118
                 CDR2                                         CDR3

CONS1    XXXXXXXXYWGQGXXXTVXX        (SEQ ID NO:29)
CONS4    XXXXXXXXY                   (SEQ ID NO:32)
1G       GSSPGWFA WGQGTL TV A  121   (SEQ ID NO:20)
6A       GSSPGWFA WGQGTL TV A  121   (SEQ ID NO:21)
10D      -GSTGAMD WGQGTS TV S  119   (SEQ ID NO:22)
AE1      SMTTGAMD WGQGTS TV S  120   (SEQ ID NO:23)
AE2      ------HFD WGQGTT TV S  115  (SEQ ID NO:24)
mAb2     -GKD-HFD WGQGTT TV S  118   (SEQ ID NO:25)
B2_18-5  PLLDYSMH WGQGAS TV S  120   (SEQ ID NO:26)
B2_12-1  GYSY-YFD WGQGTT TV S  119   (SEQ ID NO:27)
11D8     -----SMD WGQGTS TV S  133   (SEQ ID NO:28)
         CDR3
```

FIG. 11A

```
CONS5   XVXXXXSGXXXVXXGXSXKXSCXASXXXFXXXXXXWVKQXXXKXLEWXXX
1G      VQLVESGGGLVQPGGSRKLSCAASGFTFSSGMHWVRQAPEKGLEWVAY  50
6A      VQLVESGGGLVQPGGSRKLSCAASGFTFSSGMHWVRQAPEKGLEWVAY  50
10D     VQLQQSGPELVKTGSVKLSCKASYSFTSYIHWVKQSHGKSLEWIGY    50
AE1     VQLQQSGPELVKTGSVKLSCKASGYTFGYIHWVKQSHGKSLEWIGY    50
AE2     VKLVESGGGLVKPGGSLKLSCAASGFTFRTMSWVRQTPEKRLEWVAT    50

CONS5   ISXXXXXXXXYXXXXKGXXTXXXDXXXXTXXQXXSLXSEDXXXYXCXRXX
1G      ISSGSDTIYYATVKGRFTISRDNPKNTLYLQMTSLRSEDTAMYYCARPL 100
6A      ISSGSDTIYYATVKGRFTISRDNPKNTLYLQMTSLRSEDTAMYYCARPL 100
10D     ISCYNGATTYNQKFKGKATFTVDTSSNTAYMQFNSLTSEDSAVYYCARWF 100
AE1     ISCYNGAASMNRFKGKATFTVDTSSSTAYMQFNSLTSEDSAVYYCARFE 100
AE2     ISSGGSYIYYASVKGRFTISRDNAKNTLYLQMNSLKSEDTAMYYCTRDA 100

CONS5   XXXXXXXXXXYWGQGTXXTVXX            (SEQ ID NO:33)
1G      YGSSPGWFAYWGQGTLVTVSA        121  (SEQ ID NO:20)
6A      YGSSPGWFAYWGQGTLVTVSA        121  (SEQ ID NO:21)
10D     --GSTGAMDYWGQGTSVTVSS        119  (SEQ ID NO:22)
AE1     -SMTTGAMDYWGQGTSVTVSS        120  (SEQ ID NO:23)
AE2     ------HFDYWGQGTTVTVSS        115  (SEQ ID NO:24)
```

FIG. 11B

```
CONS6    XVQLQQSGXELXXPGXSVKXSCKASGYXFXXXXXXWVKXXXGXXLEWIGX
mAb2     VQLQQSGAELARPGSSVKLSCKASGYAFSSYWMNWVKQRPGQGLEWIGQ  50
B2_18-5  VQLQQSGAELARPGSSVKLSCKASGYAFDYWMNWVKQRPGQGLEWIGQ   50
B2_12-1  VQLQQSGPELVKPGASVKLSCKASGYTFDYSMHWVKLSHGKSLEWIGY   50
11D8     VQLQQSGAELARPGASVKLSCKASGYTFSQWLQWVKQRPGQGLEWIGA   69

CONS6    IYPXXXDTXYXXKFKXATLTXDXSSSXXYXXLXXLXXEDSAVYXCARXX
mAb2     IYPGSDINYNGKFKGKATLTDKSSSTAYMQLSSLTSEDSAVYYCARDY  100
B2_18-5  IYPGGDTYYNGKFKGKATLTDKSSSTAYMQLSSLISEDSAVYYCARSR  100
B2_12-1  IYPYDDIDYNQKFKTKATLTEDSSSITYLQLRSLTSEDSAVYYCARSD  100
11D8     IYPGGDTRYTQKFKGKATLTDKSSSTAYMQLTNLAPEDSAVYYCARS-  118

CONS6    XXXXXXXXXXYWGQGXXXTVSS            (SEQ ID NO:34)
mAb2     --GKD-HFDYWGQGTLVTVSS        118  (SEQ ID NO:25)
B2_18-5  -PLLDYSMHYWGQGALVTVSS        120  (SEQ ID NO:26)
B2_12-1  -GYSY-YFDYWGQGTTVTVSS        119  (SEQ ID NO:27)
11D8     ------SMDYWGQGTLVTVSS        133  (SEQ ID NO:28)
```

FIG. 11C

```
Heavy chain constant regions
CONS         AXTXXPSVXPLAPXSXXXXXXXXXLGCLVKXYFPEPVTVXWNSGKLXSGV
Human_Ighg1  ASTKGPSVFPLAPSSKSTSGGTAALGCLVKDYFPEPVTVSWNSGALTSGV  50
Mouse1_Ighg1 AKTTPPSVYPLAPGSAAQTNSMVTLGCLVKGYFPEPVTVTWNSGSLSSGV  50
Mouse2_Ighg1 AKTTPPSVYPLAPGSAAQTNSMVTLGCLVKGYFPEPVTVTWNSGSLSSGV  50

CONS         HTFPAVLQSXXLYXLSSXVTVPSSXXXXXTXXCNVXHXXSXTKVDKKXXP
Human_Ighg1  HTFPAVLQSSGLYSLSSVVTVPSSSLGTQTYICNVNHKPSNTKVDKKVEP  100
Mouse1_Ighg1 HTFPAVLQSD-LYTLSSSVTVPSSPRPSETVTCNVAHPASSTKVDKKIVP  99
Mouse2_Ighg1 HTFPAVLQSD-LYTLSSSVTVPSSTWPSETVTCNVAHPASSTKVDKKIVP  99

CONS         XXCXXXXXCXPCXXXXAPXXXXXPSVXLFPPKPKXTXMXXRTXVTCVVVD
Human_Ighg1  SCDKTHTCPPC--PAPELLGGPSVFLFPPKPKDTLMISRTPEVTCVVVD  148
Mouse1_Ighg1 RCG----CKPCICTVPE---SSVFIFPPKPKDVLTITLTPKVTCVVVD  142
Mouse2_Ighg1 RCG----CKPCICTVPE---SSVFIFPPKPKDVLTITLTPKVTCVVVD  142

CONS         XSXXDPEVXFXWXVDXVEVHXAXTXPREEQXNSTXRXVSXLXXXHQDWLN
Human_Ighg1  VSHEDPEVKFNWYVDGVEVHNAKTKPREEQYNSTYRVVSVLTVLHQDWLN  198
Mouse1_Ighg1 VSEDDPEVQFSWFVDDVEVHTAQTQPREEQFNSTFRSVSELPIMHQDWLN  192
Mouse2_Ighg1 VSEDDPEVQFSWFVDDVEVHTAQTQPREEQFNSTFRSVSELPIMHQDWLN  192

CONS         GKEXKCXVKXXXAXPAPIEKTISKKKGXPKXPQVYTXPPXXXXXXKXXVSL
Human_Ighg1  GKEYKCKVSNKALPAPIEKTISKAKGQPREPQVYTLPPSRDELTKNQVSL  248
Mouse1_Ighg1 GKEFKCRVNSAAFPAPIEKTISKTKGRPKAPQVYTIPPPKEQMAKDKVSL  242
Mouse2_Ighg1 GKEFKCRVNSAAFPAPIEKTISKTKGRPKAPQVYTIPPPKEQMAKDKVSL  242

CONS         TCXXXXFXPXDIXVEWXXNGQPXXNYKXTXPXXDXDGSXFXYSKLXVXKS
Human_Ighg1  TCLVKGFYPSDIAVEWESNGQPENNYKTTPPVLDSDGSFFLYSKLTVDKS  298
Mouse1_Ighg1 TCMITDFFPEDITVEWQWNGQPAENYKNTQPIMDTDGSYFVYSKLNVQKS  292
Mouse2_Ighg1 TCMITDFFPEDITVEWQWNGQPAENYKNTQPIMDTDGSYFVYSKLNVQKS  292

CONS         XWXXGNXFXCSVXHEXLHNHXTXKSLSXSPGK      (SEQ ID NO:38)
Human_Ighg1  RWQQGNVFSCSVMHEALHNHYTQKSLSLSPGK  330 (SEQ ID NO:35)
Mouse1_Ighg1 NWEAGNTFTCSVLHEGLHNHHTEKSLSHSPGK  324 (SEQ ID NO:36)
Mouse2_Ighg1 NWEAGNTFTCSVLHEGLHNHHTEKSLSHSPGK  324 (SEQ ID NO:37)
```

FIG. 12

```
GenBank: ARX71333.1; anti-ChE monoclonal antibody 1G, LC (SEQ ID NO:40)
  1 DILLTQSPAI LSVSPGERVS FSCRASQSIG TSIHWYQQRK NGSPRLLIKH
 51 ASESMSGIPS RFSGSGSGTD FTLSINSVES EDIADYYCQQ SNSWPTTFGA
101 GTKLELKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

FIG. 13A

```
GenBank: ARX71335.1; anti-ChE monoclonal antibody 6A, LC (SEQ ID NO:41)
  1 DVVMTQTPLT LSVTIGQPAS ISCKSSQSLL YSNGKTYLNW LLQRPGQSPK
 51 RLIYLVSKLD SGVPDRFSGS GSGTDFTLKI SRVEAEDLGV HYCEQGTHFP
101 LTFGAGTKLE LKRADAAPTV SIFPPSSEQL TSGGASVVCF LNNFYPKDIN
151 VKWKIDGSER QNGVLNSWTD QDSKDSTYSM SSTLTLTKDE YERHNSYTCE
201 ATHKTSTSPI VKSFNRNEC
```

FIG. 13B

GenBank: ARX71331.1; anti-ChE monoclonal antibody 10D, LC (SEQ ID NO:42)
```
  1 DIQMTQTTSS LSASLGDRVT ISCSASQGIS NYLNWYQQKP DGTVYLLIYY
 51 TSSLQSGVPS RFSGSGSGTD YSLTISNLES EDIATYYCQQ YSEPPFTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

FIG. 13C

GenBank: ARX71337.1; anti-ChE monoclonal antibody AE1, LC (SEQ ID NO:43)
```
  1 DIQMTQTTSS LSASLGDRVT ISCRASQDIS NYLNWYQQKP DGTVKLLIYY
 51 TSRLHSGVPS RFSGSGSGTD YSLTISNLEQ EDIATYFCQQ GKTFPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

FIG. 13D

GenBank: ARX71339.1; anti-ChE monoclonal antibody AE2, LC (SEQ ID NO:44)
```
  1 DIVISQSPSS LAVSAGEKVT MSCKSSQSLL DSRTRKNYLA WYQQKPGQSP
 51 KLLIYWASTR ESGVPDRFTG SGSGTDFTLT ISSVQAEDLA VYYCKQSYNH
101 MYTFGGGTKL EIKRADAAPT VSIFPPSSEQ LTSGGASVVC FLNNFYPKDI
151 NVKWKIDGSE RQNGVLNSWT DQDSKDSTYS MSSTLTLTKD EYERHNSYTC
201 EATHKTSTSP IVKSFNRNEC
```

FIG. 13E

GenBank: AHN49952.1; anti-ChE monoclonal antibody mAb2, LC (SEQ ID NO:45)
```
  1 DIVMTQSQKF MSTSVGDRVS VTCKASQSVG TNVAWFQQTP GQSLKVLIYS
 51 ASNRYSGVPD RFTGSGSGTD FTLTISNVQS EDLAEYFCQQ FNSYPYTFGG
101 GTKLAIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

FIG. 13F

GenBank: ALD84362.1; anti-ChE monoclonal antibody B2_18-5, LC (SEQ ID NO:46)
```
  1 DIQMTQSSSS FSVSLGDRVT ITCKTSEDIY NRLAWYQQKP GNAPRLLISG
 51 ATSLETGVPS RFSGSGSGED FTLSITSLQT EDVATYYCQQ YWSTPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

FIG. 13G

GenBank: ALD84364.1; anti-ChE monoclonal antibody B2_12-1, LC (SEQ ID NO:47)
```
  1 DIVMTQSPAT LSVTPGDRVS LSCRASQSIS DYLHWYQQKS HESPRLLIKY
 51 ASQSISGIPS RFSGGGSGSD FTLSINSVEP EDVGVYYCQN GHRFPLTFGA
101 GTKLELKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

FIG. 13H

```
GenBank: ALD84366.1; anti-ChE monoclonal antibody 11D8, LC (SEQ ID NO:48)
  1 MVSTAQFLVF LLFWIPASRG DILLTQSPAI LSVSPGERVR LSCRASQSCG
 51 TSIYWYQQRT NGSPRLLIMY ASEPFSGIPS RFSGSGSGTD FTLSINSVES
101 EDIADYYCQQ SNSWPWTFGG GTRLEIKRAD AAPTVSIFPP SSEQLTSGGA
151 SVVCFLNNFY PKDINVKWKI DGSERQNGVL NSWTDQDSKD STYSMSSTLT
201 LTKDEYERHN SYTCEATHKT STSPIVKSFN RNEC
```

FIG. 13I

```
Light chain variable regions
CONS1                          DXXXXQXXXXXXXXXGXXXXXXCXXSXXXX
CONS2                                                     XXXX
1G       ---------------------LL  PAILSV P  R SF CRAS SI-  29
6A       ---------------------VM  PLTLSV  G P SI CKSS SLL  30
10D      ---------------------QM  TSSLSA LG R TI CSAS GI-  29
AE1      ---------------------QM  TSSLSA LG R TI CRAS DI-  29
AE2      ---------------------VI  PSSLAV AG K TM CKSS SLL  30
mAb2     ---------------------VM  QKFMST VG R SV CKAS SVG  30
B2_18-5  ---------------------QM  SSSFSV LG R TI CKTS DI-  29
B2_12-1  ---------------------VM  PATLSV PG R SL CRAS SI-  29
11D8     MVSTAQFLVFLLFWIPASRG LL  PAILSV PG R RL CRAS SC-  49
                                                      CDR1

CONS1    XXXXXXXXXXWXQXXXXXXXLIXXXXXXXXGXPXRFXGXGSGXDXXLX
CONS2/3  XXXXXXXX  (SEQ ID NO:60)   XXX  (SEQ ID NO:61)
1G       ------GTS H YQ RKNGSPRL  KHA ESM G SRF GSGSGTD  S  74
6A       YSNG-KTY N LL RPGQSPKR  YLV KLD G DRF GSGSGTD  K  79
10D      ------SNY N YQ KPDGTVYL  YYT SLQ G PSRF GSGSGTD  T  74
AE1      ------SNY N YQ KPDGTVKL  YYT RLH G PSRF GSGSGTD  T  74
AE2      DSRTRKNY A YQ KPGQSPKL  YWA TRE G PDRF GSGSGTD  T  80
mAb2     TN------ A FQ TPGQSLKV  YSA NRY G PDRF GSGSGTD  T  74
B2_18-5  -----YNR A YQ KPGNAPRL  SGA SLE G PSRF GSGSGED  S  74
B2_12-1  -----SDY H YQ KSHESPRL  KYA QSI G PSNF GGSGSD   S  74
11D8     -----GTS Y YQ RTNGSPRL  MYA EPF G SRF GSGSGTD   S  94
         CDR1                     CDR2

CONS1    IXXXXXEDXXXXCXXXXXXXXTFGXGTXLXXKR       (SEQ ID NO:59)
CONS4        XXXXXXXXT          (SEQ ID NO:62)
1G       NS SED DY CQ SNSWPT FG GT LE KR   108  (SEQ ID NO:50)
6A       SR AED VH CE GTHFPL FG GT LE KR   113  (SEQ ID NO:51)
10D      SN SED TY CQ YSEPPF FG GT LE KR   108  (SEQ ID NO:52)
AE1      SN QED TY CQ GKTFPY FG GT LE KR   108  (SEQ ID NO:53)
AE2      SS AED VY CK SYNHMY FG GT LE KR   114  (SEQ ID NO:54)
mAb2     SN SED EY CQ FNSYPY FG GT LA KR   108  (SEQ ID NO:55)
B2_18-5  TS TED TY CQ YWSTPY FG GT LE KR   108  (SEQ ID NO:56)
B2_12-1  NS PED VY CQ GHRFPL FG GT LE KR   108  (SEQ ID NO:57)
11D8     NS SED DY CQ SNSWPW FG GT LE KR   128  (SEQ ID NO:58)
               CDR3
```

FIG. 14A

```
CONS  DXXXXQXXXXLXXXXGXXXXXSCXXSQXXXXXXXXXXXXXWXXQXXXXX
1G    DLLTQPAILSVPGERVSFSCRASQS------GTSHWYQQKNGSP  44
6A    DVMTQPLTLSLGQPTSISCKSSQSLYSNG-KTYNWLLQKPGQSP  49
10D   DQMTQTSSSLSALGRVTISCSASQG------SNYNWYQQKPDGTV  44
AE1   DQMTQTSSSLSALGRVTISCRASQD------SNYNWYQQKPDGTV  44
AE2   DVITQPSSLAVSAGEKVMSCKSSQSLDSRTKNYLAWYQQKPGQSP  50

CONS  XXLIXXKSXXXSGKPXRFXGSGSGTDXXLKIXXXXXEDXXXXXCXQXXXX
1G    RLITKHASESMSGIPSRFSGSGSGTDFTLSINSVSEDLADYFCQQSNSW  94
6A    KRLIYLVSKLDSGVPDRFSGSGSGTDFTLKISRVAEDLVHVCEQGTHF  99
10D   YLIYYTSSLQSGIPSRFSGSGSGTDFTLTSSNVSEDLTTYFCQQYSEP  94
AE1   KLIYYTSRLHSGVPSRFSGSGSGTDFTLTSSNVQEDLTTYFCQQGKTF  94
AE2   KLIYWASTRESGVPDRFSGSGSGTDFTLTSSSVAEDLVYFCKQSYNH 100

CONS  XXTFGXGTKLEXKR           (SEQ ID NO:63)
1G    PTFTFGSGTKLEIKR  108    (SEQ ID NO:50)
6A    PLTFGSGTKLELKR   113    (SEQ ID NO:51)
10D   PFTFGSGTKLEIKR   108    (SEQ ID NO:52)
AE1   PYTFGSGTKLEIKR   108    (SEQ ID NO:53)
AE2   MYTFGSGTKLEIKR   114    (SEQ ID NO:54)
```

FIG. 14B

```
CONS    DIXXTQSXXXXSXXXGXRVXXXCXXSXXXXXXXXXXXXXWXQQXXXXX
mAb2    DIVMTQSQKFMSTIVGRVSLTCKASGSVGTN------AWYQQTPGQSL  44
B2_18-5 DIQMTQSSSSFSVLGDRVTITCSTSDI----------YNRWAWQQKPGNAP  44
B2_12-1 DIVMTQSPATLSVTPGRVSLSCKASQSI----------SDYLHWQQKSHESP  44
11D8    DLLLTQSPAILSVTPGERVSLTCRASQSC------GTSYWHQQRTNGSP  64

CONS    XXLIXXAXXXXXGKPXRFXGKGSGXDFTLKIXXXXXXEDXXXYXCQXXXX
mAb2    LLIYSASNRYTGVPDRFTGSGSGTDFTLTSNVSEDLAEYFCFQFNSY  94
B2_18-5 LLIISGASLESGVPSRFSGSGSGEDFTLSITSLTEDLATYYCYQYWST  94
B2_12-1 LLIKYAFQSINGVPSRFCGGSCSDFTLTINSVPEDLAVYYCQGHRF  94
11D8    LMIMYAEEPFSGIPSRFSGSGSGTDFTLSINSLSEDFADYLCLQSNSW 114

CONS    PXTFGXGTXLXXKR           (SEQ ID NO:64)
mAb2    PYTFGQGTKLAIKR   108    (SEQ ID NO:55)
B2_18-5 PYTFGQGTKLEIKR   108    (SEQ ID NO:56)
B2_12-1 PLTFGGGTKLEIKR   108    (SEQ ID NO:57)
11D8    PWTFGQGTKLEIKR   128    (SEQ ID NO:58)
```

FIG. 14C

```
CONS          XXXAAPXVXIFPPSXEQLXSGXASVVCXLNNFYPXXXXVXWKXDXXXXXX
Human1_Igkc   -TVAAPSVFIFPPSDEQLKSGTASVVCLLNNFYPREAKVQWKVDNALQSG  49
Human2_Igkc   RTVAAPSVFIFPPSDEQLKSGTASVVCLLNNFYPREAKVQWKVDNALQSG  50
Mouse1_Igkc   -ADAAPTVSIFPPSSEQLTSGGASVVCFLNNFYPKDINVKWKIDGSERQN  49
Mouse2_Igkc   RADAAPTVSIFPPSSEQLTSGGASVVCFLNNFYPKDINVKWKIDGSERQN  50

CONS          XXXXSXTXQDSKDSTYSXSSTLTLXKXXYEXHXXYXCEXTHXXXKSPXXK
Human1_Igkc   NSQESVTEQDSKDSTYSLSSTLTLSKADYEKHKVYACEVTHQGLSSPVTK  99
Human2_Igkc   NSQESVTEQDSKDSTYSLSSTLTLSKADYEKHKVYACEVTHQGLSSPVTK  100
Mouse1_Igkc   GVLNSWTDQDSKDSTYSMSSTLTLTKDEYERHNSYTCEATHKTSTSPIVK  99
Mouse2_Igkc   GVLNSWTDQDSKDSTYSMSSTLTLTKDEYERHNSYTCEATHKTSTSPIVK  100

CONS          SFNRXEC          (SEQ ID NO:74)
Human1_Igkc   SFNRGEC  106     (SEQ ID NO:70)
Human2_Igkc   SFNRGEC  107     (SEQ ID NO:71)
Mouse1_Igkc   SFNRNEC  106     (SEQ ID NO:72)
Mouse2_Igkc   SFNRNEC  107     (SEQ ID NO:73)
```

FIG. 15

DETECTION OF CHOLINESTERASE INHIBITION WITH MICROFLUIDIC DEVICES AND SYSTEMS THEREOF

CROSS-REFERENCE TO RELATED APPLICATION

This application claims the benefit of U.S. Provisional Application No. 62/961,800, filed Jan. 16, 2020, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SANDP008_2_ST25.txt," created on Feb. 11, 2021 (size of 183 kilobytes), which is hereby incorporated by reference in its entirety.

FIELD OF THE INVENTION

The present invention relates to methods of conducting cholinesterase inhibition assays. In one instance, the assays can be configured to determine the presence of inactivated and activated cholinesterases. Also described herein are microfluidic devices and systems for conducting such assays.

BACKGROUND OF THE INVENTION

Markers for exposure to chemical warfare agents are unstable, and detection can be difficult. For instance, certain assays are specific for known agents provided within a panel, but false negative results can be provided if exposure arose from an unknown agent that is absent from the panel. Thus, there is a need for additional assay formats that can provide inhibition of blood cholinesterases, the physiological enzyme that is inhibited by such chemical agents.

SUMMARY OF THE INVENTION

The present invention relates to methods for conducting a cholinesterase inhibition assay, in which cholinesterase within a sample is captured upon beads and then detected by use of probe(s) and/or detection antibody(ies). In particular, use of a bead-based format allows for separation of the captured cholinesterases from other components within the sample, thereby possibly increasing sensitivity of this assay.

In a first aspect, the present invention features a method of conducting a cholinesterase inhibition assay, the method including: generating a plurality of complexes on a plurality of beads in a fluid sample, each of the individual complexes, independently, of the plurality of complexes including a capture agent and one of an activated cholinesterase or an inactivated cholinesterase; transporting the plurality of beads including the complexes through a density medium in a detection chamber; and detecting a presence or an absence of a first signal from the activated cholinesterase in the detection chamber. In some embodiments, the first signal arises from reacting the activated cholinesterase with a first probe and an optional second probe.

In some embodiments, each of the individual complexes includes a capture agent and an activated cholinesterase. In other embodiments, each bead includes a plurality of complexes, in which a first population of the plurality of complexes includes a capture agent and an activated cholinesterase and a second population of the plurality of complexes includes a capture agent and an inactivated cholinesterase, such that a single bead includes both inactivated cholinesterase and activated cholinesterase.

In some embodiments, the method includes (e.g., before or after the transporting step): binding a detection antibody to one or more of the plurality of complexes on the plurality of beads, thereby providing one or more detectable complexes; and detecting a second signal from the detection antibody of the one or more detectable complexes bound to the plurality of beads.

In a second aspect, the present invention features a method of conducting a cholinesterase inhibition assay, the method including: generating a plurality of complexes on a plurality of beads in a fluid sample, each of the individual complexes, independently, of the plurality of complexes including a capture agent and one of an activated cholinesterase or an inactivated cholinesterase; binding a detection antibody to one or more of the plurality of complexes on the plurality of beads, thereby providing one or more detectable complexes; transporting the plurality of beads including the detectable complexes through a density medium in a detection chamber; detecting a first signal from the activated cholinesterase in the detection chamber, wherein the first signal arises from reacting the activated cholinesterase with a first probe and an optional second probe; and further detecting a second signal from the detection antibody of the one or more detectable complexes bound to the plurality of beads, wherein the detecting step and the further detecting step can be conducted in any order or at the same time.

In some embodiments, the binding step is conducted after the transporting step.

In a third aspect, the present invention features a microfluidic device including: a substrate including a sample port configured to receive a fluid sample; a main channel disposed, at least in part, within or on the substrate, wherein the main channel is in fluidic communication with the sample port; and an assay area disposed, at least in part, within or on the substrate, wherein the assay area is in fluidic communication with main channel that is configured to deliver the fluid sample, or a portion thereof, into the assay area.

In some embodiments, the assay area includes a detection chamber; a density medium, a first probe, and an optional second probe disposed within the detection chamber; a reaction chamber configured to contain the fluid sample including a plurality of complexes on a plurality of beads, each of the individual complexes, independently, of the plurality of complexes including a capture agent and one of an activated cholinesterase or an inactivated cholinesterase; and a channel in fluidic communication with the detection chamber and the reaction chamber. In other embodiments, the detection chamber is configured to transport the plurality of beads, or a portion thereof, through the density medium when subjected to a sedimentation force. In yet other embodiments, the first probe and the optional second probe are configured to react with the activated cholinesterase bound to at least one of the plurality of beads.

In some embodiments, the reaction chamber and/or the detection chamber further includes a detection antibody configured to bind to one or more of the plurality of complexes on the plurality of beads, thereby providing one or more detectable complexes.

In some embodiments, the channel is further configured to restrict transport of at least a portion of the fluid sample through the density medium.

In a fourth aspect, the present invention features a system including: a microfluidic disc including a substrate including a sample port configured to receive a fluid sample; a motor module configured to be coupled to the microfluidic disc and to spin the microfluidic disc in response to a motor control signal; and a detection module configured to detect one or more signals present in the detection chamber.

In some embodiments, the microfluidic disc further includes: a main channel disposed, at least in part, within or on the substrate, wherein the main channel is in fluidic communication with the sample port; and an assay area disposed, at least in part, within or on the substrate, wherein the assay area is in fluidic communication with main channel that is configured to deliver the sample, or a portion thereof, into the assay area. In further embodiments, the assay area includes a detection chamber; a density medium, a first probe, and an optional second probe disposed within the detection chamber; a reaction chamber configured to contain the fluid sample including a plurality of complexes on a plurality of beads, each of the individual complexes of the plurality of complexes, independently, including a capture agent and one of an activated cholinesterase or an inactivated cholinesterase; and a channel in fluidic communication with the detection chamber and the reaction chamber.

In some embodiments, the detection chamber is configured to transport the plurality of beads, or a portion thereof, through the density medium when subjected to a sedimentation force.

In some embodiments, the first probe and the optional second probe are configured to react with the activated cholinesterase bound to at least one of the plurality of beads. In other embodiments, the one or more signals arise from reacting the activated cholinesterase with the first probe and the optional second probe, and wherein the detection module is configured to generate an electronic detection signal based, at least in part, on the presence of the one or more signals.

In some embodiments, the system further includes: a processing device coupled to the motor module and the detection module. In further embodiments, the processing device is configured to generate the motor control signal and provide the motor control signal to the motor module. In other embodiments, the processing device is further configured to receive the electronic detection signal from the detection module.

In some embodiments, the reaction chamber and/or the detection chamber further includes a detection antibody configured to bind to one or more of the plurality of complexes on the plurality of beads, thereby providing one or more detectable complexes.

In any embodiment herein, the density medium has a density lower than a density of the beads and higher than a density of the fluid sample. In some embodiments, the density medium is characterized by a density that is less than the density of the plurality of beads. In other embodiments, the density medium is characterized by a density that is more than a density of the fluid sample.

In any embodiment herein, the transporting occurs, at least in part, by sedimentation.

In any embodiment herein, the activated or inactivated cholinesterase is an acetylcholinesterase or a butyrylcholinesterase. In some embodiments, the inactivated cholinesterase is an acetylcholinesterase or a butyrylcholinesterase bound to an inactivator (e.g., an organophosphorus agent or any inhibitor described herein). In some embodiments, the activated or inactivated cholinesterase includes a polypeptide sequence having at least 90% sequence identity to any one of the following: SEQ ID NOs:2-8 or a fragment thereof. In other embodiments, the activated or inactivated cholinesterase includes a polypeptide sequence having at least 90% sequence identity to any one of the following: SEQ ID NOs:10, 11, or a fragment thereof, in which each X at each position of SEQ ID NO:10 is an amino acid (or a conservative amino acid substitution thereof) present at a position in one of SEQ ID NOs:2-8 when optimally aligned with SEQ ID NO:10; and in which each X at each position of SEQ ID NO:11 is an amino acid (or a conservative amino acid substitution thereof) present at a position in one of SEQ ID NOs:2-8 when optimally aligned with SEQ ID NO:11.

In any embodiment herein, the capture agent binds to both the activated cholinesterase and the inactivated cholinesterase. In some embodiments, the capture agent is an antibody. In some embodiments, the capture agent (e.g., a heavy chain variable region of the capture agent or the antibody) includes a polypeptide sequence having at least 90% sequence identity to any one of the following: SEQ ID NOs:20-28 or a fragment thereof. In other embodiments, the capture agent (e.g., a heavy chain variable region of the capture agent or the antibody) includes a polypeptide sequence having at least 90% sequence identity to SEQ ID NOs:29, 33, 34, or a fragment thereof, in which each X at each position of SEQ ID NO:29 is an amino acid (or a conservative amino acid substitution thereof) present at a position in one of SEQ ID NOs:20-28 when optimally aligned with SEQ ID NO:29; in which each X at each position of SEQ ID NO:33 is an amino acid (or a conservative amino acid substitution thereof) present at a position in one of SEQ ID NOs:20-24 when optimally aligned with SEQ ID NO:33; and in which each X at each position of SEQ ID NO:34 is an amino acid (or a conservative amino acid substitution thereof) present at a position in one of SEQ ID NOs:25-28 when optimally aligned with SEQ ID NO:34. In yet another embodiment, the capture agent (e.g., a complementarity-determining region in the heavy chain variable region of the capture agent or the antibody) includes a polypeptide sequence having at least 90% sequence identity to SEQ ID NOs:30-32, in which each X at each position of SEQ ID NOs:30-32 is an amino acid (or a conservative amino acid substitution thereof) present at a position in one of SEQ ID NOs:20-28 when optimally aligned with SEQ ID NO:30-32, respectively.

In some embodiments, the capture agent (e.g., a light chain variable region of the capture agent or the antibody) includes a polypeptide sequence having at least 90% sequence identity to any one of the following: SEQ ID NOs:40-48, 50-58, or a fragment thereof. In other embodiments, the capture agent (e.g., a light chain variable region of the capture agent or the antibody) includes a polypeptide sequence having at least 90% sequence identity to SEQ ID NOs:59, 63, 64, or a fragment thereof, in which each X at each position of SEQ ID NO:59 is an amino acid (or a conservative amino acid substitution thereof) present at a position in one of SEQ ID NOs:50-58 when optimally aligned with SEQ ID NO:59; in which each X at each position of SEQ ID NO:63 is an amino acid (or a conservative amino acid substitution thereof) present at a position in one of SEQ ID NOs:50-54 when optimally aligned with SEQ ID NO:63; and in which each X at each position of SEQ ID NO:64 is an amino acid (or a conservative amino acid substitution thereof) present at a position in one of SEQ ID NOs:55-58 when optimally aligned with SEQ ID NO:64. In yet another embodiment, the capture agent (e.g., a complementarity-determining region in the light chain variable region of the capture agent or the antibody) includes a polypeptide sequence having at least 90% sequence identity to SEQ ID NOs:60-62, in which each X at each position of SEQ ID NOs:60-62 is an amino acid (or a conservative amino acid substitution thereof) present at a position in one of SEQ ID NOs:50-58 when optimally aligned with SEQ ID NO:60-62, respectively.

In any embodiment herein, the detection antibody binds to both the activated cholinesterase and the inactivated cholinesterase.

In any embodiment herein, the first probe and/or the second probe, if present, includes a compound of formula (I), (Ia), (IV), (VI), (VIa), or (VIII), or a salt thereof.

In any embodiment herein, the detection chamber is disposed within a substrate and the transporting step includes spinning the substrate.

In any embodiment herein, the fluid sample includes a nasal fluid or a cerebrospinal fluid.

In any embodiment herein, the methods, devices, and/or systems employ a first population of beads is characterized by a first density and/or a first radius. In some embodiments, the first population of beads is configured to bind to a first target of interest. In other embodiments, the first population of beads is configured to bind to a second target of interest that is different from the first target of interest. In yet other embodiments, the first population of beads further includes one or more capture agents configured to bind the first target of interest, thereby forming a population of captured target-bead complexes. In further embodiments, the one or more detection agents is configured to bind to the population of captured target-bead complexes, or a portion thereof.

In any embodiment herein, the methods, devices, and/or systems employ a second population of beads, in which the second population is optionally characterized by a second density and/or a second radius (e.g., where the second density is different than the first density and/or where the second radius is different than the first radius). In some embodiments, the second population of beads is configured to bind to a second target of interest (e.g., where the second target of interest is different than the first target of interest).

In any embodiment herein, the methods, devices, and/or systems employ a density medium that is characterized by a density that is less than the density of the plurality of beads. In some embodiments, the density medium includes a plurality of components each characterized by a particular density or density range. In other embodiments, the density medium is characterized by a density that is greater than the fluid sample and less than the density of the plurality of beads.

In any embodiment herein, the sedimentation force is generated by gravity and/or centrifugal force.

In any embodiment herein, the detection chamber is defined within a microfluidic disc.

In any embodiment herein, the microfluidic disc further includes a reaction chamber configured to receive the sample; and a channel configured to transport the capture agents, detection agents, and/or probes to the reaction chamber that is in fluidic communication with the detection chamber. Additional details follow.

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm and, optionally, equal to or larger than about 1 μm. For instance, a microfluidic structure (e.g., any structure described herein) can have a length, width, height, cross-sectional dimension, circumference, radius (e.g., external or internal radius), or diameter that is less than 1 mm.

By "nano" is meant having at least one dimension that is less than 1 μm but equal to or larger than about 1 nm. For instance, a nanostructure (e.g., any structure described herein, such as a nanoparticle) can have a length, width, height, cross-sectional dimension, circumference, radius (e.g., external or internal radius), or diameter that is less than 1 μm but equal to or larger than 1 nm. In other instances, the nanostructure has a dimension that is of from about 1 nm to about 1 μm.

As used herein, the terms "top," "bottom," "upper," "lower," "above," and "below" are used to provide a relative relationship between structures. The use of these terms does not indicate or require that a particular structure must be located at a particular location in the apparatus.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkenylene" is meant a multivalent (e.g., bivalent, trivalent, tetravalent, etc.) form of an alkenyl group, as described herein. In some embodiments, the alkenylene group is a $C_{2-3}$, $C_{2-6}$, $C_{2-12}$, $C_{2-16}$, $C_{2-18}$, $C_{2-20}$, or $C_{2-24}$ alkylene group. The alkenylene group can be branched or unbranched. The alkenylene group can also be substituted or unsubstituted. For example, the alkenylene group can be substituted with one or more substitution groups, as described herein for alkyl.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N3 group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O)Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$R$^D$, where R$^D$ is selected from the group consisting of (a) $C_{1-6}$ alkyl, (b) $C_{4-18}$ aryl, and (c) $C_{1-6}$ alk-$C_{4-18}$ aryl; (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)Ak, in which Ak is an alkyl group, as defined herein); (2) $C_{1-6}$ alkyl; (3) $C_{1-6}$ alkoxy (e.g., —OAk, in which Ak is an alkyl group, as defined herein); (4) $C_{1-6}$ alkoxy-$C_{1-6}$ alkyl (e.g., an alkyl group, which is substituted with an alkoxy group —OAk, in which Ak is an alkyl group, as defined herein); (5) $C_{1-6}$ alkylsulfinyl (e.g., —S(O)Ak, in which Ak is an alkyl group, as defined herein); (6) $C_{1-6}$ alkylsulfinyl-$C_{1-6}$ alkyl (e.g., an alkyl group, which is substituted by an alkylsulfinyl group —S(O)Ak, in which Ak is an alkyl group, as defined herein); (7) $C_{1-6}$ alkylsulfonyl (e.g., —SO$_2$Ak, in which Ak is an alkyl group, as defined herein); (8) $C_{1-6}$ alkylsulfonyl-$C_{1-6}$ alkyl (e.g., an alkyl group, which is substituted by an alkylsulfonyl group —SO$_2$Ak, in which Ak is an alkyl group, as defined herein); (9) aryl; (10) amino (e.g., —R$^{N1}$R$^{N2}$ where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (11) $C_{1-6}$ aminoalkyl (e.g., meant an alkyl group, as defined herein, substituted by an amino group); (12) heteroaryl; (13) $C_{1-6}$ alk-$C_{4-18}$ aryl (e.g., -A$^L$Ar, in which A$^L$ is an alkylene group and Ar is an aryl group, as defined herein); (14) aryloyl (e.g., —C(O)Ar, in which Ar is an aryl group, as defined herein); (15) azido (e.g., an —N3 group); (16) cyano (e.g., a —CN group); (17) $C_{1-6}$ azidoalkyl (e.g., a —N3 azido group attached to the parent molecular group through an alkyl group, as defined herein); (18) carboxyaldehyde (e.g., a —C(O)H group); (19) carboxyaldehyde-$C_{1-6}$ alkyl (e.g., -A$^L$C(O)H, in which A$^L$ is an alkylene group, as defined herein); (20) $C_{3-8}$ cycloalkyl; (21) $C_{1-6}$ alk-$C_{3-8}$ cycloalkyl (e.g., -A$^L$Cy, in which A$^L$ is an alkylene group and Cy is a cycloalkyl group, as defined herein); (22) halo (e.g., F, Cl, Br, or I); (23) $C_{1-6}$ haloalkyl (e.g., an alkyl group as defined herein, substituted with one or more halo); (24) heterocyclyl; (25) heterocyclyloxy (e.g., —OHet, in which Het is a heterocyclyl group); (26) heterocyclyloyl (e.g., —C(O)Het, in which Het is a heterocyclyl group); (27) hydroxyl (e.g., a —OH group); (28) $C_{1-6}$ hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —N02 group); (30) $C_{1-6}$ nitroalkyl (e.g., an alkyl group, as defined herein, substituted by one to three nitro groups); (31) N-protected amino; (32) N-protected amino-$C_{1-6}$ alkyl; (33) oxo (e.g., an =O group); (34) $C_{1-6}$ thioalkoxy (e.g., —SAk, in which Ak is an alkyl group, as defined herein); (35) thio-$C_{1-6}$ alkoxy-$C_{1-6}$ alkyl (e.g., an alkyl group, which is substituted by an thioalkoxy group -SAk, in which Ak is an alkyl group, as defined herein); (36) —(CH$_2$)$_r$CO$_2$R$^A$, where r is an integer of from zero to four, and R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —(CH$_2$)$_r$CONR$^B$R$^C$, where r is an integer of from zero to four and where each R$^B$ and R$^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —(CH$_2$)$_r$SO$_2$R$^D$, where r is an integer of from zero to four and where R$^D$ is selected from the group consisting of (a) $C_{1-6}$ alkyl, (b) $C_{4-18}$ aryl, and (c) $C_{1-6}$ alk-$C_{4-18}$ aryl; (39) —(CH$_2$)$_r$SO$_2$NR$^E$R$^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —(CH$_2$)$_r$NR$^G$R$^H$, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45) cycloalkoxy (e.g., —OCy, in which Cy is a cycloalkyl group, as defined herein); (46) cycloalkylalkoxy (e.g., —OA$^L$Cy, in which A$^L$ is an alkylene group and Cy is a cycloalkyl group, as defined herein); and (47) arylalkoxy (e.g., —OA$^L$Ar, in which A$^L$ is an alkylene group and Ar is an aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a multivalent (e.g., bivalent, trivalent, tetravalent, etc.) form of an aryl group, as described herein. Exemplary arylene groups include phenylene, naphthylene, biphenylene, triphenylene, diphenyl ether, acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group. The arylene group can be branched or unbranched. The arylene group can also be substituted or unsubstituted. For example, the arylene group can be substituted with one or more substitution groups, as described herein for aryl.

By "cyano" is meant a —CN group.

By "halo" is meant F, Cl, Br, or I.

By "haloalkyl" is meant an alkyl group, as defined herein, substituted with one or more halo.

By "heteroalkylene" is meant a divalent form of an alkylene group, as defined herein, containing one, two, three, or four non-carbon heteroatoms (e.g., independently selected from the group consisting of nitrogen, oxygen, phosphorous, sulfur, or halo).

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, benzodioxolyl, furyl, furanyl, thienyl, thiazolidinyl, isothiazolyl, isoindazoyl, triazolyl, tetrazolyl, tetrazolinyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like. The heterocyclyl group can be substituted with one, two, three, four, or five substituents independently selected from the group consisting of: (1) $C_{1-6}$ alkanoyl; (2) $C_{1-6}$ alkyl; (3) $C_{1-6}$ alkoxy; (4) $C_{1-6}$ alkoxy-$C_{1-6}$ alkyl; (5) $C_{1-6}$ alkylsulfinyl; (6) $C_{1-6}$ alkylsulfinyl-$C_{1-6}$ alkyl; (7) $C_{1-6}$ alkylsulfonyl; (8) $C_{1-6}$ alkylsulfonyl-$C_{1-6}$ alkyl; (9) aryl; (10) amino; (11) $C_{1-6}$ aminoalkyl; (12) heteroaryl; (13) $C_{1-6}$ alk-$C_{4-18}$ aryl; (14) aryloyl; (15) azido; (16) cyano; (17) $C_{1-6}$ azidoalkyl; (18) carboxyaldehyde; (19) carboxyaldehyde-$C_{1-6}$ alkyl; (20) $C_{3-8}$ cycloalkyl; (21) $C_{1-6}$ alk-$C_{3-8}$ cycloalkyl; (22) halo; (23) $C_{1-6}$ haloalkyl; (24) heterocyclyl; (25) heterocyclyloxy; (26) heterocyclyloyl; (27) hydroxyl; (28) $C_{1-6}$ hydroxyalkyl; (29) nitro; (30) $C_{1-6}$ nitroalkyl; (31) N-protected amino; (32) N-protected amino-$C_{1-6}$ alkyl; (33) oxo; (34) $C_{1-6}$ thioalkoxy; (35) thio-$C_{1-6}$ alkoxy-$C_{1-6}$ alkyl; (36) —(CH$_2$)$_r$CO$_2$R$^A$, where r is an integer of from zero to four, and R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —(CH$_2$)$_r$CONR$^B$R$^C$, where r is an integer of from zero to four and where each R$^B$ and R$^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —(CH$_2$)$_r$SO$_2$R$^D$, where r is an integer of from zero to four and where R$^D$ is selected from the group consisting of (a) $C_{1-6}$ alkyl, (b) $C_{4-18}$ aryl, and (c) $C_{1-6}$ alk-$C_{4-18}$ aryl; (39) —(CH$_2$)$_r$SO$_2$NR$^E$R$^F$, where r is an integer of from zero to four and where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —(CH$_2$)$_r$NR$^G$R$^H$, where r is an integer of from zero to four and where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl; (43) perfluoroalkoxy; (44) aryloxy; (45) cycloalkoxy; (46) cycloalkylalkoxy; and (47) arylalkoxy.

By "hydroxyl" is meant —OH.

By "phosphoryl" is meant a —P(O)< group.

By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P. G. M. Wuts and T. W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkylsulfonate with reactive group O), such as —SO$_2$—R$^{S1}$, where R$^{S1}$ is optionally substituted $C_{1-12}$ alkyl, such as mesyl or benzylsulfonyl; an optionally substituted arylsulfonyl group (e.g., forming an arylsulfonate with reactive group O), such as —SO$_2$—R$^{S4}$, where R$^{S4}$ is optionally substituted C$_{4-18}$ aryl, such as tosyl or phenylsulfonyl; an optionally substituted alkoxycarbonyl or aryloxycarbonyl group (e.g., forming a carbonate with reactive group O), such as —C(O)—OR$^{T1}$, where R$^{T1}$ is optionally substituted C$_{1-12}$ alkyl or optionally substituted C$_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—(R$^{T2}$)$_3$, where each R$^{T2}$ is, independently, optionally substituted C$_{1-12}$ alkyl or optionally substituted C$_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenylsulfonyl, benzyl, Boc, and Cbz. Such protecting groups can employ any useful agent to cleave the protecting group, thereby restoring the reactivity of the unprotected reactive group.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," *J. Pharm. Sci.* 1977 January; 66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature ($T_m$) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., Adv. Appl. Math. 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones. Non-limiting amino acids include glycine (Gly, G), alanine (Ala, A), valine (Val, V), isoleucine (Ile, I), leucine (Leu, L), cysteine (Cys, C), methionine (Met, M), aspartic acid (Asp, D), glutamic acid (Glu, E), arginine (Arg, R), histidine (His, H), lysine (Lys, K), asparagine (Asn, N), glutamine (Gln, Q), serine (Ser, S), threonine (Thr, T), proline (Pro, P), phenylalanine (Phe, F), tyrosine (Tyr, Y), tryptophan (Trp, W), selenocysteine (Sec, U), and pyrrolysine (Pyl, O).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); a group of amino acids having sulfur containing side chains consists of cysteine (Cys, C) and methionine (Met, M); and a group having hydroxyl, sulfur, or selenium containing side chains consists of serine (Ser, S), threonine (Thr, T), cysteine (Cys, C), methionine (Met, M), and selenocysteine (Sec, U). Exemplary conservative amino acid substitution groups are valine-leucine-isoleucine, phenylalanine-tyrosine, lysine-arginine, alanine-valine, glycine-serine, glutamate-aspartate, and asparagine-glutamine. The present disclosure encompasses any sequence having a conservative amino acid sequence of any polypeptide sequence described herein.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (see, e.g., Smith T F et al., *J. Mol. Biol.* 1981; 147:195-7) and BLAST (Basic Local Alignment Search Tool; see, e.g., Altschul S F et al., *J. Mol. Biol.* 1990; 215:403-10). These and other alignment algorithms are accessible using publicly available computer software such as "Best Fit" (see, e.g., Smith T F et al., *Adv. Appl. Math.* 1981; 2(4):482-9) as incorporated into GeneMatcher Plus™ (see, e.g., Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof. Two components can be attached by any useful linker described herein.

By "linker" is meant any useful multivalent (e.g., bivalent) component useful for joining to different portions or segments. Exemplary linkers include a nucleic acid sequence, a chemical linker, etc. The linker may include a covalent linker or a non-covalent linker. In some embodiments: the linker may comprise a flexible arm, e.g., 2, 3, 4, 5, 6, 7, 8, 9, 10, 11, 12, 13, 14, or 15 carbon atoms. Exemplary linkers include BS3 ([bis(sulfosuccinimidyl)suberate]; BS3 is a homobifunctional N-hydroxysuccinimide ester that targets accessible primary amines), NHS/EDC (N-hydroxysuccinimide and N-ethyl-'(dimethylaminopropyl)carbodiimide; NHS/EDC allows for the conjugation of primary amine groups with carboxyl groups), sulfo-EMCS ([N-ε-maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups). Examples of other suitable linkers are succinic acid, Lys, Glu, Asp, a dipeptide such as Gly-Lys, an α-helical linker (e.g., A(EAAAK)$_n$A (SEQ ID NO:75), where n is 1, 2, 3, 4, or 5), an alkyl chain (e.g., an optionally substituted $C_{1-12}$ alkylene or alkynyl chain), or a polyethylene glycol (e.g., $(CH_2CH_2O)_m$, where m is from 1 to 50).

By "subject" or "host", which can be used interchangeably, is meant a human or non-human animal (e.g., a mammal). In some embodiments, the host can have or can be suspected of being exposed to an inhibitor (e.g., exposed to an organophosphate agent).

Other features and advantages of the invention will be apparent from the following description and the claims.

BRIEF DESCRIPTION OF THE DRAWINGS

FIG. 8A-8G shows sequences for non-limiting cholinesterases. Provided are polypeptide sequences for (A) human acetylcholinesterase (AChE) (SEQ ID NO:2), (B) human butyrylcholinesterase (BChE) (SEQ ID NO:3), (C) mouse AChE (SEQ ID NO:4), (D) mouse BChE (SEQ ID NO:5), (E) bovine AChE (SEQ ID NO:6), (F) bovine BChE (SEQ ID NO:7), and (G) rat AChE (SEQ ID NO:8).

FIG. 9A-9C shows a sequence alignment of non-limiting binding cholinesterases. Provided are a first consensus sequence (SEQ ID NO:10) and a second consensus sequence (SEQ ID NO:11), in which each X at each position of SEQ ID NOs:10-11 can be an amino acid (or a conservative amino acid substitution thereof) present at a position in one of SEQ ID NOs:2-8 when optimally aligned with SEQ ID NOs:10-11, respectively.

FIG. 10A-10I shows sequences for non-limiting portions of capture agents. Provided are polypeptide sequences for heavy chain (HC) variable regions for anti-cholinesterase (anti-ChE) monoclonal antibodies, including (A) antibody 1G (SEQ ID NO:20), (B) antibody 6A (SEQ ID NO:21), (C) antibody 10D (SEQ ID NO:22), (D) antibody AE1 (SEQ ID NO:23), (E) antibody AE2 (SEQ ID NO:24), (F) antibody mAb2 (SEQ ID NO:25), (G) antibody B2_18-5 (SEQ ID NO:26), (H) antibody B2_12-1 (SEQ ID NO:27), and (I) antibody 11D8 (SEQ ID NO:28).

FIG. 11A-11C shows sequence alignments of non-limiting portions of capture agents. Provided are consensus polypeptide sequences for HC variable regions for anti-ChE monoclonal antibodies, including (A) a first consensus sequence (CONS1, SEQ ID NO:29), a second consensus sequence (first complementarity-determining region or CDR1, SEQ ID NO:30), a third consensus sequence (second CDR or CDR2, SEQ ID NO:31), and a fourth consensus sequence (third CDR or CDR3, SEQ ID NO:32), in which each X at each position of SEQ ID NOs:29-32 is an amino acid (or a conservative amino acid substitution thereof) present at a position in one of SEQ ID NOs:20-28 when optimally aligned with SEQ ID NO:29-32, respectively. Also provided are (B) a fifth consensus sequence (CONS5, SEQ ID NO:33), in which each X at each position of SEQ ID NO:33 is an amino acid (or a conservative amino acid substitution thereof) present at a position in one of SEQ ID NOs:20-24 when optimally aligned with SEQ ID NO:33; and (C) a sixth consensus sequence (CONS6, SEQ ID NO:34), in which each X at each position of SEQ ID NO:34 is an amino acid (or a conservative amino acid substitution thereof) present at a position in one of SEQ ID NOs:25-28 when optimally aligned with SEQ ID NO:34.

FIG. 12 shows a sequence alignment of non-limiting portions of capture agents. Provided are polypeptide sequences for HC constant regions for anti-ChE antibodies, including human immunoglobulin heavy constant gamma 1 (IGHG1, SEQ ID NO:35), mouse IGHG1 (SEQ ID NO:36), another mouse IGHG1 (SEQ ID NO:37), and a consensus sequence (SEQ ID NO:38), in which each X at each position of SEQ ID NO:38 can be an amino acid (or a conservative amino acid substitution thereof) present at a position in one of SEQ ID NOs:35-37 when optimally aligned with SEQ ID NO:38.

FIG. 13A-13I shows sequences for non-limiting portions of capture agents. Provided are polypeptide sequences for light chain (LC) variable regions for anti-ChE monoclonal antibodies, including (A) antibody 1G (SEQ ID NO:40), (B) antibody 6A (SEQ ID NO:41), (C) antibody 10D (SEQ ID NO:42), (D) antibody AE1 (SEQ ID NO:43), (E) antibody AE2 (SEQ ID NO:44), (F) antibody mAb2 (SEQ ID NO:45), (G) antibody B2_18-5 (SEQ ID NO:46), (H) antibody B2_12-1 (SEQ ID NO:47), and (I) antibody 11D8 (SEQ ID NO:48).

FIG. 14A-14C shows sequence alignments of non-limiting portions of capture agents. Provided are consensus polypeptide sequences for LC variable regions for anti-ChE monoclonal antibodies, including (A) a first consensus sequence (CONS1, SEQ ID NO:59), a second consensus sequence (first CDR or CDR1, SEQ ID NO:60), a third consensus sequence (second CDR or CDR2, SEQ ID NO:61), and a fourth consensus sequence (third CDR or CDR3, SEQ ID NO:62), in which each X at each position of SEQ ID NOs:59-62 is an amino acid (or a conservative amino acid substitution thereof) present at a position in one of SEQ ID NOs:50-58 when optimally aligned with SEQ ID NO:59-62, respectively. Also provided are (B) a further consensus sequence (SEQ ID NO:63), in which each X at each position of SEQ ID NO:63 is an amino acid (or a conservative amino acid substitution thereof) present at a position in one of SEQ ID NOs:50-54 when optimally aligned with SEQ ID NO:63; and (C) another consensus sequence (SEQ ID NO:64), in which each X at each position of SEQ ID NO:64 is an amino acid (or a conservative amino acid substitution thereof) present at a position in one of SEQ ID NOs:55-58 when optimally aligned with SEQ ID NO:64.

FIG. 15 shows a sequence alignment of non-limiting portions of capture agents. Provided are polypeptide sequences for LC constant regions for anti-ChE antibodies, including human immunoglobulin kappa constant (IGKC, SEQ ID NO:70), another human IGKC (SEQ ID NO:71), mouse IGKC (SEQ ID NO:72), another mouse IGKC (SEQ ID NO:73), and a consensus sequence (SEQ ID NO:74), in which each X at each position of SEQ ID NO:74 can be an amino acid (or a conservative amino acid substitution thereof) present at a position in one of SEQ ID NOs:70-73 when optimally aligned with SEQ ID NO:74.

DETAILED DESCRIPTION OF THE INVENTION

The present invention relates to methods, devices, and systems for conducting a cholinesterase inhibition assay. In some embodiments, the assay employs capture and detection methodologies can be employed, e.g., within the method and/or the device, in which the capture agent can be chosen to bind (e.g., selectively and/or specifically bind) the target. In one embodiment, if the target is a cholinesterase, then the capture agent can be another protein that binds cholinesterase. In another embodiment, if the target is an acetylcholinesterase, then the capture agent can be another protein that preferentially binds acetylcholinesterase over other cholinesterases, such as butyrylcholinesterase.

Figure 1A:
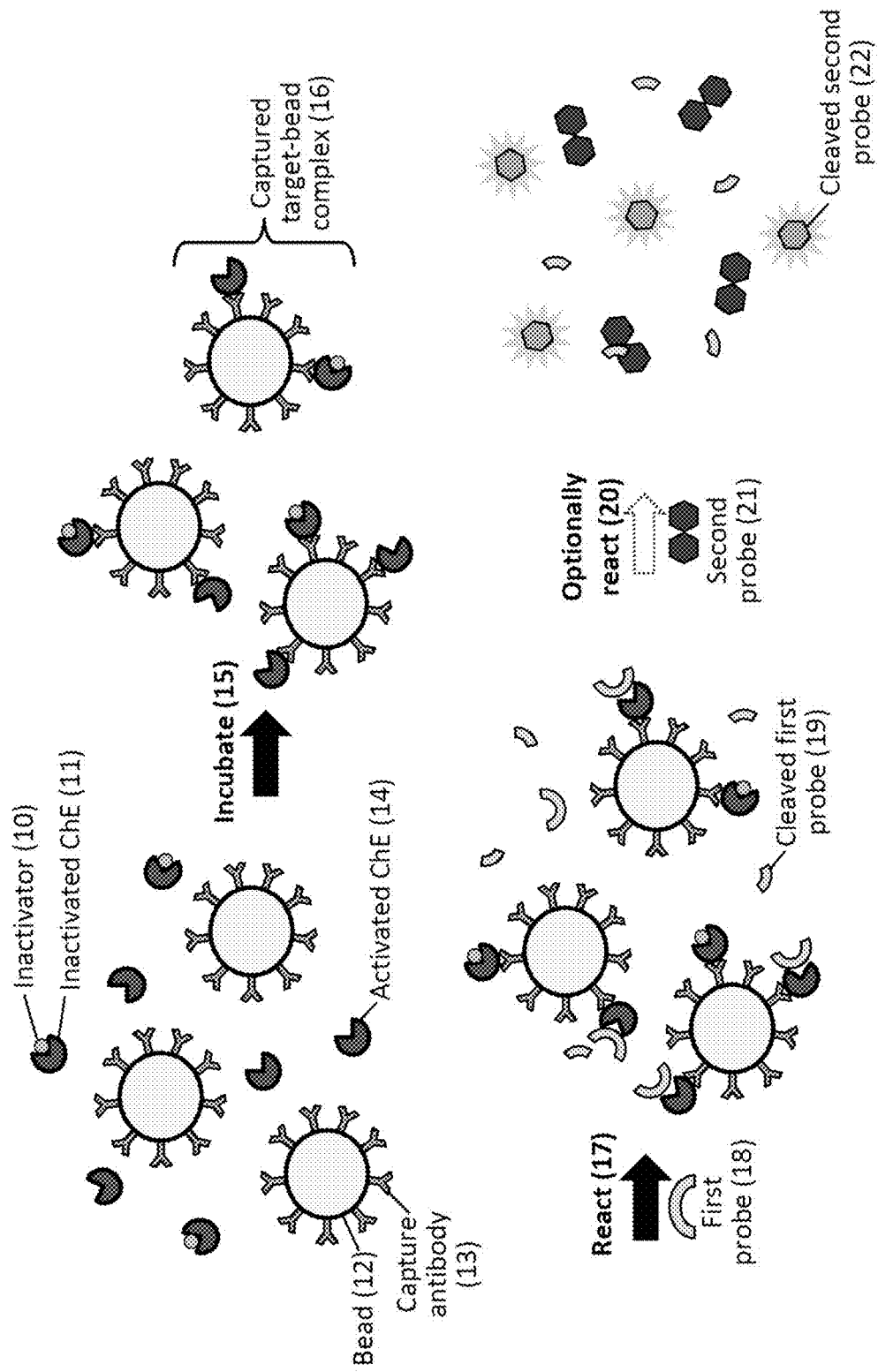
FIG. 1A-1B shows schematics of exemplary detection methodologies. Provided are (A) a first detection methodology for employing a capture antibody 13 to provide a captured target-bead complex 19, which in turn can react 17 with a first probe 18 that can directly or indirectly provide a detectable signal; and (B) another detection methodology for employing a capture antibody 13 to provide a captured target-bead complex 16, which in turn can bind 22 with a detection antibody 23 to provide a detectable target-bead complex 24.

FIG. 1A provides one exemplary capture and detection methodology. As can be seen, the sample can include one or more cholinesterases, in which the cholinesterase (ChE) may be an inactivated ChE 11 bound to an inactivator 10 or an activated ChE 14. To capture ChE (either activated or inactivated), beads are employed, in which the bead 12 includes one or more capture agents (e.g., capture antibodies 13) disposed on a surface of the bead. The amount of capture agents disposed on the surface of the bead can provide a surface concentration that would become saturated upon mixing with a sample. Furthermore, the capture agent can be linked to the bead in any useful manner, e.g., by use of one or more reaction pairs or linkers between the capture agent and the bead.

After incubating 15 the sample with the bead 12, captured target-bead complexes 16 will be formed if the desired target (e.g., ChE, such as acetylcholinesterase (AChE) and/or butyrylcholinesterase (BChE), as well as activated and inactivated forms thereof) is present in the sample. Both such activated and inactivated ChE can be captured, and different detection schemes can be used to determine the presence of activated and/or inactivated ChE. For instance, activated ChE may be detected by employing a probe that measures enzymatic activity, whereas inactivated ChE may be detected by employing a detection antibody that binds to either activated or inactivated ChE. The probe can be selected to preferentially react with certain types of ChE. For instance, certain probes display higher reactivity with AChE versus BChE, as further described herein and provided in FIG. 2A-2D. Depending on the desired target (e.g., activated AChE or activated BChE), a skilled artisan would understand which probe to select for the cholinesterase inhibition assays described herein, as well as how to test probes to determine their selectivity for certain ChEs.

Detection of the captured complex can be accomplished in any useful manner (e.g., by use of a primary antibody conjugate as in a direct assay, by use of a secondary antibody conjugate as in an indirect assay or a capture sandwich assay, by use of an enzymatic substrate or probe, etc.). As can be seen in FIG. 1A, detection can include reacting 17 the complex 16 with a first probe 18 configured to react with activated ChE, thereby resulting in a cleaved first probe 19. In one instance, the cleaved first probe 19 itself can provide a detectable signal. In another instance, the cleaved first probe reacts 20 with a second probe 21, thereby providing a cleaved second probe 22 that provides a detectable signal.

Figure 1B:
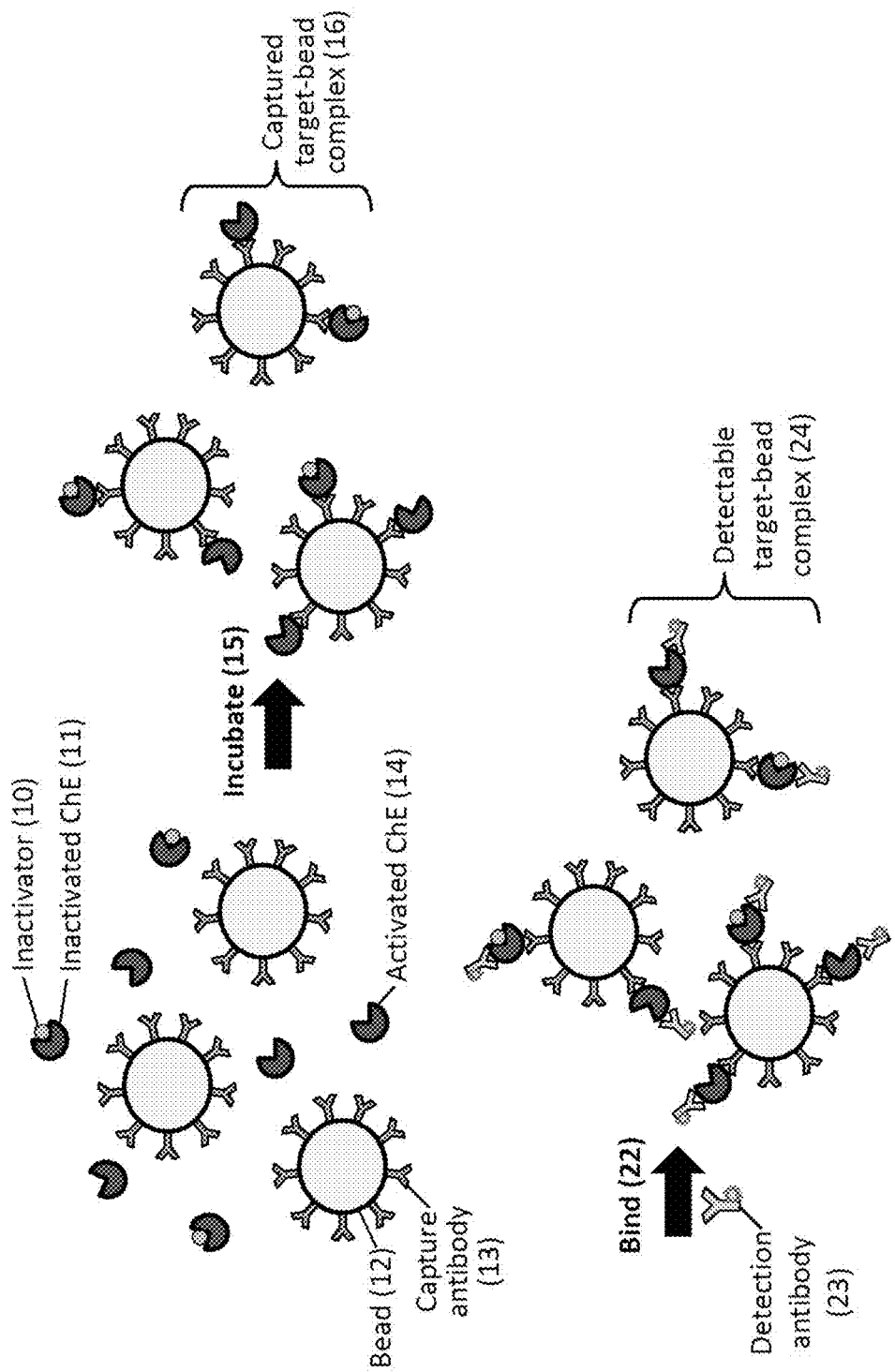

FIG. 1B provides another non-limiting capture and detection methodology. As can be seen, similar to FIG. 1A, the sample can include inactivated ChE 11 and activated ChE 14 that are captured on a bead 12 includes one or more capture agents (e.g., capture antibodies 13) disposed on a surface of the bead. After incubating 15 the sample with the bead 12, captured target-bead complexes 16 will be formed if the desired target is present in the sample. Detection can include binding 22 the complex 16 with a detection agent (e.g., a detection antibody 23) configured to bind the target, thereby resulting in a detectable target-bead complex 24. The detection agent can be configured to bind to inactivated ChE, activated ChE, or both. Furthermore, the detection agent can be selected to bind to a particular type of ChE (e.g., AChE versus BChE, or both).

Each bead within a population can have the same capture agent. In some embodiments, each bead has the same surface concentration of capture agents or different surface concentrations can be employed. Furthermore, each population can have the same capture agent or different capture agents. For each capture agent, the same or different detection agent can be employed. In one instance, each detection agent can be associated with a distinguishable detectable signal, such that a distinct signal (e.g., a particular fluorescence signal at a particular emission wavelength) can distinguish one target from another target.

Figure 3A:
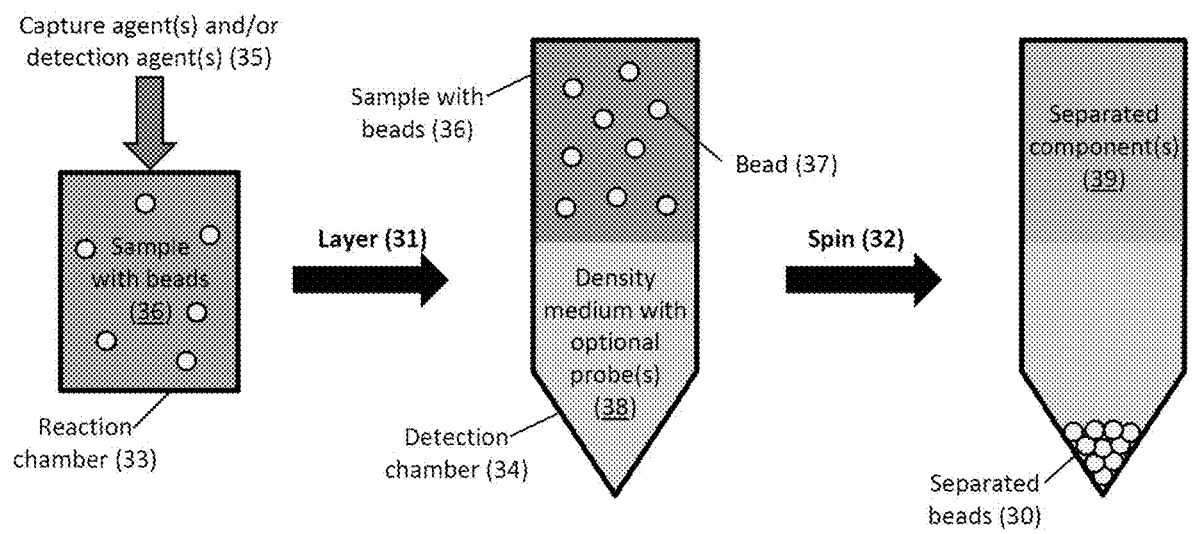
FIG. 3A-3D shows schematics of exemplary methods, assay areas, and systems. Provided are (A) a non-limiting method for conducting a cholinesterase assay by providing a sample 36 for subsequent layering 31 and spinning 32; (B) a non-limiting schematic of an assay area 3000; (C) a non-limiting schematic of another assay area 3100; and (D) an exemplary system including a microfluidic disc 300, a motor module 330, and a detection module 340.

FIG. 3A provides an exemplary method, e.g., for performing an assay. The method can include providing a fluid sample that is being tested for cholinesterase inhibition. In one instance, the fluid sample may be exposed to an organophosphate agent or may be obtained from a subject believed to have been exposed to an organophosphate agent.

The sample can further include one or more beads, which can be provided at any useful step of the assay method or during any useful time while conducting the assay. In one instance, one or more beads are provided immediately after obtaining sample from the subject (e.g., in which the beads are provided in a collection tube employed to draw blood from a subject). In another instance, one or more beads are provided off-chip or on-chip (e.g., within the microfluidic device). In yet another instance, one or more beads are provided prior (e.g., immediately prior) to the layering step (e.g., providing a density medium). In one instance, one or more beads are provided prior (e.g., immediately prior) to the subjecting step (e.g., providing a density medium).

In one non-limiting embodiment, as seen in FIG. 3A, the method can include incubating the sample with one or more capture agents and/or one or more detection agents 35 in, e.g., a reaction chamber 33. The incubating step can include a single stage of incubation with desired agents or multiple stages of incubation with one or more desired agents at each step. In one non-limiting instance, the incubation step includes incubating with one or more capture agents (e.g., attached to a bead or provided as a complex with a bead) and then incubating with one or more detection agents (e.g., for a time sufficient to allow binding of the detection to the target-bead complex). Additional details regarding the incubation step is described herein (see, e.g., FIG. 1A-1B).

After obtaining a sample with beads, the sample can be introduced to a density medium in any useful manner. Thus, in one instance, the method can include layering 31 a sample with beads 36 (e.g., any described herein, including any mixture herein having one or more beads 37) on a density medium 38. Such a layering step can be conducted in any useful assay area, e.g., a detection chamber 34.

Separation can be affected in any useful manner. In one instance, separation can include use of a sedimentation force (e.g., a centrifugal force) to propel particles through the density medium, in which the extent of separation can depend on one or more physical characteristics that affect fluid flow and fluid forces (e.g., such characteristics including particle density, particle size, particle geometry, etc.). In some embodiments, denser components will travel through the density medium, whereas less dense components (e.g., unreacted capture agents, unreacted detection agents, biological components of the sample such as cellular debris, buffer, unreacted agents and reagents, etc.) will remain within a bulk fluid separated from the density medium. In this way, a combination of the beads and the density medium provides effective separation of the targets to be detected. Accordingly, in one non-limiting instance as in FIG. 3A, the method can further include spinning 32 the sample in proximity to the density medium 38, thereby providing one or more separated components 39 and separated beads 30.

The methods herein can be implemented in any useful device (e.g., a microfluidic device). As seen in FIG. 3A, the device can include a chamber (e.g., a reaction chamber 33) configured to store a sample (e.g., a sample with beads 36). The same chamber can be employed for each step, or a different chamber can be employed for at least one step (e.g., each and every step). When the same chamber is employed, then agents can deliver to that chamber (e.g., by way of one or more channels, vias, valves, etc.). When a different chamber is employed, then the agent can be pre-stored within that chamber and/or delivered to that chamber (e.g., by way of one or more channels, vias, valves, etc.).

As also seen in FIG. 3A, the device can include a separate chamber configured to include a density medium, e.g., a detection chamber 34. The detection chamber can be pre-loaded with a density medium. Alternatively, the density chamber can be configured to receive a density medium, e.g., by way of a channel, valve, via, etc. The geometry and volume of the detection chamber can be configured to promote separation, signal detection, etc. In one non-limiting instance, the detection chamber can be tapered at one end (e.g., located in proximity to a periphery of a microfluidic disc).

Figure 3B:
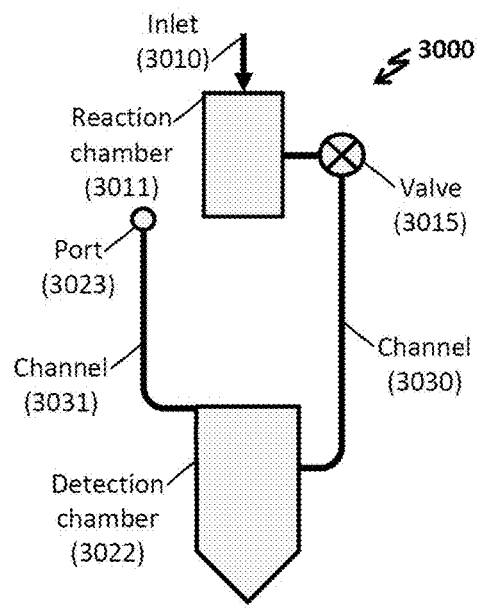
Figure 3C:
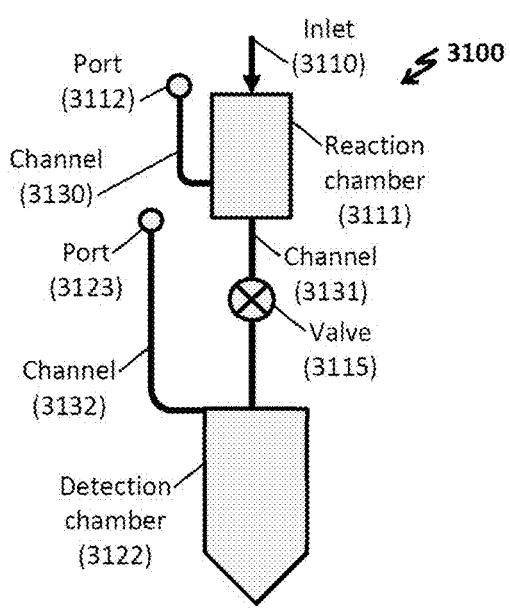

Any useful structure can be provided in the device. In one non-limiting instance, the device can include an assay area, which can be any useful area that facilitates one or more reaction(s), separation(s), and/or detection of a desired target. FIG. 3B-3C provides exemplary structures for an assay area 3000,3100. In some embodiments as in FIG. 3B, the assay area 3000 includes a reaction chamber 3011 in fluidic communication with a detection chamber 3022. The chambers can be in fluidic communication with any other fluidic structures, such as a valve to control fluidic flow (e.g., direction of flow, extent of flow, etc.), an inlet (e.g., configured to introduce a sample, an agent, etc.), a port (e.g., configured to release pressure or fluid overflow), and/or a channel (e.g., to provide fluidic communication).

As seen in FIG. 3B, in one embodiment, the assay area 3000 includes an inlet 3010 in fluidic communication with the reaction chamber 3011, where the inlet is configured to deliver a sample to the reaction chamber; a first channel 3030 to provide fluidic communication between the reaction chamber 3011 and the detection chamber 3022, where a valve 3015 is optionally disposed in fluidic communication with the first channel 3030 to control fluid flow; and a port 3023 to provide release of pressure within any chamber, in which a second channel 3031 provides fluidic communication between the detection chamber 3022 and the port 3023.

As seen in FIG. 3C, in one embodiment, the assay area 3100 includes an inlet 3110 in fluidic communication with the reaction chamber 3111, where the inlet is configured to deliver a sample to the reaction chamber; a first port 3112 to provide release of pressure within any chamber, in which a first channel 3130 provides fluidic communication between the reaction chamber 3111 and the port 3112; a second channel 3131 to provide fluidic communication between the reaction chamber 3111 and the detection chamber 3122, where a valve 3115 is optionally disposed in fluidic communication with the second channel 3131 to control fluid flow; and a second port 3123 to provide release of pressure within any chamber, in which a third channel 3132 provides fluidic communication between the detection chamber 3122 and the port 3123.

Figure 3D:
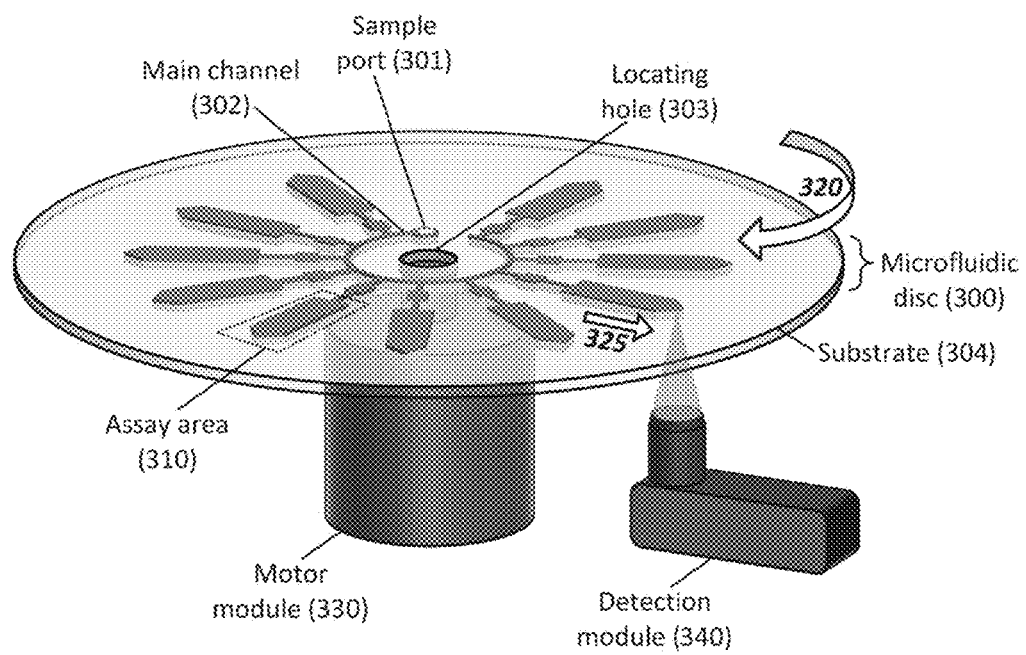

The present invention also encompasses a device, which can be optionally employed with any useful system (e.g., any described herein). In one non-limiting instance, as seen in FIG. 3D, the device is a microfluidic disc 300 including a substrate 304 having at least one sample port 301, e.g., configured to receive a sample, including a mixture including a sample portion. Any useful fluidic structure can be employed to provide fluidic communication, including a main channel 302 disposed within the substrate 304 and in fluidic communication with the sample port 301. The main channel 302, in turn, can be in fluidic communication with any useful assay area 310 (e.g., any described herein).

The device can be used in conjunction with a system. In one embodiment, as in FIG. 3D, the device includes a locating hole 303 configured to be coupled to a portion of a motor module 330. The motor module, in turn, can be configured to spin 320 the device, thereby eliciting a sedimentation force 325 within the assay area 310. The system can further include a detection module 340 configured to detect a signal from one or more detection agents present in the assay area.

Cholinesterases and Probes

The present invention relates to methods and systems for detecting inhibition of a cholinesterase. Exemplary cholinesterases include acetylcholinesterase (AChE) or butyrylcholinesterase (BChE). Yet other cholinesterases include those in FIG. 8A-8G and FIG. 9A-9C (SEQ ID NOs:2-8, 10, and 11).

In some embodiments, the cholinesterase includes or is a polypeptide sequence having at least 90% sequence identity to SEQ ID NO:10 or SEQ ID NO:11:

(SEQ ID NO: 10)
EX$_2$X$_3$X$_4$X$_5$X$_6$X$_7$X$_8$X$_9$X$_{10}$X$_{11}$X$_{12}$X$_{13}$X$_{14}$GX$_{16}$X$_{17}$RGX$_{20}$X$_{21}$X$_{22}$X$_{23}$X$_{24}$X$_{25}$X$_{26}$GX$_{28}$VX$_{30}$AFLGIP

X$_{37}$AX$_{39}$PPX$_{42}$GX$_{44}$X$_{45}$RFX$_{48}$X$_{49}$PX$_{51}$X$_{52}$X$_{53}$X$_{54}$X$_{55}$WX$_{57}$X$_{58}$X$_{59}$X$_{60}$X$_{61}$ATX$_{64}$X$_{65}$X$_{66}$X$_{67}$X$_{68}$CX$_{70}$

QX$_{72}$X$_{73}$DX$_{75}$X$_{76}$X$_{77}$PGFX$_{81}$GX$_{83}$EMWNPNX$_{90}$X$_{91}$LSEDCLYLNVWX$_{103}$PX$_{105}$PX$_{107}$PX$_{109}$X$_{110}$

X$_{111}$TX$_{113}$VX$_{115}$X$_{116}$WIYGGX$_{122}$FX$_{124}$X$_{125}$GX$_{127}$X$_{128}$SLX$_{131}$VYDGX$_{136}$FLX$_{139}$X$_{140}$X$_{141}$EX$_{143}$

X$_{144}$X$_{145}$X$_{146}$VSMNYRVGX$_{155}$X$_{156}$GFLAX$_{161}$PGX$_{164}$X$_{165}$X$_{166}$APGNX$_{171}$GLX$_{174}$DQX$_{177}$LALQWV

QX$_{185}$NX$_{187}$AAFGGX$_{193}$PX$_{195}$SX$_{197}$TX$_{199}$FGESAGAASVX$_{210}$X$_{211}$HX$_{213}$LX$_{215}$X$_{216}$X$_{217}$SX$_{219}$

X$_{220}$LFX$_{223}$RAX$_{226}$LX$_{228}$SGX$_{231}$X$_{232}$NX$_{234}$PWAX$_{238}$X$_{239}$X$_{240}$X$_{241}$X$_{242}$EARX$_{246}$RX$_{248}$X$_{249}$X$_{250}$

LAX$_{253}$X$_{254}$X$_{255}$GCX$_{258}$X$_{259}$X$_{260}$X$_{261}$X$_{262}$X$_{263}$X$_{264}$NX$_{266}$X$_{267}$EX$_{269}$X$_{270}$X$_{271}$CLRX$_{275}$X$_{276}$X$_{277}$

X$_{278}$QX$_{280}$X$_{281}$X$_{282}$X$_{283}$X$_{284}$EX$_{286}$X$_{287}$VX$_{289}$PX$_{291}$X$_{292}$X$_{293}$X$_{294}$X$_{295}$X$_{296}$X$_{297}$X$_{298}$FX$_{300}$PX$_{302}$

VDGDFLX$_{309}$DX$_{311}$PX$_{313}$X$_{314}$LX$_{316}$X$_{317}$X$_{318}$GX$_{320}$X$_{321}$X$_{322}$X$_{323}$X$_{324}$QX$_{326}$LVGVX$_{331}$KDEGX$_{336}$

X$_{337}$FLVYGX$_{343}$PGFSKDNX$_{351}$SX$_{353}$IX$_{355}$RX$_{357}$X$_{358}$FX$_{360}$X$_{361}$GX$_{363}$X$_{364}$X$_{365}$X$_{366}$X$_{367}$PX$_{369}$

X$_{370}$SX$_{372}$X$_{373}$X$_{374}$X$_{375}$EX$_{377}$X$_{378}$X$_{379}$X$_{380}$X$_{381}$YX$_{383}$DWX$_{386}$X$_{387}$X$_{388}$X$_{389}$X$_{390}$X$_{391}$X$_{392}$X$_{393}$

X$_{394}$RX$_{396}$AX$_{398}$X$_{399}$X$_{400}$VX$_{402}$GDX$_{405}$NX$_{407}$X$_{408}$CPX$_{411}$X$_{412}$X$_{413}$X$_{414}$X$_{415}$X$_{416}$X$_{417}$X$_{418}$X$_{419}$

X$_{420}$X$_{421}$X$_{422}$X$_{423}$X$_{424}$X$_{425}$X$_{426}$X$_{427}$YX$_{429}$FEHRX$_{434}$SX$_{436}$LX$_{438}$WPX$_{441}$WMGVX$_{446}$HGYEIEF

X$_{454}$FGX$_{457}$PLX$_{460}$X$_{461}$X$_{462}$X$_{463}$NYTX$_{467}$X$_{468}$EX$_{470}$X$_{471}$X$_{472}$X$_{473}$X$_{474}$X$_{475}$X$_{476}$X$_{477}$X$_{478}$X$_{479}$W

X$_{481}$NFAX$_{485}$X$_{486}$GX$_{488}$PNX$_{491}$X$_{492}$X$_{493}$X$_{494}$X$_{495}$X$_{496}$X$_{497}$X$_{498}$X$_{499}$WPX$_{502}$X$_{503}$X$_{504}$X$_{505}$X$_{506}$

X$_{507}$QX$_{509}$YX$_{511}$X$_{512}$LX$_{514}$X$_{515}$X$_{516}$X$_{517}$X$_{518}$X$_{519}$X$_{520}$X$_{521}$X$_{522}$X$_{523}$LRAX$_{527}$X$_{528}$CX$_{530}$FWX$_{533}$

X$_{534}$FX$_{536}$PKX$_{539}$LX$_{541}$X$_{542}$TX$_{544}$X$_{545}$X$_{546}$DEX$_{549}$EX$_{551}$X$_{552}$WKAX$_{556}$FHRWX$_{561}$X$_{562}$YMX$_{565}$

X$_{566}$WX$_{568}$NQFX$_{572}$DX$_{574}$X$_{575}$SKX$_{578}$X$_{579}$X$_{580}$CX$_{582}$X$_{583}$L or (SEQ ID NO: 11)
EX$_2$X$_3$X$_4$X$_5$X$_6$X$_7$X$_8$X$_9$X$_{10}$X$_{11}$X$_{12}$X$_{13}$X$_{14}$GX$_{16}$X$_{17}$RGX$_{20}$X$_{21}$X$_{22}$X$_{23}$X$_{24}$X$_{25}$X$_{26}$GX$_{28}$VX$_{30}$AFLGIP

X$_{37}$AX$_{39}$PPX$_{42}$GX$_{44}$X$_{45}$RFX$_{48}$X$_{49}$PX$_{51}$X$_{52}$X$_{53}$X$_{54}$X$_{55}$WX$_{57}$X$_{58}$X$_{59}$X$_{60}$X$_{61}$ATX$_{64}$X$_{65}$X$_{66}$X$_{67}$X$_{68}$CX$_{70}$

QX$_{72}$X$_{73}$DX$_{75}$X$_{76}$X$_{77}$PGFX$_{81}$GX$_{83}$EMWNPNX$_{90}$X$_{91}$LSEDCLYLNVWX$_{103}$PX$_{105}$PX$_{107}$PX$_{109}$X$_{110}$

X$_{111}$TX$_{113}$VX$_{115}$X$_{116}$WIYGGX$_{122}$FX$_{124}$X$_{125}$GX$_{127}$X$_{128}$SLX$_{131}$VYDGX$_{136}$FLX$_{139}$X$_{140}$X$_{141}$EX$_{143}$

X$_{144}$X$_{145}$X$_{146}$VSMNYRVGX$_{155}$X$_{156}$GFLAX$_{161}$PGX$_{164}$X$_{165}$X$_{166}$APGNX$_{171}$GLX$_{174}$DQX$_{177}$LALQWV

QX$_{185}$NX$_{187}$AAFGGX$_{193}$PX$_{195}$SX$_{197}$TX$_{199}$FGESAGAASVX$_{210}$X$_{211}$HX$_{213}$LX$_{215}$X$_{216}$X$_{217}$SX$_{219}$

X$_{220}$LFX$_{223}$RAX$_{226}$LX$_{228}$SGX$_{231}$X$_{232}$NX$_{234}$PWAX$_{238}$X$_{239}$X$_{240}$X$_{241}$X$_{242}$EARX$_{246}$RX$_{248}$X$_{249}$X$_{250}$

LAX$_{253}$X$_{254}$X$_{255}$GCX$_{258}$X$_{259}$X$_{260}$X$_{261}$X$_{262}$X$_{263}$X$_{264}$NX$_{266}$X$_{267}$EX$_{269}$X$_{270}$X$_{271}$CLRX$_{275}$X$_{276}$X$_{277}$

X$_{278}$QX$_{280}$X$_{281}$X$_{282}$X$_{283}$X$_{284}$EX$_{286}$X$_{287}$VX$_{289}$PX$_{291}$X$_{292}$X$_{293}$X$_{294}$X$_{295}$X$_{296}$X$_{297}$X$_{298}$FX$_{300}$PX$_{302}$

VDGDFLX$_{309}$DX$_{311}$PX$_{313}$X$_{314}$LX$_{316}$X$_{317}$X$_{318}$GX$_{320}$X$_{321}$X$_{322}$X$_{323}$X$_{324}$QX$_{326}$LVGVX$_{331}$KDEGX$_{336}$

X$_{337}$FLVYGX$_{343}$PGFSKDNX$_{351}$SX$_{353}$IX$_{355}$RX$_{357}$X$_{358}$FX$_{360}$X$_{361}$GX$_{363}$X$_{364}$X$_{365}$X$_{366}$X$_{367}$PX$_{369}$

X$_{370}$SX$_{372}$X$_{373}$X$_{374}$X$_{375}$EX$_{377}$X$_{378}$X$_{379}$X$_{380}$X$_{381}$YX$_{383}$DWX$_{386}$X$_{387}$X$_{388}$X$_{389}$X$_{390}$X$_{391}$X$_{392}$X$_{393}$

X$_{394}$RX$_{396}$AX$_{398}$X$_{399}$X$_{400}$VX$_{402}$GDX$_{405}$NX$_{407}$X$_{408}$CPX$_{411}$X$_{412}$X$_{413}$X$_{414}$X$_{415}$X$_{416}$X$_{417}$X$_{418}$X$_{419}$

X$_{420}$X$_{421}$X$_{422}$X$_{423}$X$_{424}$X$_{425}$X$_{426}$X$_{427}$YX$_{429}$FEHRX$_{434}$SX$_{436}$LX$_{438}$WPX$_{441}$WMGVX$_{446}$HGYEIEF

X$_{454}$EGX$_{457}$PLX$_{460}$X$_{461}$X$_{462}$X$_{463}$NYTX$_{467}$X$_{468}$EX$_{470}$X$_{471}$X$_{472}$X$_{473}$X$_{474}$X$_{475}$X$_{476}$X$_{477}$X$_{478}$X$_{479}$

WX$_{481}$NFAX$_{485}$X$_{486}$GX$_{488}$PNX$_{491}$X$_{492}$X$_{493}$X$_{494}$X$_{495}$X$_{496}$X$_{497}$X$_{498}$X$_{499}$WPX$_{502}$X$_{503}$X$_{504}$X$_{505}$X$_{506}$

-continued $X_{507}QX_{509}YX_{511}X_{512}LX_{514}X_{515}X_{516}X_{517}X_{518}X_{519}X_{520}X_{521}X_{522}X_{523}LRAX_{527}X_{528}CX_{530}FWX_{533}$ $X_{534}FX_{536}PKX_{539}LX_{541}X_{542}TX_{544}X_{545}X_{546}DEX_{549}EX_{551}$, wherein:
  each of $X_2$, $X_{260}$, and $X_{261}$ is G or absent;
  each of $X_3$, $X_4$, $X_5$, $X_6$, $X_{113}$, $X_{258}$, $X_{259}$, $X_{277}$, $X_{278}$, $X_{388}$, $X_{495}$, and $X_{541}$ is A, D, E, P, R, S, T, or absent;
  each of $X_7$, $X_{39}$, $X_{51}$, $X_{61}$, $X_{166}$, $X_{193}$, $X_{228}$, $X_{317}$, $X_{351}$, $X_{358}$, $X_{389}$, $X_{413}$, $X_{514}$, and $X_{552}$ is D, E, N, or Q;
  each of $X_8$, $X_{25}$, $X_{294}$, $X_{295}$, $X_{297}$, $X_{321}$, $X_{367}$, $X_{380}$, $X_{391}$, $X_{407}$, $X_{414}$, $X_{418}$, $X_{427}$, $X_{429}$, $X_{446}$, $X_{472}$, $X_{511}$, and $X_{536}$ is A, V, I, L, M, P, Y, or F;
  each of $X_9$, $X_{10}$, $X_{17}$, $X_{22}$, $X_{42}$, $X_{59}$, $X_{115}$, $X_{116}$, $X_{141}$, $X_{145}$, $X_{146}$, $X_{171}$, $X_{187}$, $X_{197}$, $X_{199}$, $X_{211}$, $X_{213}$, $X_{226}$, $X_{234}$, $X_{269}$, $X_{270}$, $X_{281}$, $X_{282}$, $X_{289}$, $X_{300}$, $X_{316}$, $X_{326}$, $X_{343}$, $X_{353}$, $X_{363}$, $X_{365}$, $X_{370}$, $X_{374}$, $X_{378}$, $X_{379}$, $X_{386}$, $X_{398}$, $X_{402}$, $X_{408}$, $X_{411}$, $X_{412}$, $X_{425}$, $X_{454}$, $X_{457}$, $X_{476}$, $X_{477}$, $X_{520}$, $X_{539}$, $X_{542}$, $X_{546}$, and $X_{565}$ is G, A, V, I, L, or M (e.g., G, A, V, I, or L; or A, V, I, or L);
  each of $X_{11}$, $X_{20}$, $X_{23}$, $X_{48}$, $X_{109}$, $X_{111}$, $X_{195}$, $X_{216}$, $X_{241}$, $X_{267}$, $X_{271}$, $X_{383}$, $X_{467}$, $X_{502}$, and $X_{518}$ is A, V, I, L, R, H, K, S, T, P, C, or M;
  each of $X_{12}$, $X_{24}$, $X_{68}$, $X_{73}$, $X_{76}$, $X_{103}$, $X_{127}$, $X_{128}$, $X_{139}$, $X_{144}$, $X_{155}$, $X_{231}$, $X_{238}$, $X_{248}$, $X_{249}$, $X_{255}$, $X_{262}$, $X_{302}$, $X_{314}$, $X_{318}$, $X_{324}$, $X_{377}$, $X_{415}$, $X_{419}$, $X_{434}$, $X_{471}$, $X_{473}$, $X_{481}$, $X_{497}$, $X_{505}$, $X_{515}$, $X_{549}$, and $X_{582}$ is A, V, I, L, S, or T;
  each of $X_{13}$, $X_{26}$, $X_{107}$, $X_{136}$, $X_{143}$, $X_{253}$, $X_{263}$, $X_{276}$, $X_{416}$, $X_{417}$, $X_{485}$, and $X_{523}$ is G, R, H, or K;
  each of $X_{14}$, $X_{67}$, $X_{75}$, $X_{110}$, $X_{122}$, $X_{164}$, $X_{291}$, $X_{486}$, and $X_{575}$ is G, N, Q, F, Y, W, S, or T;
  each of $X_{16}$, $X_{21}$, $X_{54}$, $X_{140}$, $X_{177}$, $X_{246}$, $X_{284}$, $X_{298}$, $X_{322}$, $X_{496}$, and $X_{568}$ is N, Q, R, H, K, S, or T;
  each of $X_{28}$, $X_{52}$, $X_{57}$, $X_{220}$, $X_{232}$, $X_{438}$, $X_{492}$, $X_{498}$, and $X_{517}$ is G, P, F, S, or T;
  each of $X_{30}$, $X_{83}$, $X_{125}$, $X_{210}$, $X_{293}$, $X_{309}$, $X_{336}$, $X_{355}$, and $X_{512}$ is G, S, or T;
  each of $X_{37}$, $X_{65}$, $X_{77}$, $X_{426}$, and $X_{503}$ is F, Y, or W;
  each of $X_{44}$, $X_{49}$, $X_{55}$, $X_{90}$, $X_{165}$, $X_{223}$, $X_{240}$, $X_{296}$, $X_{436}$, $X_{461}$, $X_{462}$, $X_{475}$, $X_{504}$, $X_{509}$, $X_{522}$, and $X_{580}$ is G, P, R, H, K, S, or T;
  each of $X_{45}$, $X_{53}$, $X_{357}$, and $X_{375}$ is A, V, I, L, R, H, or K;
  each of $X_{58}$, $X_{91}$, $X_{264}$, $X_{266}$, $X_{292}$, $X_{396}$, $X_{460}$, $X_{491}$, $X_{544}$, $X_{556}$, and $X_{579}$ is G, D, or E;
  each of $X_{60}$, $X_{72}$, $X_{124}$, $X_{219}$, $X_{286}$, $X_{287}$, $X_{337}$, $X_{381}$, $X_{405}$, $X_{551}$, and $X_{574}$ is A, V, I, L, F, Y, W, N, Q, R, H, or K;
  each of $X_{64}$, $X_{66}$, $X_{239}$, $X_{250}$, $X_{275}$, $X_{360}$, $X_{423}$, $X_{506}$, $X_{528}$, $X_{533}$, and $X_{534}$ is G, A, V, I, L, N, Q, R, H, K, S, or T;
  each of $X_{70}$, $X_{215}$, and $X_{311}$ is F, Y, W, M, C, S, or T;
  each of $X_{81}$, $X_{280}$, $X_{283}$, $X_{320}$, $X_{331}$, $X_{361}$, $X_{400}$, $X_{420}$, $X_{441}$, $X_{463}$, $X_{468}$, $X_{507}$, $X_{519}$, $X_{530}$, and $X_{583}$ is A, V, I, L, D, E, N, Q, R, H, or K;
  each of $X_{105}$, $X_{156}$, $X_{161}$, $X_{174}$, $X_{254}$, $X_{373}$, and $X_{394}$ is A, V, I, L, F, Y, W, S, or T;
  each of $X_{131}$, $X_{185}$, $X_{217}$, $X_{313}$, $X_{323}$, $X_{364}$, $X_{369}$, $X_{372}$, $X_{387}$, $X_{424}$, $X_{470}$, $X_{474}$, $X_{478}$, $X_{488}$, $X_{493}$, $X_{494}$, $X_{516}$, $X_{527}$, $X_{566}$, and $X_{578}$ is G, D, E, P, N, Q, R, H, or K;
  each of $X_{242}$, $X_{366}$, and $X_{422}$ is G, D, E, F, Y, or W;
  each of $X_{561}$ and $X_{562}$ is N, Q, S, or T;
  each of $X_{390}$, $X_{392}$, $X_{393}$, $X_{399}$, $X_{421}$, $X_{479}$, $X_{499}$, $X_{521}$, and $X_{545}$ is any amino acid (e.g., G, A, V, I, L, D, E, N, Q, R, H, K, S, or T; D, E, N, Q, R, H, K, S, or T; G, A, V, I, L, D, E, S, or T; A, V, I, L, M, N, Q, F, Y, or W; F, Y, W, R, H, K, S, or T; A, V, I, L, M, N, Q, R, H, K, S, or T; A, V, I, L, M, F, Y, W, N, Q, R, H, or K; or D, E, N, Q, S, or T); and
  $X_{572}$ is N, Q, or absent.

In other embodiments, each X in SEQ ID NO:10 can be an amino acid (or a conservative amino acid substitution thereof) in any one of SEQ ID NOs:2-8 when any one of the sequences in SEQ ID NOs:2-8 is used as a reference sequence to be optimally aligned with SEQ ID NO:10.

In yet other embodiments, each X in SEQ ID NO:11 can be an amino acid (or a conservative amino acid substitution thereof) in any one of SEQ ID NOs:2-8 when any one of the sequences in SEQ ID NOs:2-8 is used as a reference sequence to be optimally aligned with SEQ ID NO:11.

Upon exposure to an inactivator, a cholinesterase exhibits diminished enzymatic activity (e.g., reduced ester cleavage). Such diminished activity can be assessed by employing a probe having a chemical moiety capable of being cleaved by the cholinesterase.

Exemplary probes can include a cationic moiety. In some embodiments, the cationic moiety is an ammonium moiety, such as $-NR^{n1}R^{n2}R^{n3}$, wherein each of $R^{n1}$, $R^{n2}$, and $R^{n3}$ is, independently, H, an optionally substituted alkyl (e.g., $C_{1-6}$ alkyl), or a protecting group (e.g., an N-protecting group).

Furthermore, probes can optionally include an ester-like moiety. In some embodiments, the ester-like moiety includes an ester moiety or a thioester moiety, e.g., $-X-C(O)-$, in which X is O or S. In yet other embodiments, the ester-like moiety is an ester moiety or a thioester moiety, e.g., $-X-C(O)-R^1$, in which X is O or S and $R^1$ is an optionally substituted alkyl, an optionally substituted aryl, an optionally substituted alkaryl, or an optionally substituted heterocyclyl.

Figure 2A:
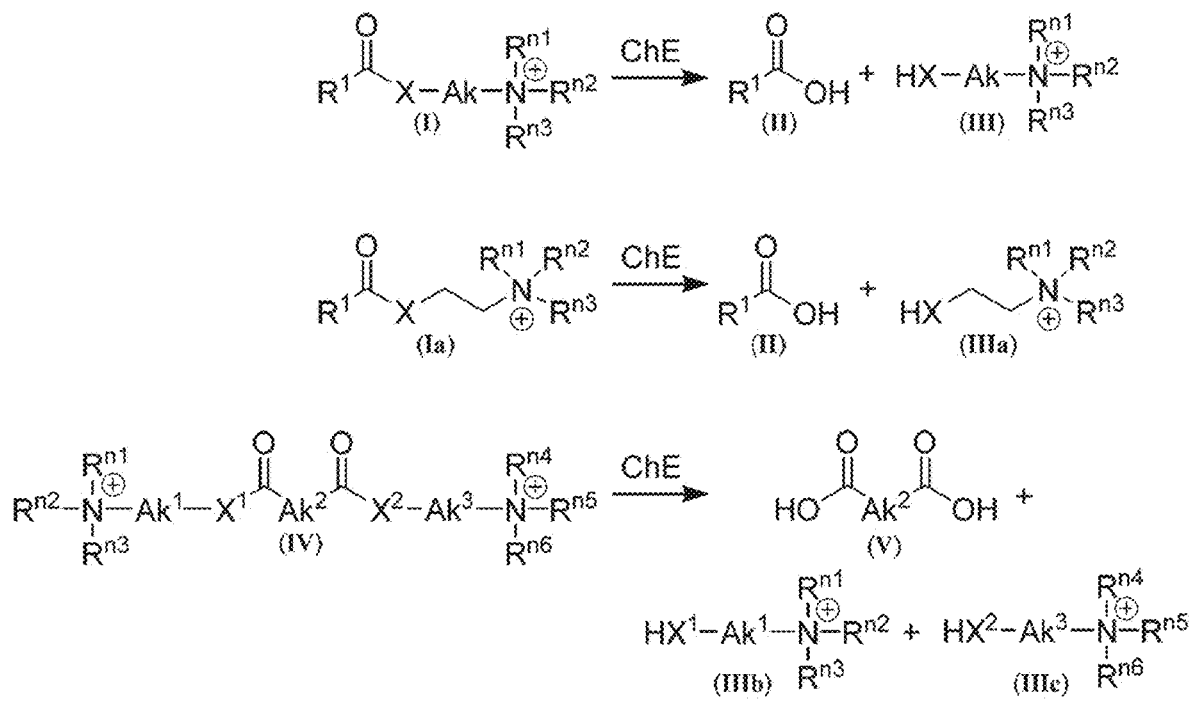
FIG. 2A-2D shows schematics of exemplary probes for detecting cholinesterase activity. Provided are (A) non-limiting examples of probes having a compound of formula (I), (Ia), (IV), or a salt thereof, which provides an alkyl choline derivative (compounds of formula (III), (IIIa), (IIIb), or (IIIc), or salts thereof); (B) non-limiting examples of probes having a compound of formula (VI), (VIa), or a salt thereof, which provides an aryl choline derivative (compounds of formula (VII), (VIIa), or salts thereof); (C) a non-limiting example of a further probe that can be used in the presence of an alkyl choline derivative or an aryl choline derivative, such as a probe having a compound of formula (VIII) or a salt thereof, which provides a thiol-based compound (compound (IX)) capable of providing a detectable signal; and (D) yet another non-limiting example of a further probe (a non-fluorescent substrate S) that can be used in the presence of an alkyl choline derivative or an aryl choline derivative treated with a choline oxidase (ChOx) to provide a compound capable of providing a detectable signal (a fluorescent substrate S*).

FIG. 2A provides an exemplary probe having a structure of formula (I) or a salt thereof, wherein Ak is an optionally substituted alkylene (e.g., $C_{1-6}$ alkylene), an optionally substituted heteroalkylene (e.g., $C_{1-6}$ heteroalkylene), or an optionally substituted arylene (e.g., $C_{4-12}$ arylene); X is O or S; $R^1$ is an optionally substituted alkyl (e.g., $C_{1-6}$ alkyl), an optionally substituted aryl (e.g., $C_{4-12}$ aryl), an optionally substituted alkaryl (e.g., $C_{1-6}$ alk-$C_{4-12}$ aryl), or an optionally substituted heterocyclyl; and each of $R^{n1}$, $R^{n2}$, and $R^{n3}$ is, independently, H, an optionally substituted alkyl (e.g., $C_{1-6}$ alkyl), or a protecting group (e.g., an N-protecting group). Cleavage of such a probe can release an acid derivative having a structure of formula (II) or a salt thereof, as well as a choline derivative having a structure of formula (III) or a salt thereof.

In particular embodiments, the probe has a structure of formula (Ia) or a salt thereof, wherein X is O or S; $R^1$ is an optionally substituted alkyl (e.g., $C_{1-6}$ alkyl), an optionally substituted aryl (e.g., $C_{4-12}$ aryl), an optionally substituted alkaryl (e.g., $C_{1-6}$ alk-$C_{4-12}$ aryl), or an optionally substituted heterocyclyl; and each of $R^{n1}$, $R^{n2}$, and $R^{n3}$ is, independently, H, an optionally substituted alkyl (e.g., $C_{1-6}$ alkyl), or a protecting group (e.g., an N-protecting group). Cleavage of this probe releases an acid derivative having a structure of formula (II) or a salt thereof, as well as a choline derivative having a structure of formula (IIIa) or a salt thereof.

The probe can include a plurality of cationic moieties. As seen in FIG. 2A, the probe can have a structure of formula (IV) or a salt thereof, wherein each of $Ak^1$, $Ak^2$, and $Ak^3$ is, independently, an optionally substituted alkylene (e.g., $C_{1-6}$ alkylene), an optionally substituted heteroalkylene (e.g., $C_{1-6}$ heteroalkylene), or an optionally substituted arylene (e.g., $C_{4-12}$ arylene); each of $X^1$ and $X^2$ is, independently, O or S; $R^1$ is an optionally substituted alkyl (e.g., $C_{1-6}$ alkyl), an optionally substituted aryl (e.g., $C_{4-12}$ aryl), an optionally substituted alkaryl (e.g., $C_{1-6}$ alk-$C_{4-12}$ aryl), or an optionally substituted heterocyclyl; and each of $R^{n1}$, $R^{n2}$, $R^{n3}$, $R^{n4}$, $R^{n5}$, and $R^{n6}$ is, independently, H, an optionally substituted alkyl (e.g., $C_{1-6}$ alkyl), or a protecting group (e.g., an N-protecting group). Cleavage of such a probe can release a diacid derivative having a structure of formula (V) or a salt thereof, as well as two choline derivatives having a structure of formula (IIIb) or (IIIc) or a salt thereof.

Figure 2B:
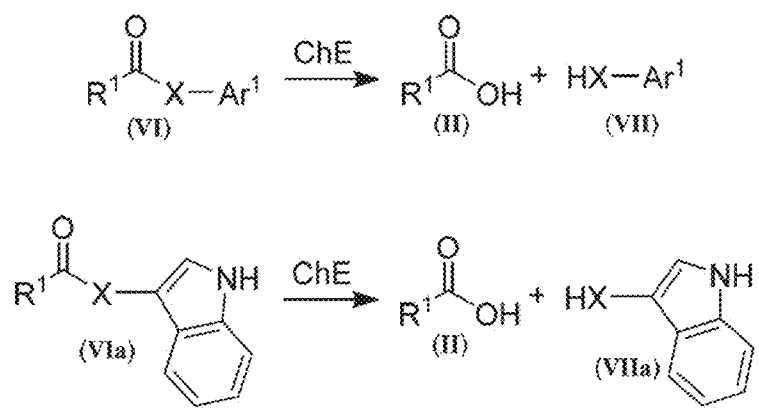

Yet other exemplary probes can include an organic moiety that emits a detectable signal upon cleavage of the ester moiety or thioester moiety. Exemplary organic moieties can include chromophores, fluorophores, and bicyclic or multi-cyclic moieties. FIG. 2B provides an exemplary probe having a structure of formula (VI) or a salt thereof, wherein $Ar^1$ is an optionally substituted aryl (e.g., $C_{4-12}$ aryl), an optionally substituted alkaryl (e.g., $C_{1-6}$ alk-$C_{4-12}$ aryl), or an optionally substituted heterocyclyl; X is O or S; and $R^1$ is an optionally substituted alkyl (e.g., $C_{1-6}$ alkyl), an optionally substituted aryl (e.g., $C_{4-12}$ aryl), an optionally substituted alkaryl (e.g., $C_{1-6}$ alk-$C_{4-12}$ aryl), or an optionally substituted heterocyclyl. Cleavage of such a probe can release an acid derivative having a structure of formula (II) or a salt thereof, as well as an alcohol or thiol derivative having a structure of formula (VII) or a salt thereof.

In other embodiments, the probe has a structure of formula (VIa) or a salt thereof, wherein X is O or S; and $R^1$ is an optionally substituted alkyl (e.g., $C_{1-6}$ alkyl), an optionally substituted aryl (e.g., $C_{4-12}$ aryl), an optionally substituted alkaryl (e.g., $C_{1-6}$ alk-$C_{4-12}$ aryl), or an optionally substituted heterocyclyl. Cleavage of this probe releases an acid derivative having a structure of formula (II) or a salt thereof, as well as an alcohol or thiol derivative having a structure of formula (VIIa) or a salt thereof, in which the released heterocyclyl provides a detectable signal.

Figure 2C:
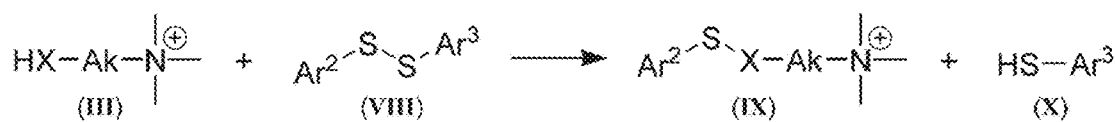

Upon reaction with an activated cholinesterase, choline or a derivative thereof is generally released. In particular embodiments, the released choline derivative is further reacted with an agent to provide, directly or indirectly, a detectable signal. As seen in FIG. 2C, a choline derivative having a structure of formula (III) or a salt thereof can be reacted with a second probe having a structure of formula (VIII) or a salt thereof. This second probe, in turn, is cleaved to provide a detectable agent having a structure of formula (IX) or a salt thereof, as well as a released thiol having a structure of formula (X).

Figure 2D:
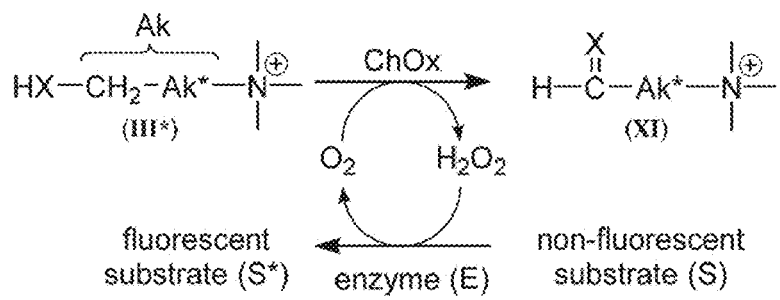

The released choline derivative can be further treated and then reacted with an agent to provide a detectable signal. For instance, the released choline derivative can be treated with an oxidase, thereby releasing hydrogen peroxide ($H_2O_2$) as a byproduct, which in turn can catalyze another reaction that produces a detectable signal. As seen in FIG. 2D, a released choline derivative having a structure of formula (III*) or a salt thereof (in which —$CH_2$-Ak*-, together, forms Ak) is treated with choline oxidase (ChOx) to provide an oxidized choline derivative having a structure of formula (XI) or a salt thereof, thereby releasing $H_2O_2$ as a byproduct. This released hydrogen peroxide can then be used to catalyze another reaction that produces a detectable signal, such as a horseradish peroxidase (HRP) reaction. In this reaction, HRP, in conjunction with $H_2O_2$, catalyzes a reaction to convert a non-fluorescent substrate (S) to a fluorescent substrate (S*).

Yet other exemplary probes include acetylcholine, acetylthiocholine, propionylcholine, propionylthiocholine, butyrylcholine, butyrylthiocholine, acetyl-β-methylcholine, acetyl-β-methylthiocholine, o-nitrophenylacetate, indophenylacetate, p-aminophenyl acetate, α-naphthyl acetate, benzoylcholine, succinylcholine, adipoylcholine, lauroylcholine, indoxyl acetate, resorufin ester (e.g., including an acetate ester, a phenylacetate ester, a benzoate ester, a propionate ester, or a butyrate ester, such as resorufin acetate or resorufin butyrate), 1-napthyl acetate, 2-naphthyl acetate, 4-methylumbelliferyl butyrate, N-methyl indoxyl acetate, 2,6-dichloroindophenyl acetate, 2,3-dicyano-1,4-phenylene diacrylate, mivacurium, procaine, chloroprocaine, tetracaine, cocaine, heroin, bischoline, dithiobischoline, 1,1-dimethyl-4-acetylthiomethylpiperidinium, as well as salts of any of these. Other probes can include aptamers, such as VX203, VX798, GB946, and GB459 (see, e.g., Kammer M et al., *Biosens. Bioelectron.* 2019; 131:119-27).

In particular embodiments, probes are selected based on reactivity with certain cholinesterases. For instance, the probe can be selective for reactivity with AChE, in which exemplary probes include, e.g., acetylcholine, acetylthiocholine, acetyl-β-methylcholine, acetyl-β-methylthiocholine, or salts thereof. In another instance, the probe can be selective for reactivity with BChE, in which exemplary probes include, e.g., benzoylcholine, succinylcholine, adipoylcholine, butyrylcholine, butyrylthiocholine, or salts thereof. In yet another instance, the probe can have similar reactivity with both AChE and BChE, in which exemplary probes include, e.g., propionylcholine, propionylthiocholine, as well as salts thereof.

Other probes include those that react with a choline derivative (e.g., an alkyl choline derivative, such compounds of formula (III), (IIIa), (IIIb), or (IIIc); or an aryl choline derivative, such as compounds of formula (VII), (VIIa), including salts thereof). Such exemplary probes include dithiobisnitrobenzoate (DTNB), dithiodinicotinic acid (DTNA), 2,2'-dithiodipyridine (2-PDS), choline oxidase, peroxidase (e.g., horseradish peroxidase), aminoantipyreneto, 10-acetyl-3,7-dihydroxyphenoxazine, N-[4-(7-diethylamino-4-methylcoumarin-3-yl)phenyl] maleimide, methyl 7-(4-(2,4-dinitrophenylsulfonyl)piperazin-1-yl)-2-oxo-2H-chromene-3-carboxylate, 4,4'-dithiopyridine, as well as combinations thereof.

Yet other assays, cholinesterases, probes, inactivators, beads, capture agents, and linkers are described in Carmany D O et al., "On-substrate enzymatic reaction to determine acetylcholinesterase activity in whole blood by paper spray mass spectrometry," *J. Am. Soc. Mass Spectrom.* 2018; 29:2436-42; Chen G et al., "Thiol-ene click reaction-induced fluorescence enhancement by altering the radiative rate for assaying butyrylcholinesterase activity," *Analyst* 2019; 144:559-66; Chowdhary S et al., "A novel fluorescence based assay for the detection of organophosphorus pesticide exposed cholinesterase activity using 1-naphthyl acetate," *Biochimie* 2019; 160:100-12; Dafferner A J et al., "Immunopurification of acetylcholinesterase from red blood cells for detection of nerve agent exposure," *Chem. Res. Toxicol.* 2017; 30:1897-910; Diao J et al., "Protein surface structural recognition in inactive areas: a new immobilization strategy for acetylcholinesterase," *Bioconjugate Chem.* 2018; 29:1703-13; Du D et al., "Integrated lateral flow test strip with electrochemical sensor for quantification of phosphorylated cholinesterase: biomarker of exposure to organophosphorous agents," *Anal. Chem.* 2012; 84:1380-5; Du D et al., "Magnetic electrochemical sensing platform for biomonitoring of exposure to organophosphorus pesticides and nerve agents based on simultaneous measurement of total enzyme amount and enzyme activity," *Anal. Chem.* 2011; 83:3770-7; EQM Research, Inc., "Test-mate ChE cholinesterase test system (Model 400)," Instruction Manual-E, April 2003, 32 pp.; Hadd A G et al., "Microfluidic assays of acetylcholinesterase inhibitors," *Anal. Chem.* 1999; 71:5206-12; Haigh J R et al., "Advantages of the WRAIR whole blood cholinesterase assay: comparative analysis to the micro-Ellman, Test-mate ChE™, and Michel (ΔpH) assays," *Chemico-Biol. Interact.* 2008; 175:417-20; He C et al., "A ratiometric fluorescence assay for acetylcholinesterase activity and inhibitor screening based on supramolecular assembly induced monomer-excimer emission transition of a perylene probe," *RSC Adv.* 2018; 8:12785-90; Kammer M et al., "Rapid quantification of two chemical nerve agent metabolites in serum," *Biosens. Bioelectron.* 2019; 131:119-27; Knechtges P L, "An evaluation of blood cholinesterase testing methods for military health surveillance," *United States Army Center for Environmental Health Research (USACEHR) Tech. Rep. No.* 0801, May 2008 (50 pp.); Kostelnik A et al., "Construction of an acetylcholinesterase sensor based on synthesized paramagnetic nanoparticles, a simple tool for neurotoxic compounds assay," *Sensors* 2017; 17:676 (12 pp.); Lee S et al., "Foldable paper-based analytical device for the detection of an acetylcholinesterase inhibitor using an angle-based readout," *Sens. Actuat. B* 2018; 273:322-7; Lin Y S et al., "CD-like centrifugal microfluidic device for organophosphorus pesticides (OPP) sensing," 2017 International Conference on Optical MEMS and Nanophotonics (OMN), held on 13-17 Aug. 2017 in Santa Fe, N. Mex. (2 pp.); Liu R et al., "Application of gold-silver nanocluster based fluorescent sensors for determination of acetylcholinesterase activity and its inhibitor," *Mater. Res. Express* 2018; 5:065027 (11 pp.); Luo Q J et al., "An on-off-on gold nanocluster-based fluorescent probe for sensitive detection of organophosphorus pesticides," *RSC Adv.* 2017; 7:55199-205; Ma K K et al., "In situ induced metal-enhanced fluorescence: a new strategy for bio-sensing the total acetylcholinesterase activity in sub-microliter human whole blood," *Biosens. Bioelectron.* 2015; 68:648-53; Mertens M D et al., "A novel fluorogenic probe for the investigation of free thiols: application to kinetic measurements of acetylcholinesterase activity," *Toxicol. Lett.* 2016; 244:161-6; Miao Y et al., "History and new development of assays for cholinesterase activity and inhibition," *Chem. Rev.* 2010; 110:5216-34; Mukhametshina A R et al., "Luminescent silica nanoparticles for sensing acetylcholinesterase-catalyzed hydrolysis of acetylcholine," *Biosens. Bioelectron.* 2016; 77:871-8; Oliveira G H et al., "Cholinesterase measurements with an automated kit," *Am. J. Indust. Med.* 2002; Supp. 2:49-53; Rajapakse B N et al., "Evaluation of the Test-mate ChE (cholinesterase) field kit in acute organophosphorous poisoning," *Ann. Emerg. Med.* 2011; 58:559-64; Ren X et al., "A sensitive biosensor for the fluorescence detection of the acetylcholinesterase reaction system based on carbon dots," *Colloids Surf B* 2015; 125:90-5; Rosenberry T L et al., "Comparison of the binding of reversible inhibitors to human butyrylcholinesterase and acetylcholinesterase: a crystallographic, kinetic and calorimetric study," *Molecules* 2017; 22:2098 (21 pp.); Schiedel M et al., "Synthesis and biological evaluation of 8-hydroxy-2,7-naphthyridin-2-ium salts as novel inhibitors of acetylcholinesterase (AChE) and butyrylcholinesterase (BChE)," *Med. Chem. Commun.* 2017; 8:465-70; Sorenson K et al., "An inhibitory monoclonal antibody to human acetylcholinesterases," *Biochim. Biophys. Acta* 1987; 912:56-62; Štěpánková Š et al., "Cholinesterase-based biosensors," *J. Enzyme Inhib. Med. Chem.* 2016; 31:180-93; Taylor P W et al., "Field verification of Test-Mate ChE," *Military Med.* 2003; 168:314-9; Trueblood A B et al., "Feasibility of portable fingerstick cholinesterase testing in adolescents in south Texas," *J. Primary Care Commun. Health* 2019; 10:1-6; Worek F et al., "On-site analysis of acetylcholinesterase and butyrylcholinesterase activity with the ChE check mobile test kit determination of reference values and their relevance for diagnosis of exposure to organophosphorus compounds," *Toxicol. Lett.* 2016; 249:22-8; and Zhang R L et al., "Simple and sensitive fluorescence assay for acetylcholinesterase activity detection and inhibitor screening based on glutathione-capped gold nanoclusters," *Sens. Actuat. B* 2017; 253:196-202, each of which is incorporated herein by reference in its entirety.

Inactivators

The methods, devices, and systems herein can be employed to assess the extent of exposure to an inactivator that inhibits cholinesterase. Exemplary inactivators include, e.g., organophosphorous agents (e.g., an organophosphate agent), including but not limited to tabun (GA), sarin (GB), chlorosarin, soman (GD), chlorosoman, cyclosarin (GF), diisopropylfluorophosphate (DFP), VR nerve agent (N,N-diethyl-2-(methyl-(2-methylpropoxy)phosphoryl)sulfanylethanamine or R-33), VX nerve agent (O-ethyl S-[2-(diisopropylamino)ethyl] methylphosphonothioate or Venomous Agent X), methyl paraoxon, ethyl paraoxon, or methyl parathion; an insecticide, including carbamates or organophosphorous or phosphorothioate agents, such as azamethiphos, azinphos-methyl, chlorpyrifos, coumaphos, cyanophos, demeton, diazinon, dichlorovos, diisopropyl fluorophosphate (DFP), dioxathion, fenitrothion, fonofos, glyphosate, malathion, methamidophos, mevinphos, oxydemeton-methyl, parathion, phosmet, tetrachlorvinphos, and tetraethylpyrophosphate (TEPP); or a metabolite of any of these, such as chlorpyrifos oxon, diazoxon, malaoxon, or paraoxon; or a simulant of any of these, such as an organic molecule including a phosphoryl group (e.g., as defined herein) or a phosphate group (e.g., $P(O)XO_2^{2-}$, where X is halo, as defined herein; $P(O)XR^{Ak}O^-$, where X is halo and $R^{Ak}$ is optionally substituted alkyl, as defined herein; or $PO_4^{3-}$), or an exemplary substituted organophosphate compound having the formula of $P(O)(OR^1)(OR^2)(OR^3)$, $P(O)(X)(OR^2)(OR^3)$, $P(O)(R^1)(OR^2)(OR^3)$, $P(O)(R^1)(X)(OR^3)$, $P(O)(R^1)(OR^2)(SR^3)$, $P(O)(X^1)(X^2)(NR^2R^3)$, $P(O)(X^1)(X^2)(OR^2)$, $P(S)(OR^1)(OR^2)(OR^3)$, $P(S)(SR^1)(OR^2)(OR^3)$, $P(S)(X)(OR^2)(OR^3)$, or $P(S)(X)(R^2)(OR^3)$, where each X, $X^1$, and $X^2$, is, independently, halo, hydroxyl, haloalkyl, or cyano, and where each of $R^1$, $R^2$, and $R^3$, independently, is optionally substituted alkyl (e.g., optionally substituted methyl, ethyl, propyl, or butyl), optionally substituted aryl (e.g., optionally substituted phenyl), or optionally substituted alkaryl (e.g., optionally substituted benzyl).

Further exemplary chemical agents include a trialkyl phosphate (e.g., $P(O)(OR^1)(OR^2)(OR^3)$), an alkyl dialkylphosphonate (e.g., $P(O)(R^1)(OR^2)(OR^3)$), a dialkyl alkylphosphinate (e.g., $P(O)(R^1)(R^2)(OR^3)$), where each of $R^1$, $R^2$, and $R^3$, independently, is optionally substituted alkyl (e.g., optionally substituted methyl, ethyl, propyl, or butyl), optionally substituted aryl (e.g., optionally substituted phenyl), or optionally substituted alkaryl (e.g., optionally substituted benzyl). Yet other exemplary chemical agents include a haloalkyl sulfide (e.g., $R^{Hal}-S-R^{Hal}$, $R^{Ak}-S-R^{Hal}$, or $R^{Ar}-S-R^{Hal}$), an alkyl sulfide (e.g., $R^{Ak}-O-$ $R^{Ak}$), an aryl sulfide (e.g., $R^{Ak}$—S—$R^{Ar}$ or $R^{Ar}$—S—$R^{Ar}$), a haloalkylether (e.g., $R^{Ak}$—O—$R^{Hal}$ or $R^{Hal}$—O—$R^{Hal}$) or a haloalkyl amine (e.g., $R^{Hal}$—NH—$R^{Hal}$ or $R^{Hal}$—$NR^{Ak}$—$R^{Hal}$), where each $R^{Ak}$ is, independently, an optionally substituted alkyl; each $R^{Hal}$ is, independently, an optionally substituted haloalkyl; and each $R^{Ar}$ is, independently, an optionally substituted aryl.

Exemplary simulants include dimethyl-4-nitrophenyl phosphate (DMNP), diethyl-4-nitrophenyl phosphate (DENP), bis(4-nitrophenyl) phosphate (BNPP), 4-nitrophenyl diphenylphosphate (NPDP), diisopropyl fluorophosphonate (DFP), isopropyldodecyl fluorophosphate (IDFP), diisopropyl methylphosphonate (DIMP), dimethyl methylphosphonate (DMMP), diethyl methylphosphonate (DEMP), diethyl chlorophosphate (DECP), diethyl cyanophosphonate, dimethyl chlorophosphate (DMCP), methyl dichlorophosphate (MDCP), trimethyl phosphate (TMP), PhX (O-ethyl, S—(N,N-diisopropylethylene) phenylthiophosphonate), diethyl 3-(dimethylamino)propylphosphonate, O,S-diethyl methylthiophosphonate, O,S-diethyl phenylthiophosphonate (DEPPT), O,O-diethyl S-phenylphosphorothioate, S-phenyl diphenyl phosphinothioate, O,O-diethyl N,N-diethylphosphoramidate (DEDEPA), O,O-dicyclohexyl methylphosphonate, O-ethyl N,N-diethylphosphoramidocyanidate, phosphocholine, pinacoylmethylphosphonic acid, methyl phosphonic acid, p-aminophenyl 1,2,2-trimethylpropyl diester (MATP), VX analog (e.g., $(CH_3)P(O)(SC_2H_5)(OC_2H_5)$), 2-chloroethyl ethyl sulfide (CEES), 2-chloroethyl ethyl ether (CEEE), 2-chloroethyl phenyl sulfide, bis(chloroethyl) ether (oxygen mustard), or thioanisole.

Yet other exemplary inactivators include, e.g., acotiamide, aldicarb, ambenonium, bendiocarb, bufencarb, cadusafos, carbaryl, carbendazim, carbetamide, carbofuran, carbosulfan, chelerythrine, chlorbufam, chloropropham, chlorpyrifos, coumarin, cyclosarin, demecarium, diazinon, dichlorvos, diisopropyl fluorophosphate, dimethoate, donepezil, dyflos, echothiophate, edrophonium, ethiofencarb, formetanate, galantamine, huperzine A, huperzine B, lactucopicrin, ladostigil, malathion, methiocarb, methomyl, metrifonate (trichlorfon), neostigmine, onchidal, oxamyl, parathion, phenmedipham, physostigmine, pinmicarb, pirimicarb, propamocarb, propham, propoxur, pyridostigmine, rivastigmine, sarin, soman, tabun, tacrine, tubocurarine, ungeremine, VE agent, VG agent, VM agent, VX agent, or zanapezil.

Centrifugal Devices

A microfluidic disc can be operated as a centrifugal device. In some instances, the device includes a substrate that may at least partially define an assay region, as well as a port (e.g., a sample port or inlet port) configured to receive a sample. The port can be in fluidic communication with any useful chamber (e.g., within an assay area) or any useful region of the device (e.g., an assay area). During operation, a sample (e.g., a fluid sample including a plurality of particles, such as beads or cells) may be transported by applying a centrifugal force that is directed from an interior of the microfluidic disc toward a periphery of the microfluidic disc. The centrifugal force may be generated by rotating the microfluidic disc in any useful direction.

The device can be designed to facilitate multiplexed detection, in which multiple samples can be processed at the same time and/or each particular sample can be divided to be tested for multiple different targets (e.g., both AChE and BChE). For instance, the device can include a plurality of assay areas configured for multiplexed and/or parallel detection.

Assay Areas, Including Detection Regions

An assay area includes any portion defined in part by a substrate, in which the assay area facilitates one or more reaction(s), separation(s), and/or detection of a desired target. The assay area can be defined by one or more chambers (e.g., a reagent chamber, an assay chamber, an incubation chamber, as well as channels connecting any useful chamber) in fluidic communication with a sample port configured to receive a test sample. The assay area can include a detection region, which can be a chamber (e.g., a channel) configured to allow for detection of a signal emitted by a label agent that can optionally be affixed directly or indirectly to the target and/or a particle (e.g., a bead or a cell).

During operation, a centrifugal force may generally be used to transport a fluid sample (optionally including particles) from an inlet port (e.g., a sample port) toward an assay area (e.g., a detection region of the assay region). Additionally, centrifugal forces may be used to transport density medium and/or particles from one or more reservoir(s) to the assay area.

The density medium can have a density greater than that of the fluid sample but lower than that of the particles to be detected. These differences in density can be employed to separate the particles from the fluid sample. By applying centrifugal force, flows are induced. Denser particles from the fluid sample are transported through the density medium, but the less dense components of the fluid sample are not transported through the density medium. In this manner, the particles (e.g., bound to one or more targets) are selectively separated from the remaining portions of the test sample, and detection limits can display improved sensitivity and/or selectivity.

The assay area can include a narrowed or tapered region, which can facilitate detection within the assay area. For instance, upon providing a centrifugal force, a sedimentation-based assay can be conducted within the assay area, such that a pellet is formed in a portion of the assay area closest to the edge of the microfluidic device. If this portion terminates in a narrowed or tapered region, then the pellet is distributed across a larger surface area, which may be more effective at transmitting a detection signal. In one instance, a fluorescence signal can be more easily detected across this narrowed region due to reduced scattering, thereby increasing the sensitivity of the assay. Accordingly, the assay area can have any useful dimension (e.g., width, height, radius, depth, etc.) and/or cross-section (e.g., rectangular, triangular, semi-circular, rounded, trapezoidal, etc.) that can be uniform or non-uniform along any axis or dimension. Further details on narrowed or tapered regions are described in U.S. Pat. No. 8,962,346, which is incorporated herein by reference in its entirety.

Chambers

The present apparatus (e.g., device, such as a microfluidic disc) can include one or more chambers, which can be configured to substantially enclose a fluid or a substance in the fluidic device (e.g., a microfluidic disc). Such chambers can include one or more ports (e.g., inlets or outlets), fluidic opening (e.g., vias), fluidic barriers, channels, or any other structure to allow for fluidic communication between one or more chambers, vents, etc. Exemplary chambers include a channel, a reservoir, etc., having any useful geometry or dimension.

The chambers can be designated for a particular use. Particular uses for such chambers include a sample chamber for receiving and/or storing a test sample, an incubation chamber for incubating a test sample, a reaction chamber for reacting a test sample or a processed sample with another reagent, a reagent chamber containing one or more reagents for detecting one or more targets (e.g., containing one or more label agents), a sterilization chamber containing one or more reagents to sterilize or disinfect the test sample (e.g., containing one or more sterilization agents, as described herein), an assay chamber for conducting one or more assays to detect one or more targets, a post-processing chamber to perform one or more procedures (e.g., lysis, polymerase chain reaction (PCR), amplification assay, immunoassay, analytic test, and/or biochemical analysis), and/or a waste chamber for storing one or more by-products of the assay. Each of these chambers can be interconnected by a valve (e.g., a passive valve, an active valve, an NC valve, and/or NO valve) and/or a channel that can optionally include such a valve in its fluidic path.

Substances and materials within a chamber can be transported to any other chamber in any useful manner. In one instance, rotation over a certain threshold results in transporting a reagent from a first chamber to another chamber (e.g., from a reservoir to a chamber in the assay area; or from a sample port to a reservoir; or from a sample port to a chamber in the assay area). In other instances, a channel can have a dimension that requires a certain rotation rate to overcome capillary pressure, such that the channel functions as a valve. In other instances, the channel includes a wax-based valve that requires melting for actuation. Other methods of controlling flow in microfluidic devices (e.g., pressure-induced flow, centrifugal force-driven flow, pumping, etc.) are known and can be implemented with the devices and systems herein.

Microfluidic Devices and Systems

An exemplary system can include one or more modules or components to facilitate performing assays with the microfluidic disc. In one non-limiting instance, the system includes a microfluidic disc, a motor module coupled to the disc and configured to spin the disc in order to generate centrifugal forces, a detection module positioned to detect a signal from one or more label agents in the assay area (e.g., within a detection region), and an optional processing device. An optional actuator may be coupled to the detection module and configured to move the detection module along the detection region in some examples.

In one instance, the motor module may be implemented using a centrifugation and/or stepper motor. The motor module may be positioned relative to the detection module, such that placing the disc on the motor ensures that an assay area, or a portion thereof, is exposed to the detection module. The motor module can include any useful motor, e.g., a brushed DC motor, a solenoid, a servo motor, a linear actuator, as well as combinations thereof.

The detection module may include a detector (e.g., an electronic detector, an optical detector, a cell phone camera, a photodiode, a photomultiplier tube, and/or a CCD camera) suitable for detecting a signal from one or more label agents (e.g., affixed to particles to be detected and/or quantified). The detector module may include, for example, a laser and optics suitable for optical detection of fluorescence from fluorescent labels. In other examples, other detectors, such as electronic detectors, may be used. An optional actuator may move the detector to a variety of locations of the microfluidic disc (e.g., along the assay area) to detect a measurable signal. The one or more actuators may be coupled to the motor module and/or disc, such that the disc is moved relative to the detection module in response to signals from the processing device.

A processing device may be coupled to the motor module, the detection module, and/or the actuator. Furthermore, the processing device can be configured to provide one or more signals (e.g., one or more control signals to those modules and/or components), as well as to receive one or more signals (e.g., one or more electronic signals from the detection module corresponding to the presence or absence of label agent). All or selected components or modules may be housed in a common housing or in separate enclosures (e.g., optionally configured to operate together, such as by providing a hinged housing formed by connecting an upper enclosure to a lower enclosure by use of a hinge). Microfluidic discs may be placed on the motor module and removed, such that multiple discs may be analyzed by the system.

The processing device may include one or more processing units, such as one or more processors. In some examples, the processing device may include a controller, logic circuitry, and/or software for performing functionalities described herein. The processing device may be coupled to one or more memories, input devices, and/or output devices including, but not limited to, disc drives, keyboards, mice, and displays. The processing device may provide control signals to the motor module to rotate the microfluidic disc at selected speeds for selected times. The processing device may provide control signals to the detection module (e.g., including one or more detectors and/or actuators), detect signals from the label agent(s), and/or move the detector to particular locations. The processing device may develop these control signals in accordance with input from an operator and/or in accordance with software. The software may include one or more executable instructions (e.g., stored on one or more memories) configured to cause the processing device to output a predetermined sequence of control signals, to perform one or more calculations (e.g., determine the presence or absence of a target based on electronic signals from the detection module), to communicate any useful output (e.g., a result, a setpoint, a level, etc.) over a network, to store any useful output in memory, and/or display any useful output on a display module. It is to be understood that the configuration of the processing device and related components is quite flexible, and any of a variety of computing systems may be used including server systems, desktops, laptops, controllers, and the like.

In another instance, the system can include a temperature control system that allows for particular regions of the device to be selectively heated, while masking other regions to minimize heating. For instance, the system employs an infrared emitter to direct radiation to a surface of the device. A mask is employed to shield portions of the device from direct radiation.

In some embodiments, the system can include a non-contact temperature control system for the microfluidic device, where the temperature control system includes an infrared emitter configured to emit at a wavelength of from about 1 μm to about 5 μm (e.g., a peak wavelength of from about 2 μm to about 3 μm) and positioned to direct radiation to a first surface of the microfluidic device. In some embodiments, a focal point of the emitter is configured to be positioned on or within the first assay area, or a portion thereof, of the microfluidic device.

In other embodiments, the system includes a microfluidic disc including a substrate and a first assay area, which is disposed, at least in part, within or on the substrate; and a non-contact temperature control system for the microfluidic device, where the temperature control system including an infrared emitter configured to emit at a wavelength of from about 1 μm to about 5 μm and positioned to direct radiation to a first surface of the microfluidic device, and where a focal point of the emitter configured to be positioned on or within the first assay area, or a portion thereof, of the microfluidic device. Optionally, the temperature control system can include a reflector configured to reflect radiation that is collected from a second surface of the microfluidic device, where the second surface opposes the first surface. In some embodiments, the focal point of the emitter and a vertex of the reflector are aligned along a central axis. In other embodiments, the focal point is configured to be positioned on or within the assay area (e.g., the first and/or second assay area) containing a density medium. In some embodiments, the assay area includes a narrowed region, and the focal point is configured to be positioned on or within the narrowed region.

In some embodiments, the system further includes a mask configured to be disposed between the emitter and the microfluidic device. In some embodiments, the mask includes an opening to provide selective heating of the first assay area of the microfluidic device and a shielded region to provide selective masking of the second assay area of the microfluidic device. In any embodiment herein, the temperature control system further includes a cooling fan configured to be in proximity to the emitter. In some embodiments, the emitter and the cooling fan are configured to be positioned above the microfluidic device. In further embodiments, the reflector and the detection module are configured to be positioned below the microfluidic device.

Exemplary embodiments of a non-contact temperature control system are described in, e.g., Phaneuf C R et al., "Portable centrifugal microfluidic platform for nucleic acid detection," SAND Report No. SAND2016-7047C, 20th International Conference on Miniaturized Systems for Chemistry and Life Sciences, held on 9-13 Oct. 2016 in Dublin, Ireland, 2 pp.; and Phaneuf C R et al., "Integrated LAMP and immunoassay platform for diarrheal disease detection," *Biosens. Bioelectron.* 2018; 120:93-101, each of which is incorporated herein by reference in its entirety.

The system can include one or more interacting modules. In any embodiment herein, the system (e.g., the detection system or the temperature control system) includes a microfluidic disc (e.g., including a substrate; and an assay area disposed, at least in part, within or on the substrate); an infrared emitter (e.g., configured to emit at a wavelength of from about 1 µm to about 5 µm and positioned to direct radiation to a first surface of the microfluidic device, where a focal point of the emitter configured to be positioned on or within an assay area, or a portion thereof), of the microfluidic device; a motor module (e.g., configured to be coupled to the microfluidic disc and to spin the microfluidic disc in response to a motor control signal); and a detection module (e.g., configured to detect a signal from one or more label agents present in the assay area, where the detection module is configured to generate an electronic detection signal based, at least in part, on the signal from the one or more label agents). In some embodiments, the system further includes a reflector, e.g., configured to reflect radiation that is collected from a second surface of the microfluidic device, where the second surface opposes the first surface, where the focal point of the emitter and a vertex of the reflector are aligned along a central axis.

Such modules can include a processing device. In any embodiment herein, the system (e.g., the detection system or the temperature control system) includes a processing device (e.g., coupled to the motor module and the detection module). In some embodiments, the processing device is configured to generate the motor control signal and provide the motor control signal to the motor module. In other embodiments, the processing device is further configured to receive the electronic detection signal from the detection module.

Another exemplary module includes a non-contact temperature control module. In any embodiment herein, the non-contact temperature control module includes an infrared emitter configured to emit at a wavelength of from about 1 µm to about 5 µm and positioned to direct radiation to a first surface of the microfluidic device; a reflector configured to reflect radiation that is collected from a second surface of the microfluidic device; and a focal point of the emitter configured to be positioned on or within the detection region, or a portion thereof, of the microfluidic device, where the second surface opposes the first surface, and where the focal point of the emitter and a vertex of the reflector are aligned along a central axis.

Yet other modules include a motor module and/or a detection module. In any embodiment herein, the motor module is configured to be coupled to the microfluidic disc, to receive a motor control signal, and to spin the microfluidic disc responsive to the motor control signal. In any embodiment herein, the detection module is positioned to detect a signal from one or more label agents affixed to the plurality of particles, where the detection module is configured to generate an electronic detection signal based, at least in part, on the signal from the one or more label agents. In any embodiment herein, the processing device is coupled to the motor module and the detection module, where the processing device is configured to generate the motor control signal and provide the motor control signal to the motor module, and where the processing device is further configured to receive the electronic detection signal from the detection module.

In any embodiment herein, the system (e.g., the detection system or the temperature control system) includes an upper enclosure (e.g., configured to contain the emitter) and a lower enclosure (e.g., configured to contain the reflector, the motor module, and the detection module). In some embodiments, the upper enclosure is further configured to contain a cooling fan and maintain the cooling fan in proximity to the emitter. In other embodiments, the lower enclosure is further configured to contain the microfluidic disc.

The system can include any other modifications to facilitate rotation of the device and/or detection within the device. In one instance, the device includes a structure configured to align an assay area with a detection module. In one non-limiting embodiment, an assay area can include a corresponding tooth element. In another non-limiting embodiment, each assay area includes a corresponding tooth element. In yet another non-limiting embodiment, one tooth element can be an extended tooth element having a different dimension than another tooth element. In use, the system can include a device including a plurality of assay regions and corresponding tooth elements; a motor module configured to move the device such that the assay areas move along a first path (e.g., a circular path disposed on a surface of the device) and the tooth elements move along a second path (e.g., a circular path disposed on an edge or along a periphery of the device); an impinging element configured for placement in a first position that allows for movement of device and a second position, wherein the impinging element engages at least one tooth element when in the second position; a detection module configured to detect a signal (e.g., arising the detection region or the assay area; arising from one or more label agents or one or more targets); and processing device (e.g., a controller) communicatively coupled to the impinging element and the motor module, where the processing device is configured to provide a control signal to the impinging element to place the impinging element in the first position or the second position. In some embodiments, the detection module is positioned such that when the impinging element is in the second position, the detection module is aligned with at least one of the plurality of assay regions.

Exemplary devices (e.g., apparatuses) and systems, as well as methods employing such devices and systems, are described in U.S. Pat. Nos. 8,945,914, 8,962,346, 9,186,668, 9,244,065, 9,304,128, 9,304,129, 9,500,579, 9,702,871, 9,766,230, 9,795,961, 9,803,238, 9,903,001, 10,024,849, 10,254,298, 10,384,202, and 10,406,528, as well as U.S. Pat. Appl. Pub. Nos. 2015/0360225, 2018/0037960, and 2018/0065118, each of which is incorporated herein by reference in its entirety Density Medium and Particles The present invention can be employed with any useful agents, including a density medium, a particles, as well as combinations thereof. The density medium may have a density lower than a density of a plurality of particles (e.g., beads or cells) and higher than a density of the fluid sample. The density medium may generally be implemented using a fluid having a density selected to be in the appropriate range, e.g., lower than a density of the particles to be detected or quantified and higher than a density of the fluid sample. In some examples, a fluid sample may be diluted for use with a particular density medium. The density medium may include, for example, a salt solution containing a suspension of silica particles, which may be coated with a biocompatible coating (e.g., a polyvinylpyrrolidone (PVP) coating or a silane coating). In some embodiments, the density medium is a dense solution (e.g., a solution denser than water, including an aqueous solution having a polymer, a sugar, a carbohydrate, an ionic salt, a saccharide, an alcohol, a polyhydric alcohol, as well as polymeric forms thereof, conjugated forms thereof, iodinated forms thereof, or modified forms thereof). In other embodiments, the density medium is an ionic gradient media (e.g., a solution including one or more inorganic salts and/or heavy metal salts, such as cesium chloride, cesium sulfate, lithium chloride, potassium bromide, sodium polytungstate, etc.). In yet other embodiments, the density medium is an iodinated gradient media (e.g., a nonionic iodinated gradient media). In other embodiments, the density medium is a colloidal media, which is a colloidal suspension of one or more particles (e.g., coated particles).

Examples of suitable density media are Percoll™ (colloidal silica coated with PVP), Percoll™ PLUS (colloidal silica coated with silane), Ficoll™ PM70 (high molecular weight sucrose-polymers with an average molecular weight of 70,000), Ficoll™ 400 (a copolymer of sucrose and epichlorohydrin), Ficoll™ PM400 (a synthetic neutral, highly-branched hydrophilic polymer of sucrose with an average molecular weight of 400,000), Ficoll-Paque™ PLUS (a combination of Ficoll™ PM400, sodium diatrizoate, and disodium calcium EDTA), and Ficoll-Paque™ Premium (a combination of Ficoll™ PM400, sodium diatrizoate, and disodium calcium EDTA in water for injection), each of which is available from GE Healthcare Life Sciences, Little Chalfont, Buckinghamshire, United Kingdom.

Other examples of suitable density media are Histopaque® (a combination of polysucrose and sodium diatrizoate, including a Histopaque®-1077 formulation adjusted to a density of 1.077 g/mL, a Histopaque®-1083 formulation adjusted to a density of 1.083 g/mL, and a Histopaque®-1119 formulation adjusted to a density of 1.119 g/mL), diatrizoate (e.g., meglumine diatrizoate or sodium diatriazoate), diatrizoic acid, diatrizoic acid dihydrate, iodixanol, iohexol (e.g., sold as HistoDenz™ or Nycodenz™), metrizamide, glycerol, sorbitol, sucrose (e.g., polysucrose), dextran, and dextran sulfate (e.g., dextran sulfate sodium salt), as well as salts of any of these, mixtures thereof, and solutions thereof.

Particular densities may be achieved by adjusting a percentage of the density medium in a salt solution. Generally, viscosity and density of the density medium may be adjusted by selecting a composition of the medium. Varying the concentration of solutes such as sucrose or dextran in the medium may adjust the density and/or viscosity.

In some instances, sedimentation assays can be conducted, in which the settling velocity of a particle is described by known Stoke's flow equations. Sedimentation rates typically scale with a square of a particle's radius and can be linearly dependent with the difference in density between a particle and a surrounding fluid (e.g., as provided by a sample or by a density medium). Thus, under certain conditions, a population of particles can be separated according to its density and/or radius.

Particles of different sizes can be employed, in which the different sedimentation rates can be used to allow size-based separation and/or detection. The sedimentation rate of a particle is dependent on various characteristics of the particle, including particle size, particle surface charge, and/or particle density. Sedimentation can occur under any force, such as gravitational force or centrifugal force (e.g., by rotating or spinning a microfluidic device). In one non-limiting example, a first population of particles (e.g., having a first particle size and/or first particle density) can include a first type of capture agent, and a second population of particles (e.g., having a second particle size and/or second particle density) can include a second type of capture agent, thereby allowing for different sedimentation rates and/or separation zones for each population. For instance, smaller and/or less dense particles can be localized in a first separation zone, and larger and/or more dense particles can be localized in a second separation zone, thereby allowing for separation of different populations of particles by employing centrifugal force. Further details on sedimentation assays are provided in U.S. Pat. No. 8,945,914, which is incorporated herein by reference in its entirety.

Particles can be composed of any useful material and have any useful chemical properties (e.g., surface charge, including a positively charged surface or a negatively charged surface). Exemplary materials include polystyrene, polymethylmethacrylate, silica, metal (e.g., gold, iron, or iron oxide), as well as combinations thereof and coated versions thereof (e.g., including a polymer coating, a charged coating, or a coating including binding groups, such reactive linkers, antibodies, integrins, and/or selectins). Particles can have any useful dimension (e.g., as in microparticles, nanoparticles, etc.) depending on their use. For example, particle dimensions may be useful for use as sedimentation particles, whereas other dimensions or characteristics for use as labeling particles. In one non-limiting instance, a sedimentation particle can be modified to bind to certain cells, thereby increasing the sedimentation rate of certain cells upon binding and allowing these certain cell types to be selectively removed from the sample during centrifugation.

Other substances or reagents can be employed in conjunction with the density medium and/or a population of particles. In one instance, a separation layer fluid is employed, which forms an interface between a density medium and a sample, between a sample and a particle, and/or between the density medium and the particle. This separation layer fluid can have nay useful density (e.g., denser than the density medium but less dense than the particle; denser than the sample but less dense than the density medium; or denser than the sample but less dense than the particle). The separation layer fluid can include any useful substance, e.g., a hydrophobic material, a mineral oil, an organic oil, a charged or water ordering polymer, a salt in a water-based medium, a fluoroalkane fluid, a perfluorocarbon, or a perfluoroalkane fluid. Further details on separation layer fluids are provided in U.S. Pat. Nos. 8,962,346 and 9,304,129, each of which is incorporated herein by reference in its entirety.

Label Agents and Capture Agents

A label agent includes any moiety that can emit a signal suitable for detection, such as an optical or an electrical signal. Exemplary moieties can include a fluorescent moiety (e.g., a fluorophore), a probe (e.g., any described herein), or a label (e.g., a fluorescent, chemiluminescent, or electroactive label, such as any described herein).

The label agent can optionally include a capture portion, which binds to a target or a portion thereof. Furthermore, a label agent can be used in conjunction with a capture agent (e.g., as in a sandwich assay, which can include use of a capture agent to bind a first region of the target to a bead and use of a label agent to bind to a second region of the target in order to provide a detectable signal).

Exemplary capture agents include a protein that binds to or detects one or more markers (e.g., an antibody or an enzyme), an affibody, an aptamer, a globulin protein (e.g., bovine serum albumin), a nanoparticle, a microparticle, a sandwich assay reagent, a nucleic acid (e.g., single stranded nucleic acid, double stranded nucleic acid, hairpin nucleic acid, DNA, RNA, cell-free nucleic acids, as well as chimeras thereof, hybrids thereof, or modifications thereof), a toxin capture agent (e.g., a sarcin-ricin loop capture agent), a major histocompatibility complex capture agent (e.g., a MHC II capture agent), or a catalyst (e.g., that reacts with one or more markers.

Further exemplary capture agents include antibodies, affibodies, aptamers, etc., including polyclonal and monoclonal forms. Yet other exemplary capture agents include acetylcholinesterase antibody (e.g., rabbit/IgG (host/isotype), polyclonal, human AChE-GST fusion protein Ag12146 (immunogen), such as catalog no. 17975-1-AP from Proteintech Group, Inc., Rosemont, Ill.; mouse/IgG2b (host/isotype), monoclonal, purified human cerebellar acetylcholinesterase (immunogen), such as catalog no. MA3-042 from Thermo Fisher Scientific, Waltham, Mass.; mouse/IgG1 (host/isotype), monoclonal, AChE from human erythrocytes (immunogen), clone AE-1, such as catalog no. MAB303 from Sigma-Aldrich Corp., St. Louis, Mo.; mouse/IgG1 (host/isotype), monoclonal, AChE from human erythrocytes (immunogen), clone AE-2, such as catalog no. MAB304 from Sigma-Aldrich Corp.; mouse/IgG2b (host/isotype), monoclonal, purified rat brain acetylcholinesterase (immunogen), such as catalog no. MA3-041 from Thermo Fisher Scientific; rabbit/IgG (host/isotype), polyclonal, recombinant fragment corresponding to a region within amino acids 406 and 614 of human AChE provided in UniProt Entry No. P22303 (immunogen), such as catalog no. PA5-21371 from Thermo Fisher Scientific; goat/IgG (host/isotype), polyclonal, synthetic peptide sequence (QFDHYSKQDRCSDL, SEQ ID NO:1) corresponding to the C-terminus amino acids of AChE (immunogen), such as catalog no. PA5-18348 from Thermo Fisher Scientific; rabbit/IgG (host/isotype), polyclonal, KLH-conjugated synthetic peptide corresponding to a region within amino acids 147 and 175 of human AChE (immunogen), such as catalog no. PA5-15010 from Thermo Fisher Scientific; rabbit/IgG (host/isotype), polyclonal, synthetic peptide corresponding to residues in human AChE (immunogen), such as catalog no. PA5-86086 from Thermo Fisher Scientific; rabbit/IgG (host/isotype), polyclonal, synthetic peptide corresponding to a region within amino acids 560 and 600 of human AChE (immunogen), such as catalog no. PA5-86637 from Thermo Fisher Scientific; rabbit/IgG (host/isotype), polyclonal, synthetic peptide corresponding to a sequence at the C-terminus of human AChE that is different from the related mouse sequence (UniProt Entry No. P21836) and rat sequence (UniProt Entry No. P37136) by one amino acid (immunogen), such as catalog no. PA5-95250 from Thermo Fisher Scientific; goat/IgG (host/isotype), polyclonal, acetyl cholinesterase from bovine erythrocytes provided in UniProt Entry No. P23795 (immunogen), such as catalog no. PA1-26888 from Thermo Fisher Scientific; mouse/IgG2b (host/isotype), monoclonal, human cerebellar AChE (immunogen), clone HIR2, such as catalog no. ab2803 from Abcam PLC, Cambridge, UK; mouse/IgG1 kappa (host/isotype), monoclonal, synthetic peptide corresponding to a region within amino acids 574 and 583 of human AChE (immunogen), such as catalog no. ab17774 from Abcam PLC; rabbit/IgG (host/isotype), monoclonal, synthetic peptide corresponding to a region within amino acids 50 and 150 of mouse AChE provided in UniProt Entry No. P21836 (immunogen), such as catalog no. ab183591 from Abcam PLC; mouse/IgG1 kappa (host/isotype), monoclonal, purified and detergent solubilized full length human AChE (immunogen), such as catalog no. ab23455 from Abcam PLC; rabbit/IgG (host/isotype), monoclonal, synthetic peptide corresponding to a region within amino acids 50 and 150 of mouse AChE (immunogen), such as catalog no. ab240274 from Abcam PLC; goat/IgG (host/isotype), polyclonal, synthetic peptide of SEQ ID NO:1 corresponding to a region within amino acids 601 and 614 of human AChE (immunogen), such as catalog no. ab31276 from Abcam PLC; rabbit/IgG (host/isotype), polyclonal, synthetic peptide from the N-terminal region of human AChE (immunogen), such as catalog no. ab78228 from Abcam PLC; rabbit/IgG (host/isotype), polyclonal, recombinant fragment corresponding to a region within amino acids 406 and 610 of human AChE (immunogen), such as catalog no. ab97299 from Abcam PLC; monoclonal antibody 1G having heavy and light chain variable regions with a sequences provided in GenBank Acc. Nos. ARX71332.1 and ARX71333.1, respectively; monoclonal antibody 6A having heavy and light chain variable regions with sequences provided in GenBank Acc. Nos. ARX71334.1 and ARX71335.1, respectively; monoclonal antibody 10D having heavy and light chain variable regions with sequences provided in GenBank Acc. Nos. ARX71330.1 and ARX71331.1, respectively; monoclonal antibody AE-1 having heavy and light chain variable regions with sequences provided in GenBank Acc. Nos. ARX71336.1 and ARX71337.1, respectively; and monoclonal antibody AE-2 having heavy and light chain variable regions with sequences provided in GenBank Acc. Nos. ARX71338.1 and ARX71339.1, respectively) and butyrylcholinesterase antibody (e.g., mouse/IgG1 kappa (host/isotype), monoclonal, human BChE from plasma (immunogen), such as catalog no. HAH 002-01-02 from Thermo Fisher Scientific; rabbit/IgG (host/isotype), polyclonal, recombinant fusion protein containing a sequence corresponding to amino acids 29-270 of human BChE provided in UniProt Entry No. P06276 (immunogen), such as catalog no. PA5-89930 from Thermo Fisher Scientific; rabbit/IgG (host/isotype), polyclonal, recombinant mouse BChE protein (immunogen), such as catalog no. PA5-81319 from Thermo Fisher Scientific; rabbit/IgG (host/isotype), polyclonal, recombinant fragment corresponding to a region within amino acids 59 and 297 of human BChE (immunogen), such as catalog no. PA5-27385 from Thermo Fisher Scientific; rabbit/IgG (host/isotype), polyclonal, recombinant fragment corresponding to a region within amino acids 311 and 524 of human BChE (immunogen), such as catalog no. PA5-97500 from Thermo Fisher Scientific; rabbit/IgG (host/isotype), polyclonal, E. coli-derived recombinant fragment corresponding to a region within amino acids 263 and 571 of mouse BChE provided in UniProt Entry No. Q03311 (immunogen), such as catalog no. PA5-78861 from Thermo Fisher Scientific; rabbit/IgG (host/isotype), polyclonal, KLH-conjugated synthetic peptide corresponding to a region within amino acids 385 and 415 of human BChE (immunogen), such as catalog no. PA5-14971 from Thermo Fisher Scientific; mouse/IgG1 kappa (host/isotype), monoclonal, native full length purified human BChE (immunogen), such as catalog no. ab17246 from Abcam PLC; mouse/IgG1 (host/isotype), monoclonal, recombinant full length protein corresponding to native human BChE from NCBI Entry No. NP_000046 (immunogen), such as catalog no. ab117960 from Abcam PLC; rabbit/IgG (host/isotype), monoclonal, synthetic peptide corresponding to a region within amino acids 550 and 650 of human BChE (immunogen), such as catalog no. ab151554 from Abcam PLC; rabbit/IgG (host/isotype), polyclonal, recombinant fragment corresponding to a region within amino acids 59 and 297 of human BChE (immunogen), such as catalog no. ab154763 from Abcam PLC; and rabbit/IgG (host/isotype), polyclonal, recombinant fragment corresponding to a region within amino acids 311 and 524 of human BChE (immunogen), such as catalog no. ab236577 from Abcam PLC), in which sequences from each recited UniProt Entry No., GenBank Acc. No., and NCBI Entry No. is incorporated herein by reference in its entirety.

Yet other exemplary capture agents include antibodies, in which portions of such antibodies can include any sequence (or a fragment thereof) provided in FIG. 10A-10I, FIG. 11A-11C, FIG. 12, FIG. 13A-13I, FIG. 14A-14C, and FIG. 15. In one embodiment, the antibody includes a heavy chain (HC) and a light chain (LC), in which the HC variable region includes SEQ ID NOs:20-34 or a fragment thereof and in which the LC variable region includes SEQ ID NOs:40-48, 50-64, or a fragment hereof. In another embodiment, the antibody further includes an HC constant region (e.g., including SEQ ID NO:35-38 or a fragment thereof) and a LC constant region (e.g., including SEQ ID NOs:70-74 or a fragment thereof). In yet another embodiment, the HC includes a first CDR including SEQ ID NO:30, a second CDR including SEQ ID NO:31, and a third CDR including SEQ ID NO:32. In another embodiment, the LC includes a first CDR including SEQ ID NO:60, a second CDR including SEQ ID NO:61, and a third CDR including SEQ ID NO:62.

In some embodiments, the HC variable region includes or is a polypeptide sequence having at least 90% sequence identity to SEQ ID NO:29:

$X_1VX_3X_4X_5X_6SGX_9X_{10}X_{11}X_{12}X_{13}X_{14}GX_{16}SX_{18}KX_{20}SCX_{23}ASX_{26}X_{27}X_{28}FX_{30}X_{31}X_{32}X_{33}X_{34}X_{35}$ $WVX_{38}X_{39}X_{40}X_{41}X_{42}X_{43}X_{44}LEWX_{48}X_{49}X_{50}IX_{52}X_{53}X_{54}X_{55}X_{56}X_{57}X_{58}X_{59}YX_{61}X_{62}X_{63}X_{64}KX_{66}X_{67}$ $X_{68}TX_{70}X_{71}X_{72}DX_{74}X_{75}X_{76}X_{77}X_{78}X_{79}X_{80}X_{81}X_{82}X_{83}X_{84}X_{85}LX_{87}X_{88}EDX_{91}X_{92}X_{93}YX_{95}CX_{97}RX_{99}$ $X_{100}X_{101}X_{102}X_{103}X_{104}X_{105}X_{106}X_{107}X_{108}X_{109}YWGQGX_{115}X_{116}X_{117}TVX_{120}X_{121}$ wherein:
each of $X_1$, $X_6$, $X_{62}$, and $X_{82}$ is G, D, E, N, or Q;
each of $X_3$, $X_{13}$, and $X_{43}$ is N, Q, R, H, or K;
each of $X_4$, $X_{11}$, $X_{12}$, $X_{20}$, $X_{34}$, $X_{48}$, $X_{49}$, $X_{81}$, $X_{92}$, $X_{93}$, and $X_{117}$ is G, A, V, I, L, or M;
each of $X_5$ and $X_{39}$ is G, A, V, I, L, N, or Q;
each of $X_9$, $X_{16}$, $X_{28}$, $X_{58}$, $X_{75}$, $X_{78}$, $X_{79}$, $X_{97}$, $X_{115}$, $X_{116}$, and $X_{121}$ is G, A, V, I, L, P, S, or T;
each of $X_{10}$ and $X_{42}$ is G, D, or E;
each of $X_{14}$, $X_{30}$, $X_{66}$, $X_{71}$, $X_{88}$, $X_{91}$, and $X_{120}$ is G, P, S, or T;
each of $X_{18}$, $X_{23}$, and $X_{72}$ is A, V, I, L, R, H, or K;
each of $X_{26}$, $X_{54}$, $X_{80}$, and $X_{95}$ is G, F, Y, or W;
each of $X_{27}$, $X_{33}$, and $X_{52}$ is G, F, Y, W, S, or T;
each of $X_{31}$ and $X_{44}$ is G, D, E, R, H, K, S, or T;
$X_{32}$ is N, Q, F, Y, or W;
each of $X_{35}$, $X_{63}$, $X_{74}$, $X_{76}$, $X_{77}$, $X_{84}$, and $X_{85}$ is N, Q, R, H, K, S, or T;
each of $X_{38}$, $X_{41}$, and $X_{67}$ is P, R, H, or K;
each of $X_{40}$, $X_{87}$, and $X_{107}$ is A, V, I, L, F, Y, W, R, H, K, S, or T;
each of $X_{50}$ and $X_{61}$ is A, V, I, L, N, Q, F, Y, W, S, or T;
$X_{53}$ is G, C, U, P, S, or T;
each of $X_{55}$ and $X_{56}$ is G, D, E, N, Q, S, or T;
$X_{57}$ is A, V, I, L, D, E, F, Y, W, S, or T;
each of $X_{59}$ and $X_{99}$ is any amino acid (e.g., D, E, N, Q, R, H, K, F, Y, W, S, or T; or G, D, E, P, F, Y, W, S, or T);
each of $X_{64}$, $X_{68}$, $X_{70}$, $X_{83}$, and $X_{108}$ is A, V, I, L, M, F, Y, or W;
each of $X_{100}$, $X_{103}$, $X_{104}$, and $X_{105}$ is any amino acid or absent (e.g., A, V, I, L, D, E, F, Y, W, R, H, K, or absent; G, A, V, I, L, M, F, Y, W, S, T, or absent; G, A, V, I, L, R, H, K, S, T, or absent; or D, E, P, F, Y, W, S, T, or absent);
each of $X_{101}$ and $X_{106}$ is G, F, Y, W, or absent;
$X_{102}$ is G, P, S, T, or absent; and
$X_{109}$ is A, V, I, L, D, E, R, H, or K.

In other embodiments, each X in SEQ ID NO:29 can be an amino acid (or a conservative amino acid substitution thereof) in any one of SEQ ID NOs: 20-28 when any one of the sequences in SEQ ID NOs: 20-28 is used as a reference sequence to be optimally aligned with SEQ ID NO:29.

In some embodiments, the HC variable region includes a first CDR including SEQ ID NO:30, a second CDR including SEQ ID NO:31, and a third CDR including SEQ ID NO:32:

$X_1X_2X_3FX_4X_5X_6X_7$,  (SEQ ID NO: 30)

$IX_8X_9X_{10}X_{11}X_{12}X_{13}X_{14}$,  (SEQ ID NO: 31)

and $X_{15}RX_{16}X_{17}X_{18}X_{19}X_{20}X_{21}X_{22}X_{23}X_{24}X_{25}X_{26}Y$,  (SEQ ID NO: 32)

wherein:
each of $X_1$ and $X_{10}$ is G, F, Y, or W;
each of $X_2$, $X_7$, and $X_8$ is G, F, Y, W, S, or T;
each of $X_3$, $X_{14}$, and $X_{15}$ is G, A, V, I, L, P, S, or T
each of $X_4$ and $X_9$ is G, C, U, P, S, or T;

$X_5$ is G, D, E, R, H, K, S, or T;
$X_6$ is N, Q, F, Y, or W;
each of $X_{11}$ and $X_{12}$ is G, D, E, N, Q, S, or T
$X_{13}$ is A, V, I, L, D, E, F, Y, W, S, or T;
$X_{16}$ is G, D, E, P, F, Y, W, S, or T;
$X_{17}$, A, V, I, L, D, E, F, Y, W, R, H, K, or absent;
each of $X_{18}$ and $X_{23}$ is G, F, Y, W, or absent;
$X_{19}$ is G, P, S, T, or absent;
$X_{20}$, G, A, V, I, L, M, F, Y, W, S, T, or absent;

$X_{21}$, G, A, V, I, L, R, H, K, S, T, or absent;
$X_{22}$ is D, E, P, F, Y, W, S, T, or absent;
$X_{24}$ is A, V, I, L, F, Y, W, R, H, K, S, or T;
$X_{25}$ is A, V, I, L, M, F, Y, or W; and
$X_{26}$ is A, V, I, L, D, E, R, H, or K.

In other embodiments, each X in SEQ ID NOs:30-32 can be an amino acid (or a conservative amino acid substitution thereof) in any one of SEQ ID NOs:20-28 when any one of the sequences in SEQ ID NOs:20-28 is used as a reference sequence to be optimally aligned with SEQ ID NOs:30-32, respectively.

In some embodiments, the HC variable region includes or is a polypeptide sequence having at least 90% sequence identity to SEQ ID NO:33:

$X_1VX_3X_4X_5X_6SGX_9X_{10}X_{11}VX_{13}X_{14}GX_{16}SX_{18}KX_{20}SCX_{23}ASX_{26}X_{27}X_{28}FX_{30}X_{31}X_{32}X_{33}X_{34}X_{35}$ $WVX_{38}QX_{40}X_{41}X_{42}KX_{44}LEWX_{48}X_{49}X_{50}ISX_{53}X_{54}X_{55}X_{56}X_{57}X_{58}X_{59}YX_{61}X_{62}X_{63}X_{64}KGX_{67}X_{68}TX_{70}X_{71}$ $X_{72}DX_{74}X_{75}X_{76}X_{77}TX_{79}X_{80}X_{81}QX_{83}X_{84}SLX_{87}SEDX_{91}X_{92}X_{93}YX_{95}CX_{97}RX_{99}X_{100}X_{101}X_{102}X_{103}$ $X_{104}X_{105}X_{106}X_{107}X_{108}X_{109}YWGQGTX_{116}X_{117}TVX_{120}X_{121}$ wherein:
each of $X_1$, $X_6$, and $X_{62}$ is G, D, E, N, or Q;
each of $X_3$ and $X_{13}$ is N, Q, R, H, or K;
each of $X_4$, $X_{11}$, $X_{16}$, $X_{20}$, $X_{34}$, $X_{48}$, $X_{49}$, $X_{79}$, $X_{81}$, $X_{92}$, $X_{93}$, and $X_{117}$ is G, A, V, I, L, or M;
each of $X_5$ and $X_{61}$ is G, A, V, I, L, N, or Q;
each of $X_9$, $X_{40}$, $X_{58}$, $X_{75}$, $X_{97}$, $X_{116}$, and $X_{121}$ is G, A, V, I, L, P, S, or T;
each of $X_{10}$ and $X_{42}$ is G, D, or E;
each of $X_{14}$, $X_{28}$, $X_{30}$, $X_{71}$, $X_{91}$, and $X_{120}$ is G, P, S, or T;
each of $X_{18}$, $X_{23}$, and $X_{72}$ is A, V, I, L, R, H, or K;
each of $X_{26}$, $X_{32}$, $X_{54}$, $X_{80}$, and $X_{95}$ is G, F, Y, or W;
each of $X_{27}$, $X_{33}$, $X_{50}$, and $X_{59}$ is G, F, Y, W, S, or T;
each of $X_{31}$, $X_{35}$, $X_{44}$, $X_{63}$, $X_{76}$, and $X_{87}$ is G, R, H, K, S, or T;
each of $X_{38}$, $X_{41}$, and $X_{67}$ is P, R, H, or K;
$X_{53}$ is G, C, U, S, or T;
each of $X_{55}$ and $X_{56}$ is G, D, E, N, Q, S, or T
$X_{57}$ is A, V, I, L, F, Y, W, S, or T;
each of $X_{64}$, $X_{68}$, $X_{70}$, $X_{83}$, and $X_{108}$ is A, V, I, L, M, F, Y, or W;
each of $X_{74}$, $X_{77}$, and $X_{84}$ is N, Q, S, or T;
$X_{99}$ is G, D, E, P, F, Y, or W;
each of $X_{100}$ and $X_{109}$ is A, V, I, L, D, E, F, Y, or W;
each of $X_{101}$ and $X_{106}$ is G, F, Y, W, or absent;
each of $X_{102}$, $X_{104}$, and $X_{105}$ is G, P, S, T, or absent;
$X_{103}$ is G, A, V, I, L, M, S, T, or absent; and
$X_{107}$ is A, V, I, L, F, Y, W, R, H, or K.

In other embodiments, each X in SEQ ID NO:33 can be an amino acid (or a conservative amino acid substitution thereof) in any one of SEQ ID NOs:20-24 when any one of the sequences in SEQ ID NOs:20-24 is used as a reference sequence to be optimally aligned with SEQ ID NO:33.

In yet other embodiments, the HC variable region includes or is a polypeptide sequence having at least 90% sequence identity to SEQ ID NO:34:

$X_1VQLQQSGX_9ELX_{12}X_{13}PGX_{16}SVKX_{20}SCKASGYX_{28}FX_{30}X_{31}X_{32}X_{33}X_{34}X_{35}WVKX_{39}X_{40}X_{41}GX_{43}$ $X_{44}LEWIGX_{50}IYPX_{54}X_{55}X_{56}DTX_{59}YX_{61}X_{62}KFKX_{66}KATLTX_{72}DX_{74}SSSX_{78}X_{79}YX_{81}X_{82}LX_{84}X_{85}$ $LX_{87}X_{88}EDSAVYX_{95}CARX_{99}X_{100}X_{101}X_{102}X_{103}X_{104}X_{105}X_{106}X_{107}X_{108}X_{109}YWGQGX_{115}X_{116}X_{117}$ $TVSS$ wherein:
each of $X_1$, $X_{62}$, and $X_{82}$ is G, D, E, N, or Q;
$X_9$ is G, A, V, I, L, or P;
each of $X_{12}$, $X_{20}$, $X_{34}$, $X_{72}$, $X_{81}$, and $X_{117}$ is G, A, V, I, L, or M;
each of $X_{13}$ and $X_{41}$ is P, R, H, or K;
each of $X_{16}$, $X_{28}$, $X_{78}$, $X_{79}$, $X_{87}$, and $X_{115}$ is G, A, V, I, L, P, S, or T;
each of $X_{30}$, $X_{44}$, $X_{66}$, $X_{88}$, and $X_{116}$ is G, P, S, or T;
each of $X_{31}$ and $X_{99}$ is G, D, E, S, or T;
$X_{32}$ is N, Q, F, Y, or W;
$X_{33}$ is G, F, Y, W, S, or T;
each of $X_{35}$ and $X_{43}$ is N, Q, R, H, or K;
$X_{39}$ is G, A, V, I, L, N, or Q;
each of $X_{40}$ and $X_{74}$ is R, H, K, S, or T;
$X_{50}$ is A, V, I, L, N, Q, F, Y, or W;
each of $X_{54}$ and $X_{95}$ is G, F, Y, or W;
each of $X_{55}$ and $X_{56}$ is G, D, E, N, Q, S, or T;
$X_{59}$ is D, E, N, Q, R, H, K, F, Y, or W;
$X_{61}$ is N, Q, S, or T;
each of $X_{84}$ and $X_{85}$ is N, Q, R, H, K, S, or T;
each of $X_{100}$ and $X_{105}$ is D, E, R, H, K, F, Y, W, or absent;
each of $X_{101}$ and $X_{106}$ is G, F, Y, W, or absent;
$X_{102}$ is G, P, S, T, or absent;
$X_{103}$ is G, A, V, I, L, F, Y, W, or absent;
$X_{104}$ is G, A, V, I, L, R, H, K, S, T, or absent;
$X_{107}$ is R, H, K, F, Y, W, S, or T;
$X_{108}$ is A, V, I, L, M, F, Y, or W; and
$X_{109}$ is D, E, R, H, or K.

In other embodiments, each X in SEQ ID NO:34 can be an amino acid (or a conservative amino acid substitution thereof) in any one of SEQ ID NOs:25-28 when any one of the sequences in SEQ ID NOs:25-28 is used as a reference sequence to be optimally aligned with SEQ ID NO:34.

In particular embodiments, the antibody further includes an HC constant region that includes or is a polypeptide sequence having at least 90% sequence identity to SEQ ID NO:38, in which each X in SEQ ID NO:38 can be any amino acid (e.g., a conservative amino acid substitution of an amino acid in any one of SEQ ID NOs:35-37 when any one of the sequences in SEQ ID NOs:35-37 is used as a reference sequence to be optimally aligned with SEQ ID NO:38). In other embodiments, each X in SEQ ID NO:38 can be an amino acid in any one of SEQ ID NOs:35-37 when any one of the sequences in SEQ ID NOs:35-37 is used as a reference sequence to be optimally aligned with SEQ ID NO:38.

In some embodiments, the LC variable region includes or is a polypeptide sequence having at least 90% sequence identity to SEQ ID NO:59:

$DX_2X_3X_4X_5QX_7X_8X_9X_{10}X_{11}X_{12}X_{13}X_{14}X_{15}GX_{17}X_{18}X_{19}X_{20}X_{21}X_{22}CX_{24}X_{25}SX_{27}X_{28}X_{29}X_{30}X_{31}X_{32}$ $X_{33}X_{34}X_{35}X_{36}X_{37}X_{38}X_{39}X_{40}WX_{42}X_{43}QX_{45}X_{46}X_{47}X_{48}X_{49}X_{50}X_{51}X_{52}LIX_{55}X_{56}X_{57}X_{58}X_{59}X_{60}X_{61}X_{62}$ $GX_{64}PX_{66}RFX_{69}GX_{71}GSGX_{75}DX_{77}X_{78}LX_{80}IX_{82}X_{83}X_{84}X_{85}X_{86}EDX_{89}X_{90}X_{91}X_{92}X_{93}CX_{95}X_{96}X_{97}$ $X_{98}X_{99}X_{100}X_{101}X_{102}TFGX_{106}GTX_{109}LX_{111}X_{112}KR$ wherein:
each of $X_2$, $X_4$, $X_{19}$, $X_{39}$, $X_{64}$, $X_{84}$, $X_{89}$, $X_{90}$, $X_{106}$, and $X_{112}$ is G, A, V, I, L, or M;
each of $X_3$ and $X_{43}$ is G, A, V, I, L, N, or Q;
each of $X_5$, $X_7$, $X_{14}$, $X_{22}$, $X_{58}$, $X_{62}$, $X_{69}$, and $X_{78}$ is S or T;
each of $X_8$ and $X_{82}$ is G, N, Q, P, S, or T;
each of $X_9$, $X_{52}$, and $X_{60}$ is A, V, I, L, P, R, H, K, S, or T;
each of $X_{10}$, $X_{97}$, and $X_{102}$ is G, A, V, I, L, F, Y, W, S, or T;
each of $X_{11}$, $X_{15}$, $X_{21}$, $X_{42}$, $X_{50}$, and $X_{101}$ is A, V, I, L, M, P, F, Y, or W;
each of $X_{12}$, $X_{13}$, $X_{25}$, $X_{29}$, $X_{49}$, and $X_{57}$ is A, V, I, L, C, S, or T;
each of $X_{17}$, $X_{27}$, $X_{48}$, $X_{85}$, and $X_{96}$ is G, D, E, N, or Q;
each of $X_{18}$ and $X_{109}$ is P, R, H, or K;
each of $X_{20}$, $X_{24}$, $X_{45}$, $X_{46}$, and $X_{80}$ is P, R, H, K, S, or T;
each of $X_{28}$, $X_{66}$, $X_{71}$, and $X_{75}$ is G, D, E, S, or T;
$X_{30}$ is G, A, V, I, L, or absent;
$X_{31}$ is D, E, F, Y, W, S, T, or absent;
$X_{32}$ is N, Q, S, T, or absent;
each of $X_{33}$ or $X_{35}$ is N, Q, R, H, K, or absent;
$X_{34}$ is G, S, T, or absent;
each of $X_{36}$, $X_{38}$, and $X_{100}$ is G, P, F, Y, W, R, H, K, S, T, or absent;
$X_{37}$ is D, E, N, Q, S, T, or absent;
each of $X_{40}$, $X_{55}$, $X_{56}$, $X_{61}$, $X_{86}$, and $X_{98}$ is any amino acid (e.g., A, V, I, L, N, Q, F, Y, W, R, H, or K; M, F, Y, W, R, H, K, S, or T; G, A, V, I, L, F, Y, W, R, H, K, S, or T; G, A, V, I, L, M, D, E, N, Q, F, Y, W, R, H, or K; G, A, V, I, L, N, Q, P, S, or T; N, Q, F, Y, W, R, H, K, S, or T; or D, E, R, H, K, S, or T);
each of $X_{47}$, $X_{59}$, $X_{83}$, $X_{95}$, and $X_{99}$ is G, D, E, N, Q, R, H, K, S, or T;
each of $X_{51}$ and $X_{92}$ is F, Y, W, R, H, or K;
each of $X_{77}$ and $X_{93}$ is F, Y, or W; and
each of $X_{91}$ and $X_{111}$ is A, V, I, L, D, E, S, or T.

In other embodiments, each X in SEQ ID NO:59 can be an amino acid (or a conservative amino acid substitution thereof) in any one of SEQ ID NOs:50-58 when any one of the sequences in SEQ ID NOs:50-58 is used as a reference sequence to be optimally aligned with SEQ ID NO:59.

In some embodiments, the LC variable region includes a first CDR including SEQ ID NO:60, a second CDR including SEQ ID NO:61, and a third CDR including SEQ ID NO:62:

(SEQ ID NO: 60)
$X_1X_2X_3X_4X_5X_6X_7X_8X_9X_{10}X_{11}X_{12}$, (SEQ ID NO: 61)
$X_{13}X_{14}X_{15}$, and (SEQ ID NO: 62)
$X_{16}X_{17}X_{18}X_{19}X_{20}X_{21}X_{22}X_{23}T$, wherein:
each of $X_1$ and $X_{17}$ is D, E, N, or Q;
$X_2$ is G, D, E, S, or T;
each $X_3$ and $X_{14}$ is A, V, I, L, C, S, or T;
$X_4$ is G, A, V, I, L, or absent;
$X_5$ is D, E, F, Y, W, S, T, or absent;
each of $X_6$ and $X_{11}$ is D, E, N, Q, S, T, or absent;
each of $X_7$ or $X_9$ is N, Q, R, H, K, or absent;
$X_8$ is G, S, T, or absent;
each of $X_{10}$ and $X_{12}$ is G, F, Y, W, R, H, K, S, T, or absent;
$X_{13}$ is G, A, V, I, L, F, Y, W, R, H, K, S, or T;
$X_{15}$ is S or T;
$X_{16}$ is D, E, N, Q, R, H, or K;
$X_{20}$ is D, E, N, Q, R, H, K, S, or T;
$X_{18}$ is G, F, Y, W, S, or T;
$X_{23}$ is A, V, I, L, F, Y, W, S, or T;
$X_{19}$ is D, E, N, Q, F, Y, W, R, H, K, S, or T;
$X_{21}$ is P, F, Y, W, R, H, K, S, or T; and
$X_{22}$ is M, P, F, Y, or W.

In other embodiments, each X in SEQ ID NOs:60-62 can be an amino acid (or a conservative amino acid substitution thereof) in any one of SEQ ID NOs:50-58 when any one of the sequences in SEQ ID NOs:50-58 is used as a reference sequence to be optimally aligned with SEQ ID NOs:60-62, respectively.

In some embodiments, the LC variable region includes or is a polypeptide sequence having at least 90% sequence identity to SEQ ID NO:63:

$DX_2X_3X_4X_5QX_7X_8X_9X_{10}LX_{12}X_{13}X_{14}X_{15}GX_{17}X_{18}X_{19}X_{20}X_{21}SCX_{24}X_{25}SQX_{28}X_{29}X_{30}X_{31}X_{32}X_{33}X_{34}$ $X_{35}X_{36}X_{37}X_{38}X_{39}X_{40}WX_{42}X_{43}QX_{45}X_{46}X_{47}X_{48}X_{49}X_{50}X_{51}X_{52}LIX_{55}X_{56}X_{57}SX_{59}X_{60}X_{61}SGX_{64}PX_{66}$

-continued

RFX$_{69}$GSGSGTDX$_{77}$X$_{78}$LX$_{80}$IX$_{82}$X$_{83}$X$_{84}$X$_{85}$X$_{86}$EDX$_{89}$X$_{90}$X$_{91}$X$_{92}$X$_{93}$CX$_{95}$QX$_{97}$X$_{98}$X$_{99}$X$_{100}$X$_{101}$

X$_{102}$TFGX$_{106}$GTKLEX$_{112}$KR wherein:
  each of X$_2$, X$_4$, X$_{13}$, X$_{19}$, X$_{29}$, X$_{39}$, X$_{64}$, X$_{84}$, X$_{89}$, X$_{90}$, X$_{106}$, and X$_{112}$ is G, A, V, I, L, or M;
  each of X$_3$ and X$_{43}$ is G, A, V, I, L, N, or Q;
  each of X$_5$, X$_7$, X$_{14}$, X$_{49}$, X$_{69}$, and X$_{78}$ is S or T;
  each of X$_8$ and X$_{20}$ is P, S, or T;
  each of X$_9$, X$_{10}$, X$_{12}$, X$_{25}$, and X$_{57}$ is A, V, I, L, S, or T;
  each of X$_{15}$, X$_{21}$, X$_{42}$, X$_{50}$, and X$_{101}$ is A, V, I, L, M, P, F, Y, or W;
  each of X$_{17}$, X$_{47}$, X$_{48}$, X$_{85}$, and X$_{96}$ is G, D, E, N, or Q;
  each of X$_{18}$ and X$_{46}$ is P, R, H, or K;
  each of X$_{24}$, X$_{45}$, and X$_{80}$ is P, R, H, K, S, or T;
  each of X$_{28}$ and X$_{66}$ is G, D, E, S, or T;
  X$_{30}$ is G, A, V, I, L, or absent;
  X$_{31}$ is D, E, F, Y, W, or absent;
  X$_{32}$ is S, T, or absent;
  each of X$_{33}$ and X$_{35}$ is N, Q, R, H, K, or absent;
  X$_{34}$ is G, S, T, or absent;
  X$_{36}$ is G, R, H, K, S, or T;
  X$_{37}$ is N, Q, S, or T;
  X$_{38}$ is F, Y, W, S, or T;
  X$_{40}$, X$_{52}$ is A, V, I, L, N, Q, R, H, or K;
  each of X$_{51}$, X$_{55}$, and X$_{92}$ is F, Y, W, R, H, or K;
  X$_{56}$ is A, V, I, L, F, Y, W, R, H, or K;
  X$_{59}$ is D, E, R, H, K, S, or T;
  X$_{60}$ is A, V, I, L, R, H, K, S, or T;
  X$_{61}$ is M, D, E, N, Q, R, H, or K;
  each of X$_{77}$ and X$_{93}$ is F, Y, or W;
  X$_{82}$ is N, Q, S, or T;
  X$_{83}$ is N, Q, R, H, K, S, or T;
  X$_{86}$ is A, V, I, L, N, Q, S, or T;
  X$_{91}$ is A, V, I, L, D, E, S, or T;
  X$_{95}$ is D, E, N, Q, R, H, or K;
  X$_{97}$ is G, F, Y, W, S, or T;
  X$_{98}$ is N, Q, F, Y, W, R, H, K, S, or T;
  X$_{99}$ is D, E, N, Q, R, H, K, S, or T;
  X$_{100}$ is P, F, Y, W, R, H, or K; and
  X$_{102}$ is A, V, I, L, F, Y, W, S, or T.
In other embodiments, each X in SEQ ID NO:63 can be an amino acid (or a conservative amino acid substitution thereof) in any one of SEQ ID NOs:50-54 when any one of the sequences in SEQ ID NOs:50-54 is used as a reference sequence to be optimally aligned with SEQ ID NO:63.

In yet other embodiments, the LC variable region includes or is a polypeptide sequence having at least 90% sequence identity to SEQ ID NO:64:

DIX$_3$X$_4$TQSX$_8$X$_9$X$_{10}$X$_{11}$SX$_{13}$X$_{14}$X$_{15}$GX$_{17}$RVX$_{20}$X$_{21}$X$_{22}$CX$_{24}$X$_{25}$SX$_{27}$X$_{28}$X$_{29}$X$_{30}$X$_{31}$X$_{32}$X$_{33}$X$_{34}$X$_{35}$

X$_{36}$X$_{37}$X$_{38}$X$_{39}$X$_{40}$WX$_{42}$QQX$_{45}$X$_{46}$X$_{47}$X$_{48}$X$_{49}$X$_{50}$X$_{51}$X$_{52}$LIX$_{55}$SX$_{56}$AX$_{58}$X$_{59}$X$_{60}$X$_{61}$X$_{62}$GX$_{64}$PX$_{66}$

RFX$_{69}$GX$_{71}$GSGX$_{75}$DFTLX$_{80}$IX$_{82}$X$_{83}$X$_{84}$X$_{85}$X$_{86}$EDX$_{89}$X$_{90}$X$_{91}$YX$_{93}$CQX$_{96}$X$_{97}$X$_{98}$X$_{99}$X$_{100}$PX$_{102}$

TFGX$_{106}$GTX$_{109}$LX$_{111}$X$_{112}$KR wherein:
  X$_3$ is G, A, V, I, L, N, or Q;
  each of X$_4$, X$_{39}$, X$_{64}$, X$_{84}$, X$_{89}$, X$_{90}$, X$_{106}$, and X$_{112}$ is G, A, V, I, L, or M;
  each of X$_8$ and X$_{82}$ is G, N, Q, P, S, or T;
  each of X$_9$, X$_{52}$, and X$_{60}$ is A, V, I, L, P, R, H, K, S, or T;

each of X$_{10}$, X$_{97}$, and X$_{102}$ is G, A, V, I, L, F, Y, W, S, or T;
  each of X$_{11}$, X$_{15}$, X$_{21}$, X$_{42}$, and X$_{50}$ is A, V, I, L, M, P, F, Y, or W;
  each of X$_{13}$, X$_{25}$, X$_{29}$, and X$_{49}$ is A, V, I, L, C, S, or T;
  each of X$_{14}$, X$_{22}$, X$_{58}$, X$_{62}$, and X$_{69}$ is S or T;
  each of X$_{17}$, X$_{27}$, X$_{48}$, X$_{85}$, and X$_{96}$ is G, D, E, N, or Q;
  each of X$_{20}$, X$_{24}$, X$_{45}$, X$_{46}$, and X$_{80}$ is P, R, H, K, S, or T;
  each of X$_{28}$, X$_{66}$, X$_{71}$, and X$_{75}$ is G, D, E, S, or T;
  X$_{30}$ is G, A, V, I, L, or absent;
  X$_{31}$ is D, E, F, Y, W, S, T, or absent;
  X$_{32}$ is N, Q, S, T, or absent;
  each of X$_{33}$ or X$_{35}$ is N, Q, R, H, K, or absent;
  X$_{34}$ is G, S, T, or absent;
  each of X$_{36}$, X$_{38}$, and X$_{100}$ is G, P, F, Y, W, R, H, K, S, T, or absent;
  X$_{37}$ is D, E, N, Q, S, T, or absent;
  each of X$_{40}$, X$_{55}$, X$_{56}$, X$_{61}$, X$_{86}$, and X$_{98}$ is any amino acid (e.g., A, V, I, L, N, Q, F, Y, W, R, H, or K; M, F, Y, W, R, H, K, S, or T; G, A, V, I, L, F, Y, W, R, H, K, S, or T; G, A, V, I, L, M, D, E, N, Q, F, Y, W, R, H, or K; G, A, V, I, L, N, Q, P, S, or T; N, Q, F, Y, W, R, H, K, S, or T; or D, E, R, H, K, S, or T);
  each of X$_{47}$, X$_{59}$, X$_{83}$, and X$_{99}$ is G, D, E, N, Q, R, H, K, S, or T;
  X$_{51}$ is F, Y, W, R, H, or K;
  each of X$_{91}$ and X$_{111}$ is A, V, I, L, D, E, S, or T;
  X$_{93}$ is F, Y, or W; and
  X$_{109}$ is P, R, H, or K.
In some embodiments, each X in SEQ ID NO:64 can be an amino acid (or a conservative amino acid substitution thereof) in any one of SEQ ID NOs:55-58 when any one of the sequences in SEQ ID NOs:55-58 is used as a reference sequence to be optimally aligned with SEQ ID NO:64.

In particular embodiments, the antibody further includes an LC constant region that includes or is a polypeptide sequence having at least 90% sequence identity to SEQ ID NO:74, in which each X in SEQ ID NO:74 can be any amino acid (e.g., a conservative amino acid substitution of an amino acid in any one of SEQ ID NOs:70-73 when any one of the sequences in SEQ ID NOs:70-73 is used as a reference sequence to be optimally aligned with SEQ ID NO:74). In other embodiments, each X in SEQ ID NO:74 can be an amino acid in any one of SEQ ID NOs:70-73 when any one of the sequences in SEQ ID NOs:70-73 is used as a reference sequence to be optimally aligned with SEQ ID NO:74.

Exemplary label agents include a capture agent (e.g., any herein), a detectable molecule or compound (e.g., a probe (e.g., a fluorescence resonance energy transfer or FRET probe, a fluorescent probe, and/or a quencher probe), an electroactive label, an electrocatalytic label, a fluorescent label, a fluorogenic probe (e.g., a non-fluorescent probe capable of being activated to produce a detectable fluorescent signal), a chromogenic label, a chromogenic probe (e.g., a non-chromogenic probe capable of being activated to produce a detectable chromogenic signal), a colorimetric label, a quantum dot, a particle, a nanoparticle, a microparticle, a barcode, a radio label (e.g., an RF label or barcode), a magnetic label, a magnetic field sensor active label (e.g., a giant magneto resistive (GMR) sensor label or an anisotropic magnetoresistor (AMR) sensor label), a spin label, an electron resonance active label (e.g., an electron paramagnetic resonance (EPR) active label of an electron spin resonance (ESR) active label), avidin, biotin, a tag, a dye, a marker, an enzyme that can optionally include one or more linking agents and/or one or more dyes, etc.), or a combination of a capture agent with a detectable molecule or a detectable compound. Other exemplary label agents include nucleic acid dyes, lipid dyes, etc.

The capture agent can include any useful reactive group (e.g., a functional group that is one of a cross-linker group, a binding group, or a click-chemistry group, such as any described herein). Exemplary reactive groups include any chemical group configured to form a bond. In general, a first chemical group reacts with a second chemical group to form a bond (e.g., a covalent bond), in which the first and second chemical groups form a reactive pair.

In one instance, the reactive group is a cross-linker group. In another non-limiting instance, the reactive pair is a cross-linker reaction pair, which includes a first cross-linker group and a second cross-linker group that reacts with that first cross-linker group. Exemplary cross-linker groups and cross-linker reaction pairs include those for forming a covalent bond between a carboxyl group (e.g., —$CO_2H$) and an amino group (e.g., —$NH_2$); or between a phospho group (e.g., —$P(O)(OH)_2$) and an amino group (e.g., —$NH_2$), such as 1-ethyl-3-(3-dimethylaminopropyl) carbodiimide (EDC) and dicyclohexylcarbodiimide (DCC), optionally used with N-hydroxysuccinimide (NHS) and/or N-hydroxysulfosuccinimide (sulfo-NHS). Other cross-linkers include those for forming a covalent bond between an amino group (e.g., —$NH_2$) and a thymine moiety, such as succinimidyl-[4-(psoralen-8-yloxy)]-butyrate (SPB); a hydroxyl group (e.g., —OH) and a sulfur-containing group (e.g., free thiol, —SH, sulfhydryl, cysteine moiety, or mercapto group), such as p-maleimidophenyl isocyanate (PMPI); between an amino group (e.g., —$NH_2$) and a sulfur-containing group (e.g., free thiol, —SH, sulfhydryl, cysteine moiety, or mercapto group), such as succinimidyl 4-(p-maleimidophenyl)butyrate (SMPB) and/or succinimidyl 4-(N-maleimidomethyl) cyclohexane-1-carboxylate (SMCC); between a sulfur-containing group (e.g., free thiol, —SH, sulfhydryl, cysteine moiety, or mercapto group) and a carbonyl group (e.g., an aldehyde group, such as for an oxidized glycoprotein carbohydrate), such as N-beta-maleimidopropionic acid hydrazide-trifluoroacetic acid salt (BMPH), 3-(2-pyridyldithio)propionyl hydrazide (PDPH), and/or a 3-(2-pyridyldithio)propionyl group (PDP); between a maleimide-containing group and a sulfur-containing group (e.g., free thiol, —SH, sulfhydryl, cysteine moiety, or mercapto group); between a sulfur-containing group (e.g., free thiol, —SH, sulfhydryl, cysteine moiety, or mercapto group) and an alkene group or an alkyne group; between a reactive carbene group (e.g., arising from photoactivation of a diazirine group) and a functional group having an active hydrogen group (e.g., as in an alkene group) and/or a nucleophilic group (e.g., as in a leaving group); and between a reactive nitrene group (e.g., arising from photoactivation of an aryl azide group) and a functional group having an active hydrogen group (e.g., as in an alkene group) and/or a nucleophilic group (e.g., as in a leaving group). Yet other cross-linkers include those for forming a covalent bond between two or more unsaturated hydrocarbon bonds, e.g., mediated by radical polymerization, such as a reaction of forming a covalent bond between a first alkene group and a second alkene group (e.g., a reaction between acrylate-derived monomers to form a polyacrylate, polyacrylamide, etc.). Other cross-linkers include those having photoactivatable groups, which upon photoreaction produces a reactive intermediate (e.g., such as cross-linkers including a benzophenone moiety, a diazirine moiety, or an aryl azide moiety).

In another instance, the reactive group is a binding group. In another non-limiting instance, the reactive pair is a binding reaction pair, which includes a first binding group and a second binding group that reacts with that first binding group. Exemplary binding groups and binding reaction pairs include those for forming a covalent bond between biotin and avidin, biotin and streptavidin, biotin and neutravidin, desthiobiotin and avidin (or a derivative thereof, such as streptavidin or neutravidin), hapten and an antibody, an antigen and an antibody, a primary antibody and a secondary antibody, lectin and a glycoprotein, and a nucleic acid and a complement thereof.

In yet another instance, the reactive group is a click-chemistry group. In another non-limiting instance, the reactive pair is a click-chemistry reaction pair, which includes a first click-chemistry group and a second click-chemistry group that reacts with that first click-chemistry group. Exemplary click-chemistry groups include, e.g., a click-chemistry group, e.g., one of a click-chemistry reaction pair selected from the group consisting of a Huisgen 1,3-dipolar cycloaddition reaction between an alkynyl group and an azido group to form a triazole-containing linker; a Diels-Alder reaction between a diene having a $4\pi$ electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a $2\pi$ electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group.

Other Reagents

The present device can be configured for use with any number of reagents either on-chip and/or off-chip. Exemplary reagents include a lysing agent (e.g., a detergent, such as saponin); a sterilization agent (e.g., a bleach, such as sodium hypochlorite or calcium hypochlorite; an oxidizer, such as chlorine dioxide, sodium dichloroisocyanurate, a peroxide, ethylene oxide, ozone gas, peracetic acid, hypochlorous acid, etc.; a surfactant, such as a cationic, anionic, nonionic, or zwitterionic surfactants, as well as combinations thereof; an antibiotic; a catalyst; an enzyme; a phage, e.g., a bacteriophage; a disinfectant, such as glutaraldehyde, stabilized hydrogen peroxide, peracetic acid, or formaldehyde; a biocide; an antiseptic; a detergent; a deodorant; and combinations thereof, where the sterilization agent can be in gas, liquid, semi-solid, or solid form, such as a powder, pellet, granule, gel, lyophilized, or freeze-dried forms), a detection agent (e.g., a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, a coated particle, etc.), a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes), an amplifying agent (e.g., a PCR agent, such as a polymerase, one or more deoxyribonucleotide triphosphates, a divalent metal (e.g., $MgCl_2$), a template DNA, a primer (e.g., for binding to a selective region of the target nucleic acid)), a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), an enzyme (e.g., that reacts with one or more markers, such as any described herein)), a buffer (e.g., a phosphate or borate buffer, which can optionally include one or more salts, kosmotropes, and/or chaotropes), an alcohol (e.g., from about 1% v/v to about 10% v/v methanol, ethanol, or isopropanol), a preservative (e.g., sucrose or trehalose), a blocking agent (e.g., gelatin, casein, bovine serum albumin, IgG, PVP, or PVA), a bead (e.g., a glass bead, silica bead, etc., such as to aid in mixing), etc., as well as combinations thereof.

Samples

The sample can include any useful targets. Exemplary targets include cells (e.g., white blood cells, red blood cells, neutrophils, lymphocytes, monocytes, granulocytes, tumor cells, etc.), viruses, viral proteins, bacteria, bacterial proteins, complexes, etc.

In some instances, the sample includes any useful test sample. The test sample can include any useful sample, such as a cell (e.g., a cell culture), tissue (e.g., tissue homogenates), a fluid, a swab, a biological sample (e.g., blood, such as whole blood, serum, plasma, saliva, urine, cerebral spine fluid, nasal fluid, tears, sweat, sputum, etc. from any subject, such as a human subject), a buffer, an environmental sample (e.g., air, soil, and/or water), etc. The sample can be optionally processed (e.g., on-chip or off-chip) in any useful manner (e.g., before or after transporting to the assay area, or even within the assay area), e.g., diluted, concentrated, mixed, homogenized, lysed, sterilized, incubated, labeled, etc.

Methods

The microfluidic devices and systems herein can be adapted for any useful diagnostic technique. Exemplary diagnostic techniques include cholinesterase inhibition assays, particle quantification (e.g., cell counting, differential white blood cell count), sedimentation assays, sandwich assay, nucleic acid assays, agglutination assays, toxin assays, amplification assays, etc.

In one non-limiting instance, the devices and systems herein are adapted to perform a method of conducting a sandwich assay. One exemplary method can include: providing a fluid sample in a channel on a microfluidic device (e.g., a microfluidic disc), the fluid sample including a plurality of particles (e.g., beads) having complexes formed thereon, individual ones of the complexes including a capture agent, a target (e.g., a target analyte), and a label agent, the fluid sample further including a free label agent; providing a density media from a media reservoir to an assay area (e.g., a detection region) of the microfluidic device by applying a first centrifugal force, the media reservoir on the microfluidic disc and in fluid communication with the assay area, the assay area fluidly coupled to the channel, where the density media has a density within a range, an upper bound of the range being lower than a density of the plurality of particles and a lower bound of the range being higher than a density of the fluid sample; transporting the plurality of particles including the complexes through the density media, where the free label agent is restricted from transport through the density media, and where a first plurality of particles having a first property is transported to a first distinct detection location in the assay area and a second plurality of beads having a second property different than the first property is transported to a second distinct detection location in the assay area; detecting a signal from the label agents of the complexes; and generating an electronic detection signal based, at least in part, on the signal detected from the label agents. The method can optionally include, prior to the transporting step, spinning the microfluidic device to apply a second centrifugal force on the plurality of particles, the first and second centrifugal forces being different.

In another non-limiting instance, the devices and systems herein are adapted to perform a method of conducting an assay (e.g., a sedimentation assay). An exemplary method can include: layering a mixture on a density medium in an assay area, where the mixture includes a sample, a first separation layer fluid, and a plurality of sedimentation particles, where the sedimentation particles have a density greater than the density medium, and where the layering a mixture includes forming, with the first separation layer fluid, an interface between the density medium and the sample, between the sample and the sedimentation particles, or between the density medium and the sedimentation particles; subjecting the mixture to a sedimentation force such that the sedimentation particles, if formed, travel through the first separation layer fluid and the density medium to a detection chamber; and detecting a presence of an analyte of interest in the detection chamber. Other exemplary assays (e.g., sandwich assays and sedimentation assays) are described in U.S. Pat. Nos. 8,945,914 and 8,962,346, each of which is incorporated herein by reference in its entirety.

In yet another non-limiting instance, the devices and systems herein are adapted to perform a method of conducting an agglutination assay. An exemplary method can include: layering a mixture on a density medium, where the mixture includes a sample and a first population of coated particles (e.g., coated beads) having a first density, where the first population includes a capture agent (e.g., an affinity reagent) for a target (e.g., an analyte of interest), where the first population is configured to form aggregates with the target when present, where the density medium has a minimum density greater than the first density; subjecting the mixture to a sedimentation force such that the aggregates, if formed, travel through the density medium; and detecting a presence of the aggregates in an assay area (e.g., a detection area, a detection chamber, or a detection region). Other exemplary agglutination assays are described in U.S. Pat. No. 9,244,065, which is incorporated herein by reference in its entirety.

In another non-limiting instance, the devices and systems herein are adapted to perform a method of conducting a toxin activity assay. An exemplary method can include: generating a plurality of complexes on a plurality of particles (e.g., beads) by action of an active toxin in a fluid sample, individual complexes of the plurality of complexes including a capture agent and a label agent; transporting the plurality of particles including the complexes through a density medium, where the density medium has a density lower than a density of the particles and higher than a density of the fluid sample, and where the transporting occurs, at least in part, by sedimentation; and detecting a signal from the label agents of the plurality of complexes bound to the plurality of particles. Other exemplary toxin activity assays are described in U.S. Pat. No. 9,304,128, which is incorporated herein by reference in its entirety.

In yet another non-limiting instance, the devices and systems herein are adapted to perform a method of conducting a metabolite test. An exemplary system can include: a chamber that includes a fluid, and is configured to accept a sample fluid, where the sample fluid includes a delta-9-THC compound and a metabolite (e.g., a cocaine-based compound, a methamphetamine-based compound, a methamphetamine compound, an amphetamine compound, an opiate-based compound, an MDMA-based compound, a ketamine-based compound, a PCP-based compound, a lysergic acid diethylamide-based compound, or a psilocybin-based compound); and a detection module that, responsive to a centrifugal force being applied to the fluid and the sample fluid, outputs an indication of a level of the delta-9-THC compound and/or the metabolite in the sample fluid.

An exemplary method can include: exposing an agent (e.g., a capture agent, a label agent, or a combination thereof, such as a fluorophore-labelled analyte specific antibody) to a first fluid including at least one of: a free analyte, where the free analyte, if present in the first fluid, originates from a test sample added to the first fluid; or a bound analyte, where the bound analyte, if present in the first fluid, is attached to a first particle having a first density, the agent has a stronger binding affinity for the free analyte than for the bound analyte, the first fluid is in a chamber, the chamber has an open end and a closed end and further includes a second liquid, the second liquid is located at the closed end of the chamber and the first liquid is located between the second liquid and the open end of the chamber; applying a centrifugal force to the chamber, wherein the first particle transfers from the first liquid to the second liquid; irradiating the second liquid to generate a detectable signal in the second liquid (e.g., with light energy to generate fluorescence in the second liquid); and quantifying an amount of free analyte in the second liquid based upon a magnitude of the detectable signal at the second liquid, where the quantification is based upon a threshold value. In some embodiments, the second liquid includes a colloidal suspension of silicon nanoparticles, dextran, poly(ethylene glycol), glycerol, sorbitol, iodixanol, cesium chloride, or perfluorodecalin.

Materials

The present devices and systems can be formed from any useful material. Exemplary materials include a polymer, such as polymethyl methacrylate (PMMA), polyethylene terephthalate (PET, e.g., biaxially-oriented PET or bo-PET), an acrylic polymer, poly(dimethylsiloxane) (PDMS), polycarbonate (PC), cyclo-olefin copolymer (COC), polyethylene terephthalate glycol (PETG), polyethylene (PE, such as branched homo-polymer PE), polyvinylchloride (PVC), polystyrene (PS), styrene copolymer, polyimide (PI), polypropylene (PP), polytetrafluoroethylene (PTFE), polynorbornene (PN), poly(4-methyl-1-pentene), silicone, and combinations or co-polymers thereof, silicon; glass; quartz; fused silica; an adhesive, such as any described herein; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organotin compounds), antioxidants (e.g., phenols or amines), and/or UV stabilizers (e.g., benzophenones or salicylates). Such materials can be provided in any useful form, such as in one or more layers that can be laminated to provide the assembled cartridge; and fabricated in any useful manner, such as by way of embossing, etching, injection molding, surface treatments, photolithography, bonding and other techniques.

EXAMPLES

Example 1: Detection of Cholinesterase Inhibition to Assess Chemical Agent Exposure We disclose a method to detect the inhibition of blood cholinesterase(s) to assess exposure to organophosphate chemical agents. Markers for exposure to chemical warfare agents are difficult to detect and unstable. Immunoassays can provide sensitive and specific detection of biomarkers of organophosphate (OP) nerve agent exposure. However, the specific nature of the assays could result in false negative results, e.g., if a subject has been exposed to an OP compound (e.g., nerve agent or pesticide) that is not included in a predetermined panel of assays, or if exposure is at a sufficiently low level such that an insufficient amount of OP adducts (e.g., OP adducts to human serum albumin, HSA) is present for detection.

For this reason, we developed a SpinDx-based assay to provide information on (non-specific) inhibition of cholinesterase (ChE), such that the SpinDx test at a minimum provides information similar to that which can be obtained with the existing Test-mate ChE test, but in a simpler, more portable format. The term "SpinDx-based assay," as used herein, refers to a bead-based assay format that employs a centrifugal microfluidic disc for transporting such beads (e.g., as described in FIG. 1A-1B and FIG. 3A-3D).

The goal for the SpinDx ChE assay is to provide percent inhibition of both acetylcholinesterase (AChE) and butyrylcholinesterase (BChE) leveraging the advantages of SpinDx: providing testing in a simple, easy-to-use format that simply requires addition of blood to the device, with all subsequent processing automated. In one non-limiting instance, we envision that the ChE assays would be packaged on the same device with the immunoassays, such that a single test provides both general information about ChE inhibition, and agent-specific information from the panel of immunoassays.

Any useful probe can be employed to detect ChE activity. In one non-limiting instance, the probe (also known as a substrate) is based upon Ellman's assay utilizing 5,5'-dithiobis(2-nitrobenzoic acid) (DTNB or Ellman's reagent) as a chromogenic probe to detect free thiols that are liberated upon ChE-mediated hydrolysis of acetylthiocholine (ASCh) or butyrylthiocholine (BSCh, thioester analogs of acetylcholine and butyrylcholine). Other thiol-sensitive probes besides DTNB are possible, and in particular several fluorogenic probes have been developed that undergo a large increase in fluorescence upon reaction with thiols. DTNB has been commonly used for historical reasons, but other probes including fluorogenic probes may be preferable for assays performed with blood (e.g., for the sake of reduced interference from hemoglobin absorbance).

In some non-limiting embodiments, the activity of a plurality of cholinesterases can be detected. For instance, activity of both AChE and BChE can be assayed. Both enzymes are present in whole blood, with AChE localized to erythrocytes and BChE localized to the serum. Generally, BChE is present at higher concentration in blood than AChE and may be easier to assay. To detect AChE from whole blood without interference from BChE, an inhibitor of BChE can be added. To detect BChE from whole blood without interference from AChE, a BChE-specific probe (e.g., BSCh) can be used. In either case, enzymatic hydrolysis of the probe liberates thiols, which react with a thiol-sensitive probe to result in a detectable signal (e.g., a rise or a change in absorbance at a particular wavelength, such as 450 nm for DTNB).

The baseline level of BChE in serum is subject to a higher degree of variability from person to person than AChE, and thus determination of a percent inhibition would normally require an initial, pre-exposure baseline measurement, the results of which may not always be available to medics performing a field-based assay for exposure. Meanwhile, AChE activity is relatively consistent from person to person, so long as it is normalized to hemoglobin content (i.e. to allow for variation in the erythrocyte content of a blood sample due to sampling technique, recent injury, or blood transfusion). Thus, in some non-limiting embodiments, the AChE activity measurement is normally preferred to BChE.

We disclose a pair of SpinDx assays for AChE and BChE that will be independent of the baseline (pre-exposure) activity, and capable of reporting directly the percent inhibition of ChE enzymes, relative to an on-board control assay. This can be achieved by coating beads with capture antibodies for either AChE or BChE, in limiting amount such that upon mixing with a blood sample, the beads become saturated with total AChE or BChE, including both active and OP-inactivated forms. Presuming the antibodies bind away from the active site of the enzymes, there will be no difference in capture efficiency between active and OP-inactivated forms of the enzymes.

Our SpinDx assay can include components for a fluorescent analog of the Ellman's assay, loaded within the density medium. Upon spinning the disk, the capture beads, but not the blood sample or erythrocytes, will partition into the density medium. The turnover of a probe (e.g., ASCh or BSCh) would thus be a function of the total AChE or BChE activity captured on the beads. Furthermore, turnover would be representative of the total fraction of non-inhibited AChE or BChE activity in the original sample.

As an example, consider a subject with a baseline BChE concentration of 50 nM in blood, and 40% inhibition (corresponding to 20 nM inactivated and 30 nM active BChE). Our assay would include sufficient antibody to capture up to 5 nM BChE (the actual level will be subject to optimization). In this hypothetical example, the capture beads would become saturated with 2 nM inactivated and 3 nM active BChE. Applying the same capture beads to a sample from different patient with a baseline BChE concentration of 80 nM, but the same 40% inhibition level, would still result in beads becoming saturated with 2 nM inactivated and 3 nM active BChE.

In an alternative format, SpinDx can be employed to simultaneously measure enzymatic activity in one channel and the AChE concentration in another channel by an immunoassay, thereby providing a specific activity (e.g., units/ng).

Example 2: Exemplary Cholinesterase Activity Assays in Clinical Matrices

Cholinesterase assays were performed in a variety of sample matrices other than blood, including fresh and frozen saliva. In particular, we focused on the AChE assay conducted in saliva, as BChE may be present at low and possibly undetectable levels in this clinical matrix.

We tested the assay extensively in buffer prior to translating to human bodily fluids, using either heat or paraoxon to inhibit the AChE cholinesterase activity. We determined that, in buffer, our limit of detection (LOD) for AChE with the SpinDx assay was between 0.005 and 0.01 mU/mL, with a limit of quantitation (LOQ) of 0.015 to 0.024 mU/mL, depending on the time of incubation (shorter incubations actually gave lower limits of detection and quantitation, perhaps because the fluorogenic assay inherently has a slow signal generation over time due to spontaneous hydrolysis of the substrate). For reference (see, e.g., Ahmadi-Motamayel F et al., "Evaluation of salivary acetylcholinesterase and pseudocholinesterase in patients with Alzheimer's disease: a case-control study," *Special Care Dentistry* 2019; 39(1):39-44), we anticipated AChE activity in saliva to be on the order of 20 U/L (corresponding to 20 mU/mL) and, thus, we expected that the activity should be within the range measurable by SpinDx.

Figure 4:
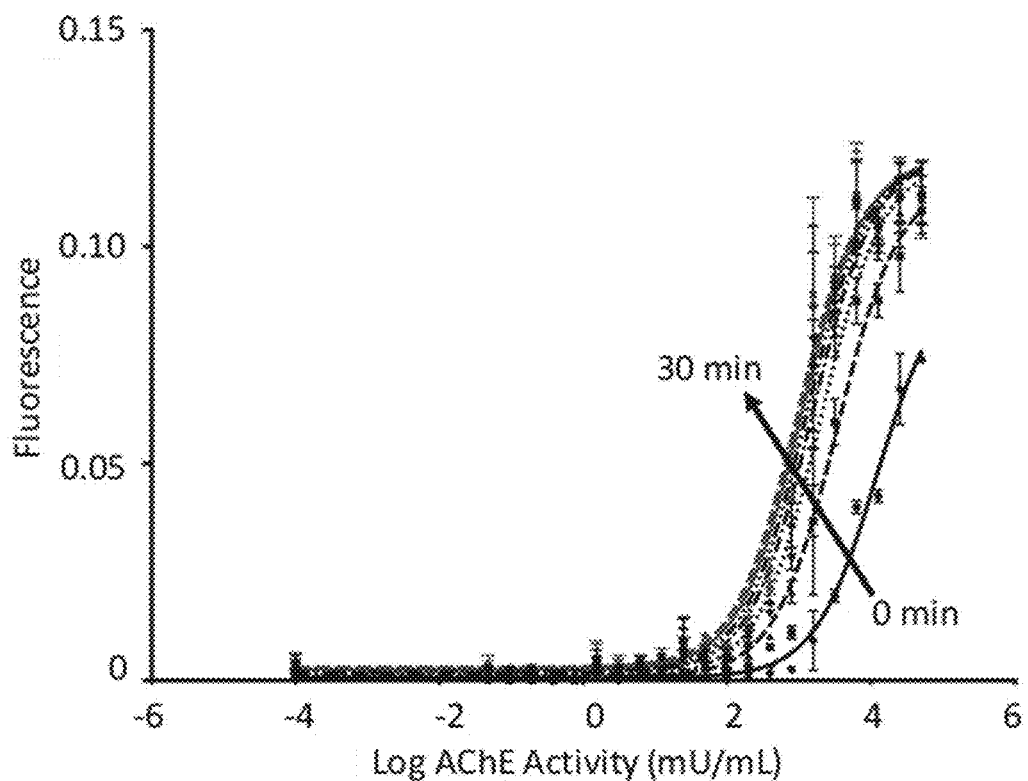
FIG. 4 shows measurement of AChE activity in buffer with SpinDx pulldown assay: dose response curves showing effect of different incubation times on the strength of signal.
Figure 5A:
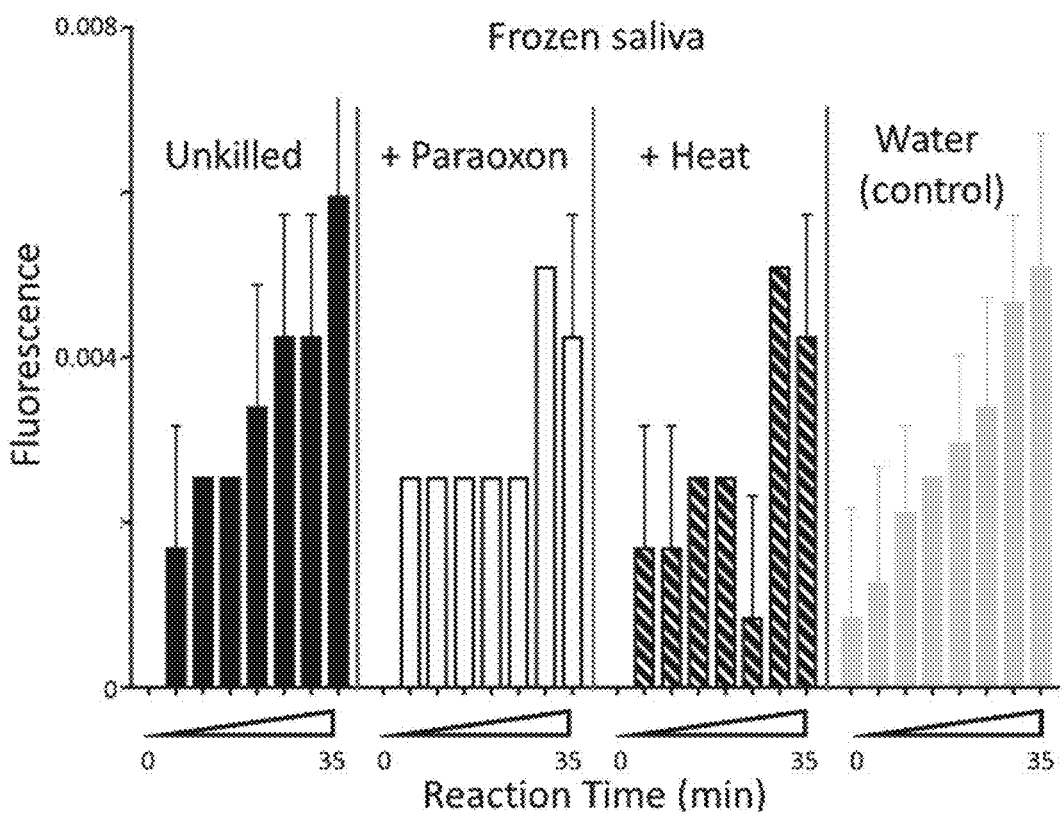
FIG. 5A-5F shows time course data of SpinDx assays for acetylcholinesterase activity in sample matrices including (A) pooled frozen human saliva, (B) fresh human saliva, (C) pooled human nasal fluid, (D) pooled human cerebrospinal fluid, (E) pooled human sweat, or (F) pooled human tears with or without inhibition of AChE by paraoxon or heat. Also provided are control experiments with water.
Figure 5B:
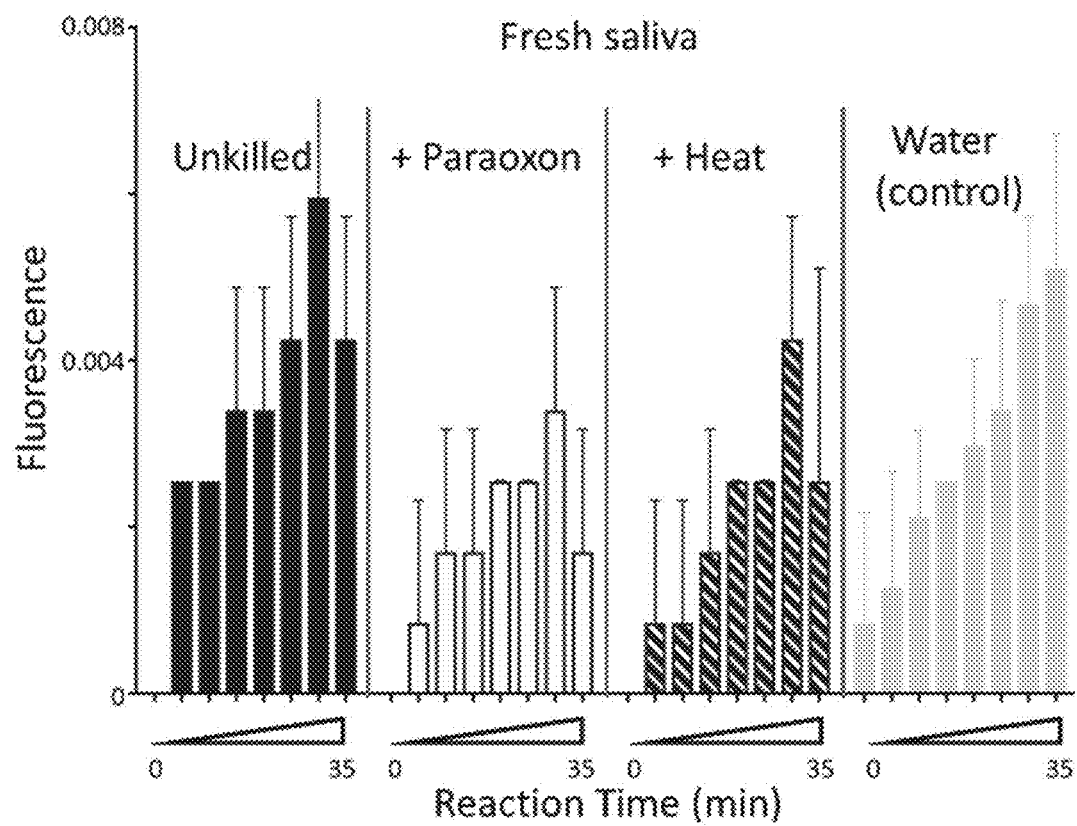
Figure 5C:
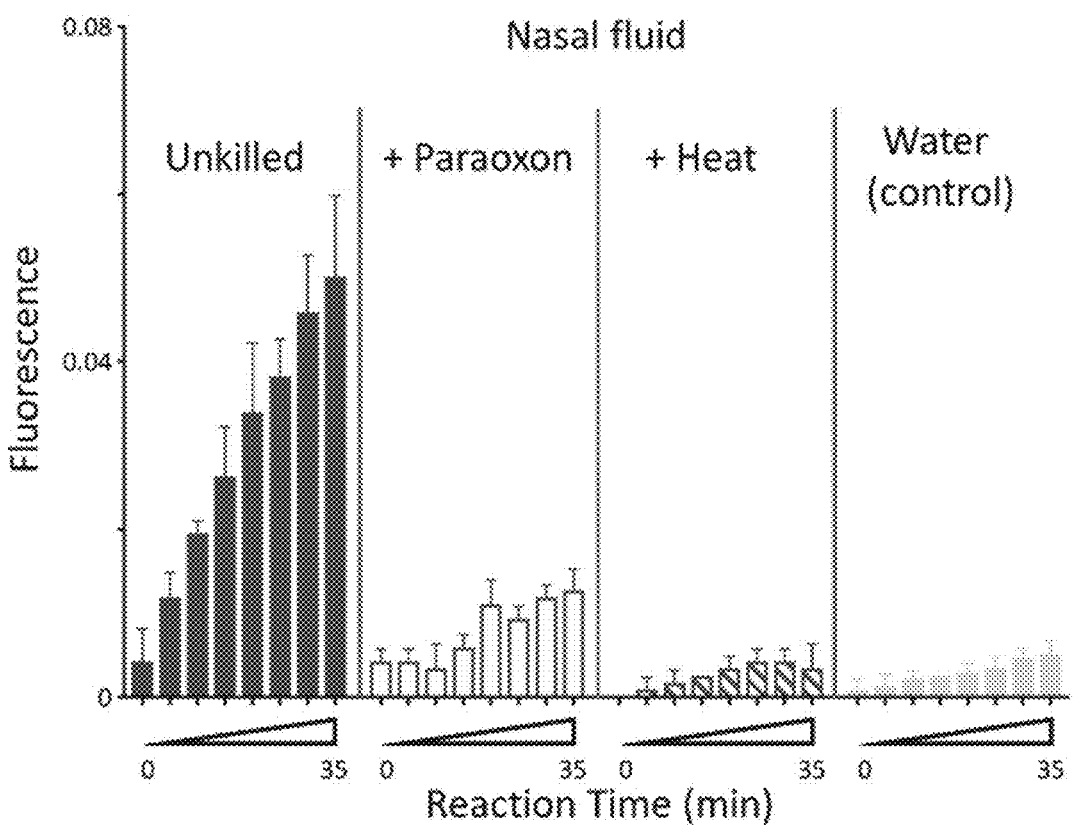
Figure 5D:
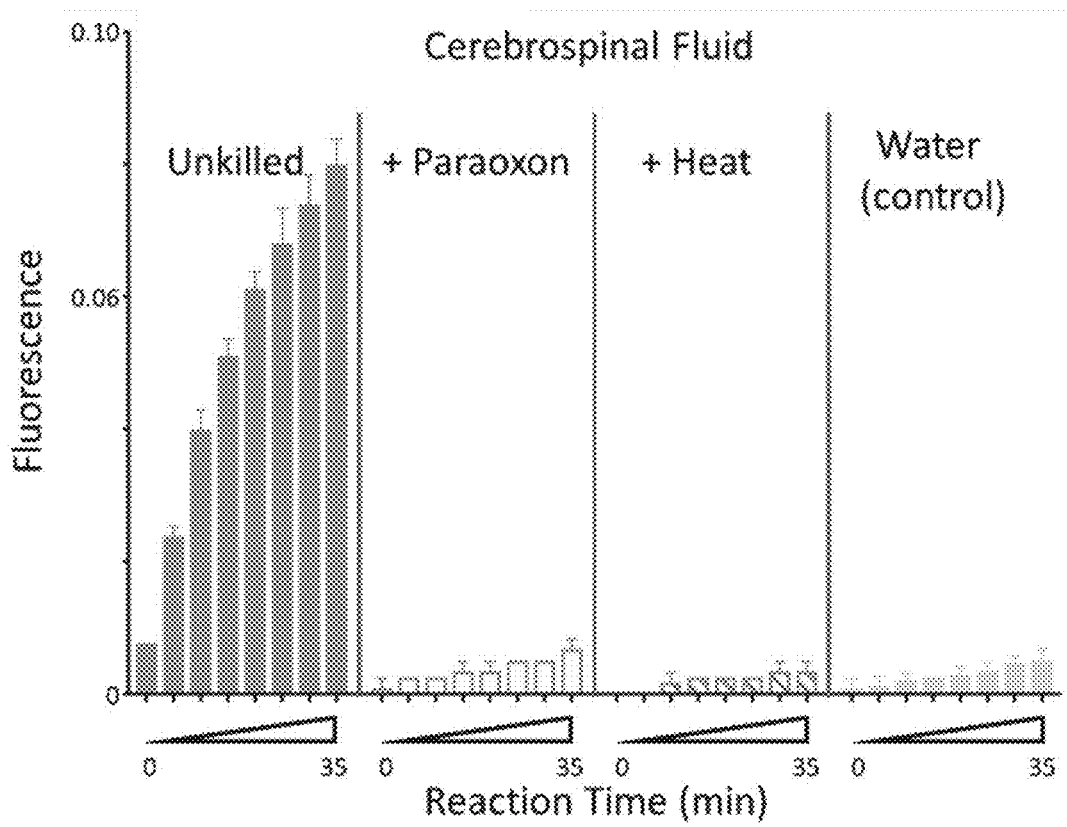
Figure 5E:
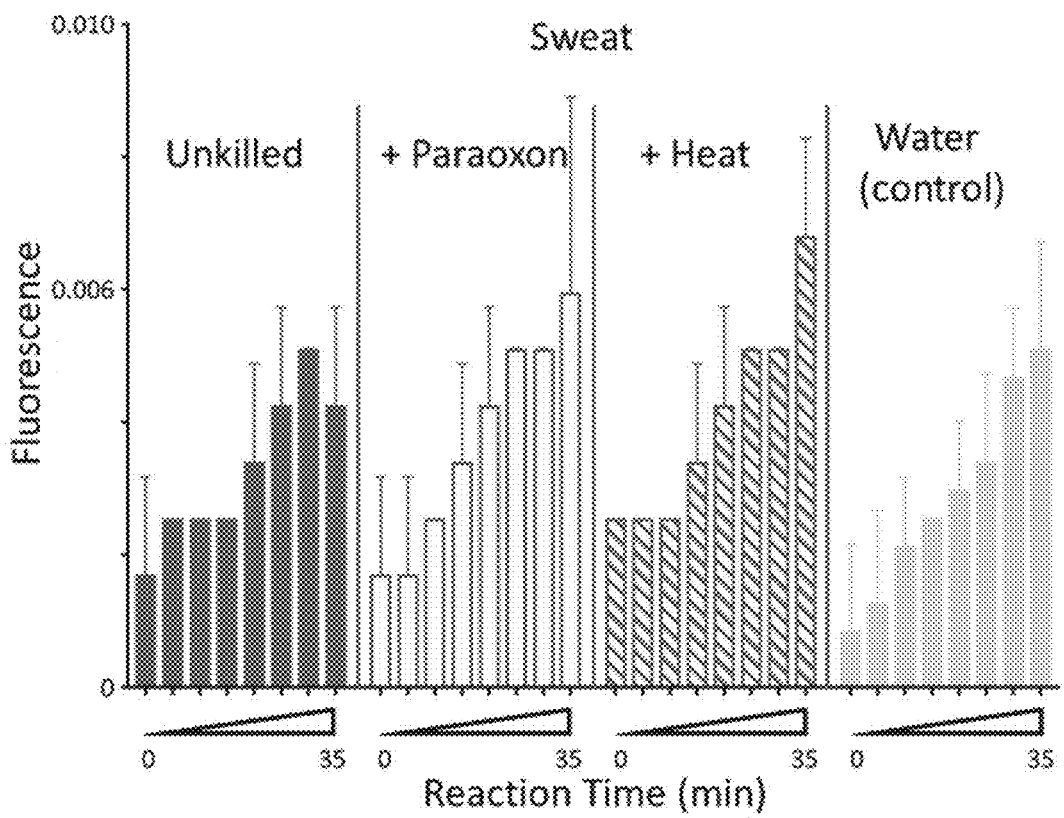
Figure 5F:
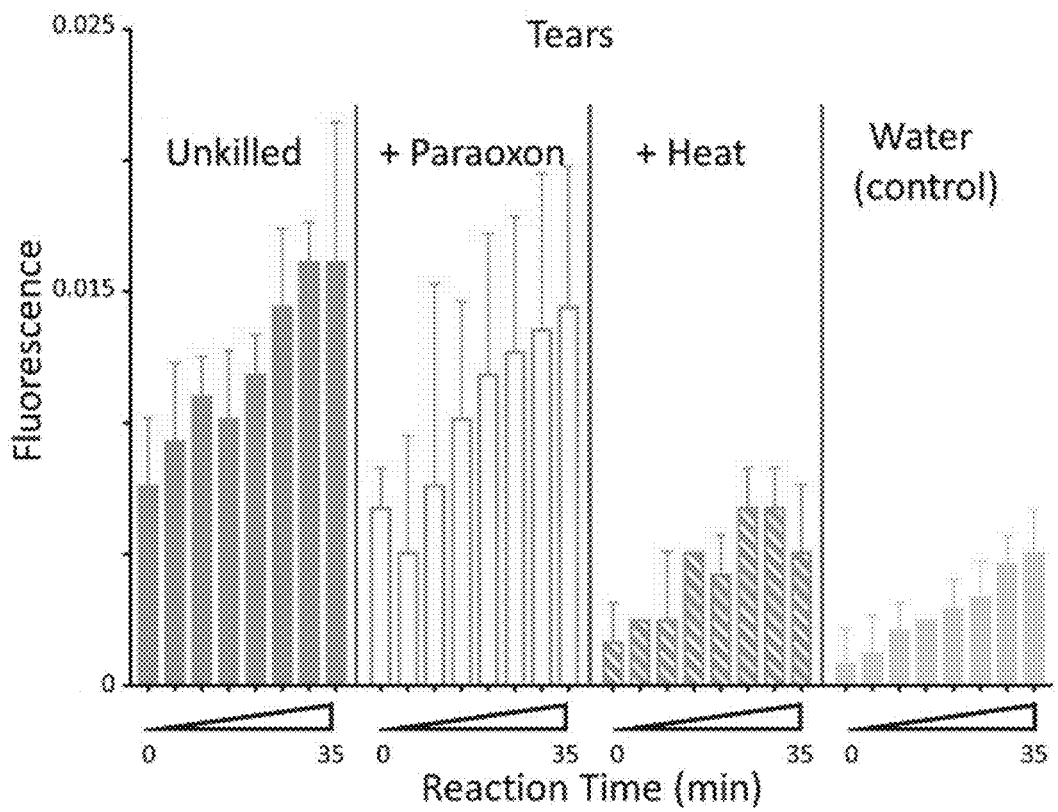

We do note that, as in FIG. 4, even at the level of 20 mU/mL, the signal is close to zero on the absolute scale of SpinDx's detector. We note too that, at this point that the dose-response curve in FIG. 4, the assay was not operating in the saturation regime that would be needed to get a baseline-independent "% activity" type of measurement at the levels expected in saliva. We did not, however, try titrating down the level of antibodies on the beads to achieve saturation, which is a possible approach to address this issue.

Further tests included use of human bodily fluids. For some fluid types, non-expired pooled specimens from a specimen bank (Innovative Research, Novi, Mich.) were employed. The fluid specimens included pooled human saliva, pooled human sweat, pooled human tears, pooled human nasal fluid, and pooled human cerebrospinal fluid (CSF). Fresh saliva samples were also collected for the purpose of testing the feasibility of an assay and then immediately discarded after testing.

Data for each sample matrix is shown in FIG. 5A-5F. To quickly summarize, we found that activity levels for fresh saliva, frozen saliva, and sweat were barely measurable, i.e., not discernibly different from a water control. We were able to measure cholinesterase activity in the nasal fluid, CSF, and tears. We note that activity in tears could not be reduced with paraoxon, suggesting that there may be another source of this activity (e.g., a different esterase that acts upon the acetylthiocholine substrate of our fluorogenic activity kit) or that another component in the tear fluid could be scavenging paraoxon.

Further work is required to develop this assay for use with saliva, sweat, or tears. Possible approaches for improvement include use of sample preparation to remove components that may be interacting with the cholinesterase inhibition assay; assessment of possible interference with the capture antibody employed on the bead, such as binding between the capture antibody with other non-ChE proteins or interferents in the sample matrix; determination of the most effective antibody in a particular sample matrix for use as the capture agent disposed on the bead; control of sample conditions, in which most samples were frozen and could have resulted in denaturing of ChE; determination of whether different splice variants or isoforms of ChE is present in particular sample matrices, which can inform the selection of the antibody for use as the capture agent; analysis of the types of esterase enzymes present in sample matrix, which may be cholinesterases or other types of esterase enzymes that exhibit activity with the probes employed in the inhibition assay;

and optimization of probe selection or probe structure to maximally react with certain esterases to distinguish between AChE, BChE, or other esterases.

Nasal fluid and CSF both display the expected behavior with the kill assay and are well within the range of measurement of the assay. Collection of CSF is invasive but would be a useful diagnostic sample for monitoring nerve agent effects within the CNS. Nasal fluid collection is fairly minimally invasive, and a swab-based sampling approach might be a useful alternative to blood for monitoring acetylcholinesterase (especially in the case of inhalation exposures).

Figure 6:
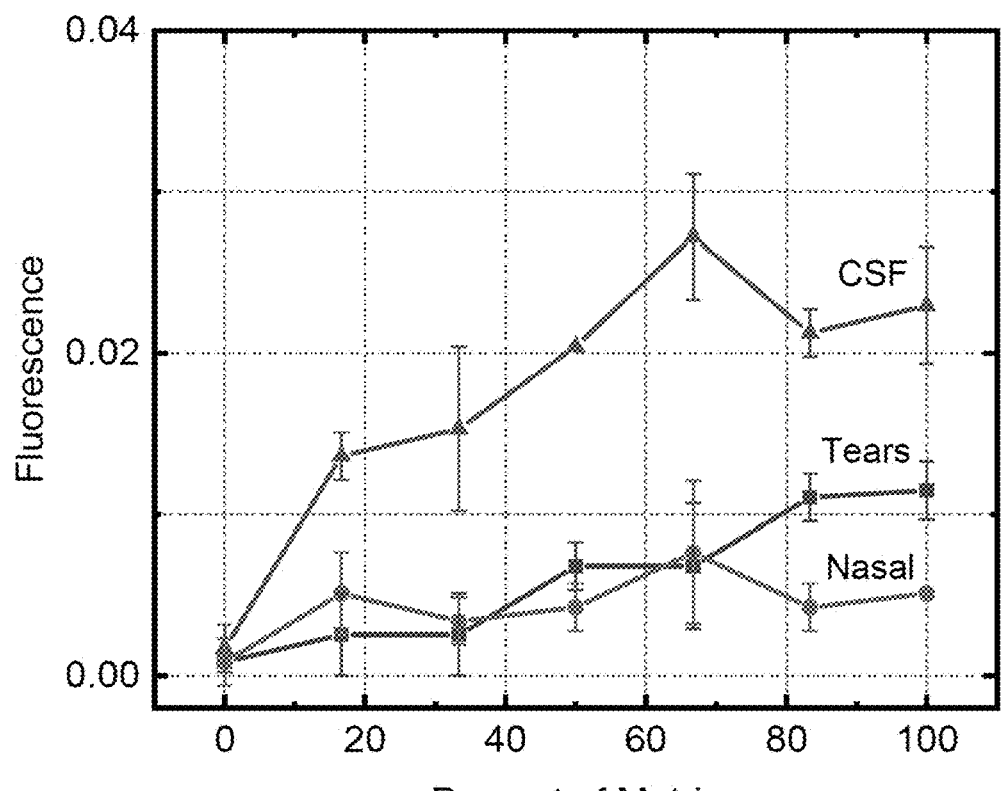
FIG. 6 shows a test of antibody saturation by diluting the sample matrices used as input to the assay in the range of 0 to 100%.

We further investigated whether we were truly achieving saturation of the antibodies for pulldown in these experiments by performing dilution series with each matrix. Results are shown in FIG. 6 for tears, nasal fluid, and CSF. Specifically, we show the 5 minute assay point, as this reduces the likelihood that saturation of the signal from the fluorogenic assay would confound detection of antibody saturation. Saturation of the antibodies in the dilution experiment would manifest as a flat (horizontal) line with similar signal generation across a wide range of sample concentration. In FIG. 6, we see a fairly monotonic increase (although not totally linear) over most of the range, showing that with none of these matrices are we achieving saturation of the antibodies. Both CSF and nasal fluid show some leveling off or even drop-off beyond 70% matrix although it would be difficult to rule out matrix-related assay inhibition with this experiment. Further studies can include optimizing the surface concentration of capture agents available for binding to ChE; determining whether sample preparation or processing (e.g., by way of diluting, concentrating, treating, etc.) affects antibody saturation; analyzing other sample matrices with higher concentrations of ChE (e.g., blood, plasma, etc.), etc.

Figure 7A:
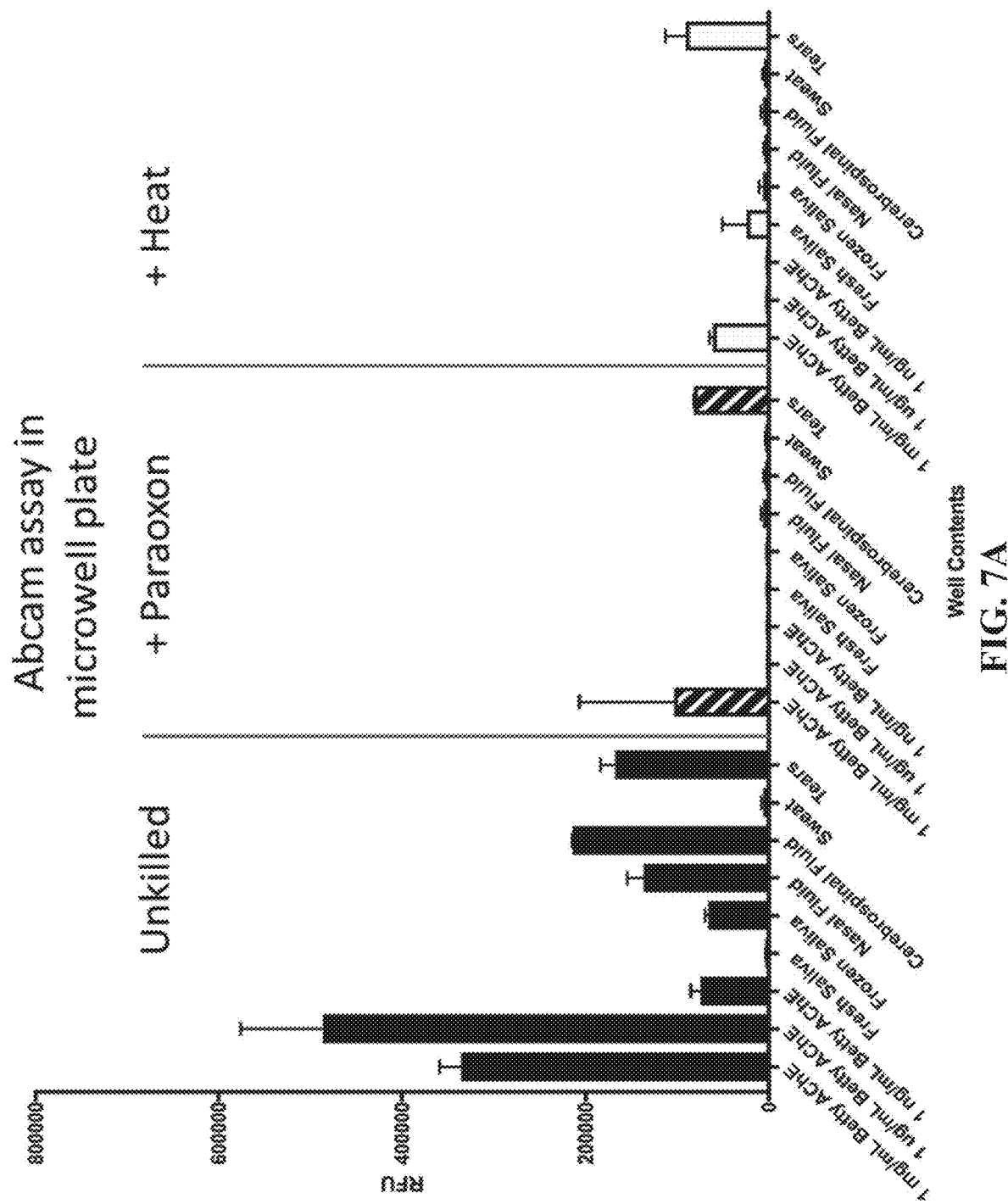
FIG. 7A-7B shows (A) a standard Abcam fluorescent AChE assay in a microplate and (B) a SpinDx pulldown AChE assay, which were performed with human sample matrices and recombinant AChE. Results are presented for intact (unkilled), paraoxon-killed, and heat-treated samples.
Figure 7B:
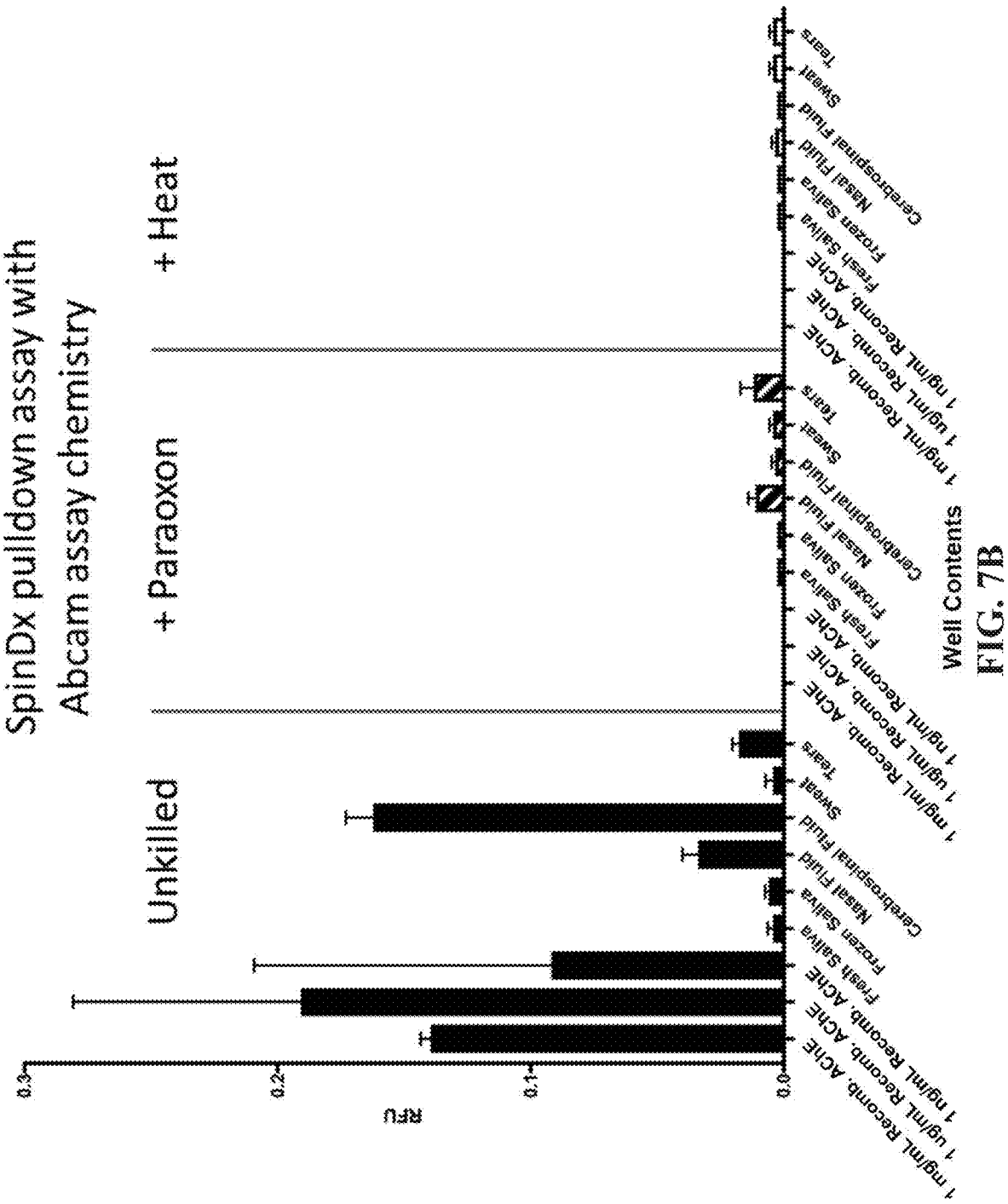

In addition, we performed side-by-side measurements of a series of samples including the human sample matrices and recombinantly expressed AChE with the SpinDx assay and with a traditional assay including a microtiter plate and plate reader (FIG. 7A-7B). The two assay formats show similar trends in the levels of activity, although certain samples (e.g., unkilled CSF) look dramatically higher in SpinDx than in the plate format. We note for example that both techniques corroborate that the apparent AChE activity of tears can't be killed by heat or paraoxon, suggesting that there is another mechanism other than AChE or BChE in tears giving rise to a signal in this assay.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of conducting a cholinesterase inhibition assay, the method comprising:

generating a plurality of beads in a fluid sample, wherein each bead of the plurality of beads comprises: (i) a first population of a plurality of complexes comprising a capture agent and an activated cholinesterase and (ii) a second population of a plurality of complexes comprising a capture agent and an inactivated cholinesterase, such that each bead comprises both inactivated cholinesterase and activated cholinesterase;

transporting the plurality of beads including the complexes through a density medium in a detection chamber, wherein the density medium is characterized by a density that is less than a density of the plurality of beads and more than a density of the fluid sample, and wherein the transporting occurs, at least in part, by sedimentation; and detecting a presence or an absence of a first signal from the activated cholinesterase in the detection chamber, wherein the first signal arises from reacting the activated cholinesterase with a first probe and an optional second probe;

wherein an amount of capture agent disposed on a surface of each bead comprises a surface concentration configured to be saturated upon mixing with the fluid sample, thereby directly providing percent inhibition of cholinesterase that is independent of baseline, pre-exposure activity.

2. The method of claim 1, further comprising, before or after the transporting step:

binding a detection antibody to one or more of the plurality of complexes on the plurality of beads, thereby providing one or more detectable complexes.

3. The method of claim 2, further comprising, after said binding:

detecting a second signal from the detection antibody of the one or more detectable complexes bound to the plurality of beads.

4. The method of claim 1, wherein the activated or inactivated cholinesterase is an acetylcholinesterase or a butyrylcholinesterase.

5. The method of claim 1, wherein the inactivated cholinesterase is an acetylcholinesterase or a butyrylcholinesterase bound to an organophosphorous agent.

6. The method of claim 1, wherein the capture agent binds to both the activated cholinesterase and the inactivated cholinesterase.

7. The method of claim 2, wherein the detection antibody binds to both the activated cholinesterase and the inactivated cholinesterase.

8. The method of claim 1, wherein the first probe and/or the second probe, if present, comprises a compound of formula (I), (Ia), (IV), (VI), (VIa), or (VIII), or a salt thereof.

9. The method of claim 1, wherein the detection chamber is disposed within a substrate and the transporting step comprises spinning the substrate.

10. The method of claim 1, wherein the fluid sample comprises a nasal fluid or a cerebrospinal fluid.

* * * * *

SEQUENCE LISTING

```
<160> NUMBER OF SEQ ID NOS: 75

<210> SEQ ID NO 1
<211> LENGTH: 14
<212> TYPE: PRT
<213> ORGANISM: Artificial Sequence
<220> FEATURE:
<223> OTHER INFORMATION: Synthetic construct

<400> SEQUENCE: 1

Gln Phe Asp His Tyr Ser Lys Gln Asp Arg Cys Ser Asp Leu
1               5                   10

<210> SEQ ID NO 2
<211> LENGTH: 614
<212> TYPE: PRT
<213> ORGANISM: Artificial Sequence
<220> FEATURE:
<223> OTHER INFORMATION: Synthetic construct

<400> SEQUENCE: 2

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60
```

```
Gly Ile Pro Phe Ala Glu Pro Pro Met Gly Pro Arg Arg Phe Leu Pro
 65                  70                  75                  80

Pro Glu Pro Lys Gln Pro Trp Ser Gly Val Val Asp Ala Thr Thr Phe
             85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
                180                 185                 190

Pro Gly Ser Arg Glu Ala Pro Gly Asn Val Gly Leu Leu Asp Gln Arg
            195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
        275                 280                 285

Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
                340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
    370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
    435                 440                 445

Leu Ala Ala Gln Gly Ala Arg Val Tyr Ala Tyr Val Phe Glu His Arg
        450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
```

```
            485                 490                 495
Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
            515                 520                 525

Pro Gln Trp Pro Pro Tyr Thr Ala Gly Ala Gln Tyr Val Ser Leu
            530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
                580                 585                 590

Ser Tyr Met Val His Trp Lys Asn Gln Phe Asp His Tyr Ser Lys Gln
                595                 600                 605

Asp Arg Cys Ser Asp Leu
                610

<210> SEQ ID NO 3
<211> LENGTH: 602
<212> TYPE: PRT
<213> ORGANISM: Artificial Sequence
<220> FEATURE:
<223> OTHER INFORMATION: Synthetic construct

<400> SEQUENCE: 3

Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
                20                  25                  30

Ile Ile Ala Thr Lys Asn Gly Lys Val Arg Gly Met Asn Leu Thr Val
                35                  40                  45

Phe Gly Gly Thr Val Thr Ala Phe Leu Gly Ile Pro Tyr Ala Gln Pro
            50                  55                  60

Pro Leu Gly Arg Leu Arg Phe Lys Lys Pro Gln Ser Leu Thr Lys Trp
65              70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
                115                 120                 125

Ala Pro Lys Pro Lys Asn Ala Thr Val Leu Ile Trp Ile Tyr Gly Gly
            130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
                180                 185                 190

Asn Met Gly Leu Phe Asp Gln Gln Leu Ala Leu Gln Trp Val Gln Lys
                195                 200                 205

Asn Ile Ala Ala Phe Gly Gly Asn Pro Lys Ser Val Thr Leu Phe Gly
            210                 215                 220

Glu Ser Ala Gly Ala Ala Ser Val Ser Leu His Leu Leu Ser Pro Gly
```

225                 230                 235                 240
Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
                260                 265                 270

Asn Leu Ala Lys Leu Thr Gly Cys Ser Arg Glu Asn Glu Thr Glu Ile
                275                 280                 285

Ile Lys Cys Leu Arg Asn Lys Asp Pro Gln Glu Ile Leu Leu Asn Glu
            290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
                340                 345                 350

Glu Gly Thr Ala Phe Leu Val Tyr Gly Ala Pro Gly Phe Ser Lys Asp
                355                 360                 365

Asn Asn Ser Ile Ile Thr Arg Lys Glu Phe Gln Glu Gly Leu Lys Ile
            370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
                435                 440                 445

Phe Glu His Arg Ser Ser Lys Leu Pro Trp Pro Glu Trp Met Gly Val
            450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
                500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
            530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
            595                 600

<210> SEQ ID NO 4
<211> LENGTH: 614
<212> TYPE: PRT
<213> ORGANISM: Artificial Sequence
<220> FEATURE:
<223> OTHER INFORMATION: Synthetic construct

<400> SEQUENCE: 4

```
Met Arg Pro Pro Trp Tyr Pro Leu His Thr Pro Ser Leu Ala Phe Pro
1               5                   10                  15

Leu Leu Phe Leu Leu Leu Ser Leu Leu Gly Gly Gly Ala Arg Ala Glu
            20                  25                  30

Gly Arg Glu Asp Pro Gln Leu Leu Val Arg Val Arg Gly Gln Leu
        35                  40                  45

Arg Gly Ile Arg Leu Lys Ala Pro Gly Gly Pro Val Ser Ala Phe Leu
    50                  55                  60

Gly Ile Pro Phe Ala Glu Pro Pro Val Gly Ser Arg Arg Phe Met Pro
65                  70                  75                  80

Pro Glu Pro Lys Arg Pro Trp Ser Gly Val Leu Asp Ala Thr Thr Phe
                85                  90                  95

Gln Asn Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Ala Ser Pro Thr Pro
130                 135                 140

Val Leu Ile Trp Ile Tyr Gly Gly Gly Phe Tyr Ser Gly Ala Ala Ser
145                 150                 155                 160

Leu Asp Val Tyr Asp Gly Arg Phe Leu Ala Gln Val Glu Gly Ala Val
            165                 170                 175

Leu Val Ser Met Asn Tyr Arg Val Gly Thr Phe Gly Phe Leu Ala Leu
        180                 185                 190

Pro Gly Ser Arg Glu Ala Pro Gly Asn Val Gly Leu Leu Asp Gln Arg
    195                 200                 205

Leu Ala Leu Gln Trp Val Gln Glu Asn Ile Ala Ala Phe Gly Gly Asp
    210                 215                 220

Pro Met Ser Val Thr Leu Phe Gly Glu Ser Ala Gly Ala Ala Ser Val
225                 230                 235                 240

Gly Met His Ile Leu Ser Leu Pro Ser Arg Ser Leu Phe His Arg Ala
            245                 250                 255

Val Leu Gln Ser Gly Thr Pro Asn Gly Pro Trp Ala Thr Val Ser Ala
        260                 265                 270

Gly Glu Ala Arg Arg Arg Ala Thr Leu Leu Ala Arg Leu Val Gly Cys
    275                 280                 285

Pro Pro Gly Gly Ala Gly Gly Asn Asp Thr Glu Leu Ile Ala Cys Leu
290                 295                 300

Arg Thr Arg Pro Ala Gln Asp Leu Val Asp His Glu Trp His Val Leu
305                 310                 315                 320

Pro Gln Glu Ser Ile Phe Arg Phe Ser Phe Val Pro Val Val Asp Gly
            325                 330                 335

Asp Phe Leu Ser Asp Thr Pro Glu Ala Leu Ile Asn Thr Gly Asp Phe
        340                 345                 350

Gln Asp Leu Gln Val Leu Val Gly Val Val Lys Asp Glu Gly Ser Tyr
    355                 360                 365

Phe Leu Val Tyr Gly Val Pro Gly Phe Ser Lys Asp Asn Glu Ser Leu
370                 375                 380

Ile Ser Arg Ala Gln Phe Leu Ala Gly Val Arg Ile Gly Val Pro Gln
385                 390                 395                 400

Ala Ser Asp Leu Ala Ala Glu Ala Val Val Leu His Tyr Thr Asp Trp
            405                 410                 415
```

-continued

```
Leu His Pro Glu Asp Pro Thr His Leu Arg Asp Ala Met Ser Ala Val
            420                 425                 430

Val Gly Asp His Asn Val Val Cys Pro Val Ala Gln Leu Ala Gly Arg
        435                 440                 445

Leu Ala Ala Gln Gly Ala Arg Val Tyr Ala Tyr Ile Phe Glu His Arg
    450                 455                 460

Ala Ser Thr Leu Thr Trp Pro Leu Trp Met Gly Val Pro His Gly Tyr
465                 470                 475                 480

Glu Ile Glu Phe Ile Phe Gly Leu Pro Leu Asp Pro Ser Leu Asn Tyr
                485                 490                 495

Thr Thr Glu Glu Arg Ile Phe Ala Gln Arg Leu Met Lys Tyr Trp Thr
            500                 505                 510

Asn Phe Ala Arg Thr Gly Asp Pro Asn Asp Pro Arg Asp Ser Lys Ser
        515                 520                 525

Pro Gln Trp Pro Pro Tyr Thr Thr Ala Ala Gln Gln Tyr Val Ser Leu
    530                 535                 540

Asn Leu Lys Pro Leu Glu Val Arg Arg Gly Leu Arg Ala Gln Thr Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
        595                 600                 605

Glu Arg Cys Ser Asp Leu
    610

<210> SEQ ID NO 5
<211> LENGTH: 603
<212> TYPE: PRT
<213> ORGANISM: Artificial Sequence
<220> FEATURE:
<223> OTHER INFORMATION: Synthetic construct

<400> SEQUENCE: 5

Met Gln Thr Gln His Thr Lys Val Thr Gln Thr His Phe Leu Leu Trp
1               5                   10                  15

Ile Leu Leu Leu Cys Met Pro Phe Gly Lys Ser His Thr Glu Glu Asp
                20                  25                  30

Phe Ile Ile Thr Thr Lys Thr Gly Arg Val Arg Gly Leu Ser Met Pro
            35                  40                  45

Val Leu Gly Gly Thr Val Thr Ala Phe Leu Gly Ile Pro Tyr Ala Gln
    50                  55                  60

Pro Pro Leu Gly Ser Leu Arg Phe Lys Lys Pro Gln Pro Leu Asn Lys
65                  70                  75                  80

Trp Pro Asp Ile His Asn Ala Thr Gln Tyr Ala Asn Ser Cys Tyr Gln
                85                  90                  95

Asn Ile Asp Gln Ala Phe Pro Gly Phe Gln Gly Ser Glu Met Trp Asn
            100                 105                 110

Pro Asn Thr Asn Leu Ser Glu Asp Cys Leu Tyr Leu Asn Val Trp Ile
        115                 120                 125

Pro Val Pro Lys Pro Lys Asn Ala Thr Val Met Val Trp Ile Tyr Gly
    130                 135                 140

Gly Gly Phe Gln Thr Gly Thr Ser Ser Leu Pro Val Tyr Asp Gly Lys
145                 150                 155                 160
```

```
Phe Leu Ala Arg Val Glu Arg Val Ile Val Val Ser Met Asn Tyr Arg
                165                 170                 175

Val Gly Ala Leu Gly Phe Leu Ala Phe Pro Gly Asn Pro Asp Ala Pro
            180                 185                 190

Gly Asn Met Gly Leu Phe Asp Gln Gln Leu Ala Leu Gln Trp Val Gln
            195                 200                 205

Arg Asn Ile Ala Ala Phe Gly Gly Asn Pro Lys Ser Ile Thr Ile Phe
        210                 215                 220

Gly Glu Ser Ala Gly Ala Ala Ser Val Ser Leu His Leu Leu Cys Pro
225                 230                 235                 240

Gln Ser Tyr Pro Leu Phe Thr Arg Ala Ile Leu Glu Ser Gly Ser Ser
                245                 250                 255

Asn Ala Pro Trp Ala Val Lys His Pro Glu Glu Ala Arg Asn Arg Thr
            260                 265                 270

Leu Thr Leu Ala Lys Phe Thr Gly Cys Ser Lys Glu Asn Glu Met Glu
        275                 280                 285

Met Ile Lys Cys Leu Arg Ser Lys Asp Pro Gln Glu Ile Leu Arg Asn
    290                 295                 300

Glu Arg Phe Val Leu Pro Ser Asp Ser Ile Leu Ser Ile Asn Phe Gly
305                 310                 315                 320

Pro Thr Val Asp Gly Asp Phe Leu Thr Asp Met Pro His Thr Leu Leu
                325                 330                 335

Gln Leu Gly Lys Val Lys Lys Ala Gln Ile Leu Val Gly Val Asn Lys
            340                 345                 350

Asp Glu Gly Thr Ala Phe Leu Val Tyr Gly Ala Pro Gly Phe Ser Lys
        355                 360                 365

Asp Asn Asp Ser Leu Ile Thr Arg Lys Glu Phe Gln Glu Gly Leu Asn
    370                 375                 380

Met Tyr Phe Pro Gly Val Ser Arg Leu Gly Lys Glu Ala Val Leu Phe
385                 390                 395                 400

Tyr Tyr Val Asp Trp Leu Gly Glu Gln Ser Pro Glu Val Tyr Arg Asp
                405                 410                 415

Ala Leu Asp Asp Val Ile Gly Asp Tyr Asn Ile Ile Cys Pro Ala Leu
            420                 425                 430

Glu Phe Thr Lys Lys Phe Ala Glu Leu Glu Asn Asn Ala Phe Phe Tyr
        435                 440                 445

Phe Phe Glu His Arg Ser Ser Lys Leu Pro Trp Pro Glu Trp Met Gly
450                 455                 460

Val Met His Gly Tyr Glu Ile Glu Phe Val Phe Gly Leu Pro Leu Gly
465                 470                 475                 480

Arg Arg Val Asn Tyr Thr Arg Ala Glu Glu Ile Phe Ser Arg Ser Ile
                485                 490                 495

Met Lys Thr Trp Ala Asn Phe Ala Lys Tyr Gly His Pro Asn Gly Thr
            500                 505                 510

Gln Gly Asn Ser Thr Met Trp Pro Val Phe Thr Ser Thr Glu Gln Lys
        515                 520                 525

Tyr Leu Thr Leu Asn Thr Glu Lys Ser Lys Ile Tyr Ser Lys Leu Arg
    530                 535                 540

Ala Pro Gln Cys Gln Phe Trp Arg Leu Phe Phe Pro Lys Val Leu Glu
545                 550                 555                 560

Met Thr Gly Asp Ile Asp Glu Thr Glu Gln Glu Trp Lys Ala Gly Phe
                565                 570                 575
```

-continued

```
His Arg Trp Ser Asn Tyr Met Met Asp Trp Gln Asn Gln Phe Asn Asp
            580                 585                 590

Tyr Thr Ser Lys Lys Glu Ser Cys Thr Ala Leu
        595                 600

<210> SEQ ID NO 6
<211> LENGTH: 613
<212> TYPE: PRT
<213> ORGANISM: Artificial Sequence
<220> FEATURE:
<223> OTHER INFORMATION: Synthetic construct

<400> SEQUENCE: 6

Met Arg Pro Pro Trp Cys Pro Leu His Thr Pro Ser Leu Thr Pro Pro
1               5                   10                  15

Leu Leu Leu Leu Leu Phe Leu Ile Gly Gly Gly Ala Glu Ala Glu Gly
                20                  25                  30

Pro Glu Asp Pro Glu Leu Leu Val Met Val Arg Gly Gly Arg Leu Arg
            35                  40                  45

Gly Leu Arg Leu Met Ala Pro Arg Gly Pro Val Ser Ala Phe Leu Gly
        50                  55                  60

Ile Pro Phe Ala Glu Pro Pro Val Gly Pro Arg Arg Phe Leu Pro Pro
65                  70                  75                  80

Glu Pro Lys Arg Pro Trp Pro Gly Val Leu Asn Ala Thr Ala Phe Gln
                85                  90                  95

Ser Val Cys Tyr Gln Tyr Val Asp Thr Leu Tyr Pro Gly Phe Glu Gly
                100                 105                 110

Thr Glu Met Trp Asn Pro Asn Arg Glu Leu Ser Glu Asp Cys Leu Tyr
            115                 120                 125

Leu Asn Val Trp Thr Pro Tyr Pro Arg Pro Ser Ser Pro Thr Pro Val
        130                 135                 140

Leu Val Trp Ile Tyr Gly Gly Phe Tyr Ser Gly Ala Ser Ser Leu
145                 150                 155                 160

Asp Val Tyr Asp Gly Arg Phe Leu Thr Gln Ala Glu Gly Thr Val Leu
                165                 170                 175

Val Ser Met Asn Tyr Arg Val Gly Ala Phe Gly Phe Leu Ala Leu Pro
            180                 185                 190

Gly Ser Arg Glu Ala Pro Gly Asn Val Gly Leu Leu Asp Gln Arg Leu
        195                 200                 205

Ala Leu Gln Trp Val Gln Glu Asn Val Ala Phe Gly Gly Asp Pro
    210                 215                 220

Thr Ser Val Thr Leu Phe Gly Glu Ser Ala Gly Ala Ala Ser Val Gly
225                 230                 235                 240

Met His Leu Leu Ser Pro Pro Ser Arg Gly Leu Phe His Arg Ala Val
                245                 250                 255

Leu Gln Ser Gly Ala Pro Asn Gly Pro Trp Ala Thr Val Gly Val Gly
            260                 265                 270

Glu Ala Arg Arg Arg Ala Thr Leu Leu Ala Arg Leu Val Gly Cys Pro
        275                 280                 285

Pro Gly Gly Ala Gly Gly Asn Asp Thr Glu Leu Val Ala Cys Leu Arg
    290                 295                 300

Ala Arg Pro Ala Gln Asp Leu Val Asp His Glu Trp Arg Val Leu Pro
305                 310                 315                 320

Gln Glu Ser Val Phe Arg Phe Ser Phe Val Pro Val Val Asp Gly Asp
                325                 330                 335
```

```
Phe Leu Ser Asp Thr Pro Glu Ala Leu Ile Asn Ala Gly Asp Phe His
                340                 345                 350
Gly Leu Gln Val Leu Val Gly Val Val Lys Asp Glu Gly Ser Tyr Phe
            355                 360                 365
Leu Val Tyr Gly Ala Pro Gly Phe Ser Lys Asp Asn Glu Ser Leu Ile
        370                 375                 380
Ser Arg Ala Gln Phe Leu Ala Gly Val Arg Val Gly Val Pro Gln Ala
385                 390                 395                 400
Ser Asp Leu Ala Ala Glu Ala Val Val Leu His Tyr Thr Asp Trp Leu
                405                 410                 415
His Pro Glu Asp Pro Ala Arg Leu Arg Glu Ala Leu Ser Asp Val Val
            420                 425                 430
Gly Asp His Asn Val Val Cys Pro Val Ala Gln Leu Ala Gly Arg Leu
        435                 440                 445
Ala Ala Gln Gly Ala Arg Val Tyr Ala Tyr Ile Phe Glu His Arg Ala
    450                 455                 460
Ser Thr Leu Ser Trp Pro Leu Trp Met Gly Val Pro His Gly Tyr Glu
465                 470                 475                 480
Ile Glu Phe Ile Phe Gly Leu Pro Leu Glu Pro Ser Leu Asn Tyr Thr
                485                 490                 495
Ile Glu Glu Arg Thr Phe Ala Gln Arg Leu Met Arg Tyr Trp Ala Asn
            500                 505                 510
Phe Ala Arg Thr Gly Asp Pro Asn Asp Pro Arg Asp Pro Lys Ala Pro
        515                 520                 525
Gln Trp Pro Pro Tyr Thr Ala Gly Ala Gln Tyr Val Ser Leu Asn
    530                 535                 540
Leu Arg Pro Leu Glu Val Arg Arg Gly Leu Arg Ala Gln Ala Cys Ala
545                 550                 555                 560
Phe Trp Asn Arg Phe Leu Pro Lys Leu Leu Ser Ala Thr Asp Thr Leu
                565                 570                 575
Asp Glu Ala Glu Arg Gln Trp Lys Ala Glu Phe His Arg Trp Ser Ser
            580                 585                 590
Tyr Met Val His Trp Lys Asn Gln Phe Asp His Tyr Ser Lys Gln Asp
        595                 600                 605
Arg Cys Ser Asp Leu
    610

<210> SEQ ID NO 7
<211> LENGTH: 602
<212> TYPE: PRT
<213> ORGANISM: Artificial Sequence
<220> FEATURE:
<223> OTHER INFORMATION: Synthetic construct

<400> SEQUENCE: 7

Met Gln Ser Arg Ser Thr Val Ile Tyr Ile Arg Phe Val Leu Trp Phe
1               5                   10                  15
Leu Leu Leu Trp Val Leu Phe Glu Lys Ser His Thr Glu Glu Asp Ile
                20                  25                  30
Ile Ile Thr Thr Lys Asn Gly Lys Val Arg Gly Met His Leu Pro Val
            35                  40                  45
Leu Gly Gly Thr Val Thr Ala Phe Leu Gly Ile Pro Tyr Ala Gln Pro
        50                  55                  60
Pro Leu Gly Arg Leu Arg Phe Lys Lys Pro Gln Ser Leu Thr Lys Trp
65                  70                  75                  80
```

Pro Asp Ile Trp Asn Ala Thr Lys Tyr Ala Asn Ser Cys Tyr Gln Asn
                85                  90                  95

Thr Asp Gln Ser Phe Pro Gly Phe Leu Gly Ser Glu Met Trp Asn Pro
            100                 105                 110

Asn Thr Asp Leu Ser Glu Asp Cys Leu Tyr Leu Asn Val Trp Ile Pro
            115                 120                 125

Thr Pro Lys Pro Lys Asn Ala Thr Val Met Ile Trp Ile Tyr Gly Gly
        130                 135                 140

Ser Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
                180                 185                 190

Asn Val Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
        210                 215                 220

Glu Ser Ala Gly Ala Ala Ser Val Ser Leu His Leu Leu Ser Pro Glu
225                 230                 235                 240

Ser His Pro Leu Phe Thr Arg Ala Ile Leu Gln Ser Gly Ser Ser Asn
                245                 250                 255

Ala Pro Trp Ala Val Thr Ser Arg Tyr Glu Ala Arg Asn Arg Thr Leu
                260                 265                 270

Thr Leu Ala Lys Phe Ile Gly Cys Ser Arg Glu Asn Asp Thr Glu Ile
            275                 280                 285

Ile Lys Cys Leu Arg Asn Lys Asp Pro Gln Glu Ile Leu Arg His Glu
        290                 295                 300

Val Phe Val Val Pro Tyr Gly Thr Leu Leu Ser Val Asn Phe Gly Pro
305                 310                 315                 320

Thr Val Asp Gly Asp Phe Leu Thr Asp Met Pro Asp Thr Leu Leu Gln
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
            355                 360                 365

Asn Asn Ser Ile Ile Thr Arg Lys Glu Phe Gln Glu Gly Leu Lys Ile
        370                 375                 380

Phe Phe Pro Gly Val Ser Glu Phe Gly Lys Glu Ser Ile Leu Phe His
385                 390                 395                 400

Tyr Met Asp Trp Leu Asp Asp Gln Arg Ala Glu Lys Tyr Arg Glu Ala
                405                 410                 415

Leu Asp Asp Val Val Gly Asp Tyr Asn Ile Ile Cys Pro Ala Leu Glu
                420                 425                 430

Phe Thr Lys Lys Phe Ser Asp Met Gly Asn Asn Ala Phe Phe Tyr Tyr
            435                 440                 445

Phe Glu His Arg Ser Ser Lys Leu Pro Trp Pro Glu Trp Met Gly Val
        450                 455                 460

Met His Gly Tyr Glu Ile Glu Phe Val Phe Gly Leu Pro Leu Glu Arg
465                 470                 475                 480

Arg Val Asn Tyr Thr Lys Ala Glu Glu Ile Phe Ser Arg Ser Ile Met
                485                 490                 495

Lys Arg Trp Ala Asn Phe Ala Lys Tyr Gly Asn Pro Asn Gly Thr Gln

```
                500             505             510
Asn Asn Ser Thr Arg Trp Pro Val Phe Lys Ser Asn Glu Gln Lys Tyr
            515                 520                 525

Phe Thr Leu Asn Thr Glu Ser Pro Lys Val Asn Thr Lys Leu Arg Ala
            530                 535             540

Gln Gln Cys Arg Phe Trp Thr Leu Phe Phe Pro Lys Val Leu Glu Ile
545                 550                 555                 560

Thr Gly Asn Ile Asp Glu Val Glu Arg Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Ala Gly Leu
            595                 600

<210> SEQ ID NO 8
<211> LENGTH: 614
<212> TYPE: PRT
<213> ORGANISM: Artificial Sequence
<220> FEATURE:
<223> OTHER INFORMATION: Synthetic construct

<400> SEQUENCE: 8

Met Arg Pro Pro Trp Tyr Pro Leu His Thr Pro Ser Leu Ala Ser Pro
1               5                   10                  15

Leu Leu Phe Leu Leu Leu Ser Leu Leu Gly Gly Ala Arg Ala Glu
            20                  25                  30

Gly Arg Glu Asp Pro Gln Leu Leu Val Arg Val Arg Gly Gly Gln Leu
            35                  40                  45

Arg Gly Ile Arg Leu Lys Ala Pro Gly Gly Pro Val Ser Ala Phe Leu
        50                  55                  60

Gly Ile Pro Phe Ala Glu Pro Pro Val Gly Ser Arg Arg Phe Met Pro
65              70                  75                  80

Pro Glu Pro Lys Arg Pro Trp Ser Gly Ile Leu Asp Ala Thr Thr Phe
                85                  90                  95

Gln Asn Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Ile Trp Ile Tyr Gly Gly Phe Tyr Ser Gly Ala Ser Ser
145                 150                 155                 160

Leu Asp Val Tyr Asp Gly Arg Phe Leu Ala Gln Val Glu Gly Thr Val
                165                 170                 175

Leu Val Ser Met Asn Tyr Arg Val Gly Thr Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Ile Ala Ala Phe Gly Gly Asp
    210                 215                 220

Pro Met Ser Val Thr Leu Phe Gly Glu Ser Ala Gly Ala Ala Ser Val
225                 230                 235                 240

Gly Met His Ile Leu Ser Leu Pro Ser Arg Ser Leu Phe His Arg Ala
                245                 250                 255

Val Leu Gln Ser Gly Thr Pro Asn Gly Pro Trp Ala Thr Val Ser Ala
```

-continued

```
                260                 265                 270
Gly Glu Ala Arg Arg Ala Thr Leu Leu Ala Arg Leu Val Gly Cys
            275                 280                 285

Pro Pro Gly Gly Ala Gly Gly Asn Asp Thr Glu Leu Ile Ser Cys Leu
    290                 295                 300

Arg Thr Arg Pro Ala Gln Asp Leu Val Asp His Glu Trp His Val Leu
305                 310                 315                 320

Pro Gln Glu Ser Ile Phe Arg Phe Ser Phe Val Pro Val Val Asp Gly
                325                 330                 335

Asp Phe Leu Ser Asp Thr Pro Asp Ala Leu Ile Asn Thr Gly Asp Phe
            340                 345                 350

Gln Asp Leu Gln Val Leu Val Gly Val Val Lys Asp Glu Gly Ser Tyr
        355                 360                 365

Phe Leu Val Tyr Gly Val Pro Gly Phe Ser Lys Asp Asn Glu Ser Leu
    370                 375                 380

Ile Ser Arg Ala Gln Phe Leu Ala Gly Val Arg Ile Gly Val Pro Gln
385                 390                 395                 400

Ala Ser Asp Leu Ala Ala Glu Ala Val Val Leu His Tyr Thr Asp Trp
                405                 410                 415

Leu His Pro Glu Asp Pro Ala His Leu Arg Asp Ala Met Ser Ala Val
            420                 425                 430

Val Gly Asp His Asn Val Val Cys Pro Val Ala Gln Leu Ala Gly Arg
        435                 440                 445

Leu Ala Ala Gln Gly Ala Arg Val Tyr Ala Tyr Ile Phe Glu His Arg
    450                 455                 460

Ala Ser Thr Leu Thr Trp Pro Leu Trp Met Gly Val Pro His Gly Tyr
465                 470                 475                 480

Glu Ile Glu Phe Ile Phe Gly Leu Pro Leu Asp Pro Ser Leu Asn Tyr
                485                 490                 495

Thr Val Glu Glu Arg Ile Phe Ala Gln Arg Leu Met Gln Tyr Trp Thr
            500                 505                 510

Asn Phe Ala Arg Thr Gly Asp Pro Asn Asp Pro Arg Asp Ser Lys Ser
        515                 520                 525

Pro Arg Trp Pro Pro Tyr Thr Thr Ala Ala Gln Gln Tyr Val Ser Leu
    530                 535                 540

Asn Leu Lys Pro Leu Glu Val Arg Arg Gly Leu Arg Ala Gln Thr Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
        595                 600                 605

Glu Arg Cys Ser Asp Leu
    610
```

<210> SEQ ID NO 9

<400> SEQUENCE: 9

000

<210> SEQ ID NO 10
<211> LENGTH: 584
<212> TYPE: PRT

```
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (57)..(61)
<223> OTHER INFORMATION: Xaa can be any naturally occurring amino acid
<220> FEATURE:
<221> NAME/KEY: misc_feature
<222> LOCATION: (64)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (75)..(77)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
```

```
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (109)..(111)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(116)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (124)..(125)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (139)..(141)
<223> OTHER INFORMATION: Xaa can be any naturally occurring amino acid
<220> FEATURE:
<221> NAME/KEY: misc_feature
<222> LOCATION: (143)..(146)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(166)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (185)..(185)
```

```
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (210)..(211)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (215)..(217)
<223> OTHER INFORMATION: Xaa can be any naturally occurring amino acid
<220> FEATURE:
<221> NAME/KEY: misc_feature
<222> LOCATION: (219)..(220)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (238)..(242)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (248)..(250)
<223> OTHER INFORMATION: Xaa can be any naturally occurring amino acid
<220> FEATURE:
<221> NAME/KEY: misc_feature
<222> LOCATION: (253)..(255)
<223> OTHER INFORMATION: Xaa can be any naturally occurring amino acid
<220> FEATURE:
<221> NAME/KEY: misc_feature
<222> LOCATION: (258)..(264)
<223> OTHER INFORMATION: Xaa can be any naturally occurring amino acid
<220> FEATURE:
<221> NAME/KEY: misc_feature
```

```
<222> LOCATION: (266)..(267)
<223> OTHER INFORMATION: Xaa can be any naturally occurring amino acid
<220> FEATURE:
<221> NAME/KEY: misc_feature
<222> LOCATION: (269)..(271)
<223> OTHER INFORMATION: Xaa can be any naturally occurring amino acid
<220> FEATURE:
<221> NAME/KEY: misc_feature
<222> LOCATION: (275)..(278)
<223> OTHER INFORMATION: Xaa can be any naturally occurring amino acid
<220> FEATURE:
<221> NAME/KEY: misc_feature
<222> LOCATION: (280)..(284)
<223> OTHER INFORMATION: Xaa can be any naturally occurring amino acid
<220> FEATURE:
<221> NAME/KEY: misc_feature
<222> LOCATION: (286)..(287)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (291)..(298)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (309)..(309)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (313)..(314)
<223> OTHER INFORMATION: Xaa can be any naturally occurring amino acid
<220> FEATURE:
<221> NAME/KEY: misc_feature
<222> LOCATION: (316)..(318)
<223> OTHER INFORMATION: Xaa can be any naturally occurring amino acid
<220> FEATURE:
<221> NAME/KEY: misc_feature
<222> LOCATION: (320)..(324)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (336)..(337)
<223> OTHER INFORMATION: Xaa can be any naturally occurring amino acid
<220> FEATURE:
<221> NAME/KEY: misc_feature
<222> LOCATION: (343)..(343)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
```

```
<221> NAME/KEY: misc_feature
<222> LOCATION: (355)..(355)
<223> OTHER INFORMATION: Xaa can be any naturally occurring amino acid
<220> FEATURE:
<221> NAME/KEY: misc_feature
<222> LOCATION: (357)..(358)
<223> OTHER INFORMATION: Xaa can be any naturally occurring amino acid
<220> FEATURE:
<221> NAME/KEY: misc_feature
<222> LOCATION: (360)..(361)
<223> OTHER INFORMATION: Xaa can be any naturally occurring amino acid
<220> FEATURE:
<221> NAME/KEY: misc_feature
<222> LOCATION: (363)..(367)
<223> OTHER INFORMATION: Xaa can be any naturally occurring amino acid
<220> FEATURE:
<221> NAME/KEY: misc_feature
<222> LOCATION: (369)..(370)
<223> OTHER INFORMATION: Xaa can be any naturally occurring amino acid
<220> FEATURE:
<221> NAME/KEY: misc_feature
<222> LOCATION: (372)..(375)
<223> OTHER INFORMATION: Xaa can be any naturally occurring amino acid
<220> FEATURE:
<221> NAME/KEY: misc_feature
<222> LOCATION: (377)..(381)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (386)..(394)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(400)
<223> OTHER INFORMATION: Xaa can be any naturally occurring amino acid
<220> FEATURE:
<221> NAME/KEY: misc_feature
<222> LOCATION: (402)..(402)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (407)..(408)
<223> OTHER INFORMATION: Xaa can be any naturally occurring amino acid
<220> FEATURE:
<221> NAME/KEY: misc_feature
<222> LOCATION: (411)..(427)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (436)..(436)
<223> OTHER INFORMATION: Xaa can be any naturally occurring amino acid
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (441)..(441)
<223> OTHER INFORMATION: Xaa can be any naturally occurring amino acid
```

```
<220> FEATURE:
<221> NAME/KEY: misc_feature
<222> LOCATION: (446)..(446)
<223> OTHER INFORMATION: Xaa can be any naturally occurring amino acid
<220> FEATURE:
<221> NAME/KEY: misc_feature
<222> LOCATION: (454)..(454)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (460)..(463)
<223> OTHER INFORMATION: Xaa can be any naturally occurring amino acid
<220> FEATURE:
<221> NAME/KEY: misc_feature
<222> LOCATION: (467)..(468)
<223> OTHER INFORMATION: Xaa can be any naturally occurring amino acid
<220> FEATURE:
<221> NAME/KEY: misc_feature
<222> LOCATION: (470)..(479)
<223> OTHER INFORMATION: Xaa can be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (485)..(486)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (491)..(499)
<223> OTHER INFORMATION: Xaa can be any naturally occurring amino acid
<220> FEATURE:
<221> NAME/KEY: misc_feature
<222> LOCATION: (502)..(507)
<223> OTHER INFORMATION: Xaa can be any naturally occurring amino acid
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (511)..(512)
<223> OTHER INFORMATION: Xaa can be any naturally occurring amino acid
<220> FEATURE:
<221> NAME/KEY: misc_feature
<222> LOCATION: (514)..(523)
<223> OTHER INFORMATION: Xaa can be any naturally occurring amino acid
<220> FEATURE:
<221> NAME/KEY: misc_feature
<222> LOCATION: (527)..(528)
<223> OTHER INFORMATION: Xaa can be any naturally occurring amino acid
<220> FEATURE:
<221> NAME/KEY: misc_feature
<222> LOCATION: (530)..(530)
<223> OTHER INFORMATION: Xaa can be any naturally occurring amino acid
<220> FEATURE:
<221> NAME/KEY: misc_feature
<222> LOCATION: (533)..(534)
<223> OTHER INFORMATION: Xaa can be any naturally occurring amino acid
<220> FEATURE:
<221> NAME/KEY: misc_feature
<222> LOCATION: (536)..(536)
<223> OTHER INFORMATION: Xaa can be any naturally occurring amino acid
<220> FEATURE:
<221> NAME/KEY: misc_feature
<222> LOCATION: (539)..(539)
<223> OTHER INFORMATION: Xaa can be any naturally occurring amino acid
<220> FEATURE:
<221> NAME/KEY: misc_feature
<222> LOCATION: (541)..(542)
```

```
<223> OTHER INFORMATION: Xaa can be any naturally occurring amino acid
<220> FEATURE:
<221> NAME/KEY: misc_feature
<222> LOCATION: (544)..(546)
<223> OTHER INFORMATION: Xaa can be any naturally occurring amino acid
<220> FEATURE:
<221> NAME/KEY: misc_feature
<222> LOCATION: (549)..(549)
<223> OTHER INFORMATION: Xaa can be any naturally occurring amino acid
<220> FEATURE:
<221> NAME/KEY: misc_feature
<222> LOCATION: (551)..(552)
<223> OTHER INFORMATION: Xaa can be any naturally occurring amino acid
<220> FEATURE:
<221> NAME/KEY: misc_feature
<222> LOCATION: (556)..(556)
<223> OTHER INFORMATION: Xaa can be any naturally occurring amino acid
<220> FEATURE:
<221> NAME/KEY: misc_feature
<222> LOCATION: (561)..(562)
<223> OTHER INFORMATION: Xaa can be any naturally occurring amino acid
<220> FEATURE:
<221> NAME/KEY: misc_feature
<222> LOCATION: (565)..(566)
<223> OTHER INFORMATION: Xaa can be any naturally occurring amino acid
<220> FEATURE:
<221> NAME/KEY: misc_feature
<222> LOCATION: (568)..(568)
<223> OTHER INFORMATION: Xaa can be any naturally occurring amino acid
<220> FEATURE:
<221> NAME/KEY: misc_feature
<222> LOCATION: (572)..(572)
<223> OTHER INFORMATION: Xaa can be any naturally occurring amino acid
<220> FEATURE:
<221> NAME/KEY: misc_feature
<222> LOCATION: (574)..(575)
<223> OTHER INFORMATION: Xaa can be any naturally occurring amino acid
<220> FEATURE:
<221> NAME/KEY: misc_feature
<222> LOCATION: (578)..(580)
<223> OTHER INFORMATION: Xaa can be any naturally occurring amino acid
<220> FEATURE:
<221> NAME/KEY: misc_feature
<222> LOCATION: (582)..(583)
<223> OTHER INFORMATION: Xaa can be any naturally occurring amino acid

<400> SEQUENCE: 10

Glu Xaa Xaa Xaa Xaa Xaa Xaa Xaa Xaa Xaa Xaa Xaa Xaa Gly Xaa
1               5                   10                  15

Xaa Arg Gly Xaa Xaa Xaa Xaa Xaa Xaa Xaa Gly Xaa Val Xaa Ala Phe
                20                  25                  30

Leu Gly Ile Pro Xaa Ala Xaa Pro Pro Xaa Gly Xaa Xaa Arg Phe Xaa
            35                  40                  45

Xaa Pro Xaa Xaa Xaa Xaa Xaa Trp Xaa Xaa Xaa Xaa Xaa Ala Thr Xaa
50                  55                  60

Xaa Xaa Xaa Xaa Cys Xaa Gln Xaa Xaa Asp Xaa Xaa Xaa Pro Gly Phe
65                  70                  75                  80

Xaa Gly Xaa Glu Met Trp Asn Pro Asn Xaa Xaa Leu Ser Glu Asp Cys
                85                  90                  95

Leu Tyr Leu Asn Val Trp Xaa Pro Xaa Pro Xaa Xaa Xaa Thr
            100                 105                 110

Xaa Val Xaa Xaa Trp Ile Tyr Gly Gly Xaa Phe Xaa Xaa Gly Xaa Xaa
        115                 120                 125

Ser Leu Xaa Val Tyr Asp Gly Xaa Phe Leu Xaa Xaa Glu Xaa Xaa
            130                 135                 140

Xaa Xaa Val Ser Met Asn Tyr Arg Val Gly Xaa Xaa Gly Phe Leu Ala
145                 150                 155                 160

Xaa Pro Gly Xaa Xaa Xaa Ala Pro Gly Asn Xaa Gly Leu Xaa Asp Gln
```

```
            165                 170                 175
Xaa Leu Ala Leu Gln Trp Val Gln Xaa Asn Xaa Ala Ala Phe Gly Gly
            180                 185                 190

Xaa Pro Xaa Ser Xaa Thr Xaa Phe Gly Glu Ser Ala Gly Ala Ala Ser
        195                 200                 205

Val Xaa Xaa His Xaa Leu Xaa Xaa Xaa Ser Xaa Xaa Leu Phe Xaa Arg
    210                 215                 220

Ala Xaa Leu Xaa Ser Gly Xaa Xaa Asn Xaa Pro Trp Ala Xaa Xaa Xaa
225                 230                 235                 240

Xaa Xaa Glu Ala Arg Xaa Arg Xaa Xaa Xaa Leu Ala Xaa Xaa Xaa Gly
                245                 250                 255

Cys Xaa Xaa Xaa Xaa Xaa Xaa Asn Xaa Glu Xaa Xaa Xaa Cys
            260                 265                 270

Leu Arg Xaa Xaa Xaa Gln Xaa Xaa Xaa Xaa Glu Xaa Xaa Val
        275                 280                 285

Xaa Pro Xaa Xaa Xaa Xaa Xaa Xaa Phe Xaa Pro Xaa Val Asp
    290                 295                 300

Gly Asp Phe Leu Xaa Asp Xaa Pro Xaa Xaa Leu Xaa Xaa Xaa Gly Xaa
305                 310                 315                 320

Xaa Xaa Xaa Xaa Gln Xaa Leu Val Gly Val Xaa Lys Asp Glu Gly Xaa
                325                 330                 335

Xaa Phe Leu Val Tyr Gly Xaa Pro Gly Phe Ser Lys Asp Asn Xaa Ser
            340                 345                 350

Xaa Ile Xaa Arg Xaa Xaa Phe Xaa Xaa Gly Xaa Xaa Xaa Xaa Xaa Pro
        355                 360                 365

Xaa Xaa Ser Xaa Xaa Xaa Xaa Glu Xaa Xaa Xaa Xaa Xaa Tyr Xaa Asp
        370                 375                 380

Trp Xaa Xaa Xaa Xaa Xaa Xaa Xaa Arg Xaa Ala Xaa Xaa Xaa
385                 390                 395                 400

Val Xaa Gly Asp Xaa Asn Xaa Xaa Cys Pro Xaa Xaa Xaa Xaa Xaa
        405                 410                 415

Xaa Xaa Xaa Xaa Xaa Xaa Xaa Xaa Xaa Xaa Tyr Xaa Phe Glu His
        420                 425                 430

Arg Xaa Ser Xaa Leu Xaa Trp Pro Xaa Trp Met Gly Val Xaa His Gly
        435                 440                 445

Tyr Glu Ile Glu Phe Xaa Phe Gly Xaa Pro Leu Xaa Xaa Xaa Xaa Asn
        450                 455                 460

Tyr Thr Xaa Xaa Glu Xaa Xaa Xaa Xaa Xaa Xaa Xaa Xaa Xaa Xaa Trp
465                 470                 475                 480

Xaa Asn Phe Ala Xaa Xaa Gly Xaa Pro Asn Xaa Xaa Xaa Xaa Xaa
        485                 490                 495

Xaa Xaa Xaa Trp Pro Xaa Xaa Xaa Xaa Gln Xaa Tyr Xaa Xaa
        500                 505                 510

Leu Xaa Xaa Xaa Xaa Xaa Xaa Xaa Xaa Leu Arg Ala Xaa Xaa
        515                 520                 525

Cys Xaa Phe Trp Xaa Xaa Phe Xaa Pro Lys Xaa Leu Xaa Xaa Thr Xaa
        530                 535                 540

Xaa Xaa Asp Glu Xaa Glu Xaa Xaa Trp Lys Ala Xaa Phe His Arg Trp
545                 550                 555                 560

Xaa Xaa Tyr Met Xaa Xaa Trp Xaa Asn Gln Phe Xaa Asp Xaa Xaa Ser
            565                 570                 575

Lys Xaa Xaa Xaa Cys Xaa Xaa Leu
            580
```

```
<210> SEQ ID NO 11
<211> LENGTH: 551
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (57)..(61)
<223> OTHER INFORMATION: Xaa can be any naturally occurring amino acid
<220> FEATURE:
<221> NAME/KEY: misc_feature
<222> LOCATION: (64)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (75)..(77)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (83)..(83)
```

```
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (109)..(111)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(116)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (124)..(125)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (139)..(141)
<223> OTHER INFORMATION: Xaa can be any naturally occurring amino acid
<220> FEATURE:
<221> NAME/KEY: misc_feature
<222> LOCATION: (143)..(146)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(166)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
```

```
<222> LOCATION: (177)..(177)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (210)..(211)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (215)..(217)
<223> OTHER INFORMATION: Xaa can be any naturally occurring amino acid
<220> FEATURE:
<221> NAME/KEY: misc_feature
<222> LOCATION: (219)..(220)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (238)..(242)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (248)..(250)
<223> OTHER INFORMATION: Xaa can be any naturally occurring amino acid
<220> FEATURE:
<221> NAME/KEY: misc_feature
<222> LOCATION: (253)..(255)
<223> OTHER INFORMATION: Xaa can be any naturally occurring amino acid
<220> FEATURE:
```

```
<221> NAME/KEY: misc_feature
<222> LOCATION: (258)..(264)
<223> OTHER INFORMATION: Xaa can be any naturally occurring amino acid
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (269)..(271)
<223> OTHER INFORMATION: Xaa can be any naturally occurring amino acid
<220> FEATURE:
<221> NAME/KEY: misc_feature
<222> LOCATION: (275)..(278)
<223> OTHER INFORMATION: Xaa can be any naturally occurring amino acid
<220> FEATURE:
<221> NAME/KEY: misc_feature
<222> LOCATION: (280)..(284)
<223> OTHER INFORMATION: Xaa can be any naturally occurring amino acid
<220> FEATURE:
<221> NAME/KEY: misc_feature
<222> LOCATION: (286)..(287)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (291)..(298)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (309)..(309)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (313)..(314)
<223> OTHER INFORMATION: Xaa can be any naturally occurring amino acid
<220> FEATURE:
<221> NAME/KEY: misc_feature
<222> LOCATION: (316)..(318)
<223> OTHER INFORMATION: Xaa can be any naturally occurring amino acid
<220> FEATURE:
<221> NAME/KEY: misc_feature
<222> LOCATION: (320)..(324)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (336)..(337)
<223> OTHER INFORMATION: Xaa can be any naturally occurring amino acid
<220> FEATURE:
<221> NAME/KEY: misc_feature
<222> LOCATION: (343)..(343)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
```

```
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid
<220> FEATURE:
<221> NAME/KEY: misc_feature
<222> LOCATION: (357)..(358)
<223> OTHER INFORMATION: Xaa can be any naturally occurring amino acid
<220> FEATURE:
<221> NAME/KEY: misc_feature
<222> LOCATION: (360)..(361)
<223> OTHER INFORMATION: Xaa can be any naturally occurring amino acid
<220> FEATURE:
<221> NAME/KEY: misc_feature
<222> LOCATION: (363)..(367)
<223> OTHER INFORMATION: Xaa can be any naturally occurring amino acid
<220> FEATURE:
<221> NAME/KEY: misc_feature
<222> LOCATION: (369)..(370)
<223> OTHER INFORMATION: Xaa can be any naturally occurring amino acid
<220> FEATURE:
<221> NAME/KEY: misc_feature
<222> LOCATION: (372)..(375)
<223> OTHER INFORMATION: Xaa can be any naturally occurring amino acid
<220> FEATURE:
<221> NAME/KEY: misc_feature
<222> LOCATION: (377)..(381)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (386)..(394)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(400)
<223> OTHER INFORMATION: Xaa can be any naturally occurring amino acid
<220> FEATURE:
<221> NAME/KEY: misc_feature
<222> LOCATION: (402)..(402)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (407)..(408)
<223> OTHER INFORMATION: Xaa can be any naturally occurring amino acid
<220> FEATURE:
<221> NAME/KEY: misc_feature
<222> LOCATION: (411)..(427)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (436)..(436)
<223> OTHER INFORMATION: Xaa can be any naturally occurring amino acid
<220> FEATURE:
<221> NAME/KEY: misc_feature
<222> LOCATION: (438)..(438)
```

```
<223> OTHER INFORMATION: Xaa can be any naturally occurring amino acid
<220> FEATURE:
<221> NAME/KEY: misc_feature
<222> LOCATION: (441)..(441)
<223> OTHER INFORMATION: Xaa can be any naturally occurring amino acid
<220> FEATURE:
<221> NAME/KEY: misc_feature
<222> LOCATION: (446)..(446)
<223> OTHER INFORMATION: Xaa can be any naturally occurring amino acid
<220> FEATURE:
<221> NAME/KEY: misc_feature
<222> LOCATION: (454)..(454)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (460)..(463)
<223> OTHER INFORMATION: Xaa can be any naturally occurring amino acid
<220> FEATURE:
<221> NAME/KEY: misc_feature
<222> LOCATION: (467)..(468)
<223> OTHER INFORMATION: Xaa can be any naturally occurring amino acid
<220> FEATURE:
<221> NAME/KEY: misc_feature
<222> LOCATION: (470)..(479)
<223> OTHER INFORMATION: Xaa can be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (485)..(486)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (491)..(499)
<223> OTHER INFORMATION: Xaa can be any naturally occurring amino acid
<220> FEATURE:
<221> NAME/KEY: misc_feature
<222> LOCATION: (502)..(507)
<223> OTHER INFORMATION: Xaa can be any naturally occurring amino acid
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (511)..(512)
<223> OTHER INFORMATION: Xaa can be any naturally occurring amino acid
<220> FEATURE:
<221> NAME/KEY: misc_feature
<222> LOCATION: (514)..(523)
<223> OTHER INFORMATION: Xaa can be any naturally occurring amino acid
<220> FEATURE:
<221> NAME/KEY: misc_feature
<222> LOCATION: (527)..(528)
<223> OTHER INFORMATION: Xaa can be any naturally occurring amino acid
<220> FEATURE:
<221> NAME/KEY: misc_feature
<222> LOCATION: (530)..(530)
<223> OTHER INFORMATION: Xaa can be any naturally occurring amino acid
<220> FEATURE:
<221> NAME/KEY: misc_feature
<222> LOCATION: (533)..(534)
<223> OTHER INFORMATION: Xaa can be any naturally occurring amino acid
<220> FEATURE:
<221> NAME/KEY: misc_feature
<222> LOCATION: (536)..(536)
<223> OTHER INFORMATION: Xaa can be any naturally occurring amino acid
<220> FEATURE:
<221> NAME/KEY: misc_feature
```

```
<222> LOCATION: (539)..(539)
<223> OTHER INFORMATION: Xaa can be any naturally occurring amino acid
<220> FEATURE:
<221> NAME/KEY: misc_feature
<222> LOCATION: (541)..(542)
<223> OTHER INFORMATION: Xaa can be any naturally occurring amino acid
<220> FEATURE:
<221> NAME/KEY: misc_feature
<222> LOCATION: (544)..(546)
<223> OTHER INFORMATION: Xaa can be any naturally occurring amino acid
<220> FEATURE:
<221> NAME/KEY: misc_feature
<222> LOCATION: (549)..(549)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid

<400> SEQUENCE: 11

Glu Xaa Xaa Xaa Xaa Xaa Xaa Xaa Xaa Xaa Xaa Xaa Gly Xaa
1               5                   10                  15

Xaa Arg Gly Xaa Xaa Xaa Xaa Xaa Xaa Gly Xaa Val Xaa Ala Phe
            20                  25                  30

Leu Gly Ile Pro Xaa Ala Xaa Pro Pro Xaa Gly Xaa Xaa Arg Phe Xaa
            35                  40                  45

Xaa Pro Xaa Xaa Xaa Xaa Xaa Trp Xaa Xaa Xaa Xaa Xaa Ala Thr Xaa
        50                  55                  60

Xaa Xaa Xaa Xaa Cys Xaa Gln Xaa Xaa Asp Xaa Xaa Xaa Pro Gly Phe
65                  70                  75                  80

Xaa Gly Xaa Glu Met Trp Asn Pro Asn Xaa Xaa Leu Ser Glu Asp Cys
            85                  90                  95

Leu Tyr Leu Asn Val Trp Xaa Pro Xaa Pro Xaa Xaa Xaa Thr
            100                 105                 110

Xaa Val Xaa Xaa Trp Ile Tyr Gly Gly Xaa Phe Xaa Xaa Gly Xaa Xaa
        115                 120                 125

Ser Leu Xaa Val Tyr Asp Gly Xaa Phe Leu Xaa Xaa Xaa Glu Xaa Xaa
        130                 135                 140

Xaa Xaa Val Ser Met Asn Tyr Arg Val Gly Xaa Xaa Gly Phe Leu Ala
145                 150                 155                 160

Xaa Pro Gly Xaa Xaa Xaa Ala Pro Gly Asn Xaa Gly Leu Xaa Asp Gln
            165                 170                 175

Xaa Leu Ala Leu Gln Trp Val Gln Xaa Asn Xaa Ala Ala Phe Gly Gly
        180                 185                 190

Xaa Pro Xaa Ser Xaa Thr Xaa Phe Gly Glu Ser Ala Gly Ala Ala Ser
        195                 200                 205

Val Xaa Xaa His Xaa Leu Xaa Xaa Xaa Ser Xaa Xaa Leu Phe Xaa Arg
210                 215                 220

Ala Xaa Leu Xaa Ser Gly Xaa Xaa Asn Xaa Pro Trp Ala Xaa Xaa Xaa
225                 230                 235                 240

Xaa Xaa Glu Ala Arg Xaa Arg Xaa Xaa Xaa Leu Ala Xaa Xaa Xaa Gly
            245                 250                 255

Cys Xaa Xaa Xaa Xaa Xaa Xaa Asn Xaa Xaa Glu Xaa Xaa Xaa Cys
        260                 265                 270

Leu Arg Xaa Xaa Xaa Gln Xaa Xaa Xaa Xaa Glu Xaa Xaa Val
        275                 280                 285

Xaa Pro Xaa Xaa Xaa Xaa Xaa Xaa Phe Xaa Pro Xaa Val Asp
290                 295                 300

Gly Asp Phe Leu Xaa Asp Xaa Pro Xaa Xaa Leu Xaa Xaa Xaa Gly Xaa
```

```
            305                 310                 315                 320
Xaa Xaa Xaa Xaa Gln Xaa Leu Val Gly Val Xaa Lys Asp Glu Gly Xaa
                325                 330                 335

Xaa Phe Leu Val Tyr Gly Xaa Pro Gly Phe Ser Lys Asp Asn Xaa Ser
                340                 345                 350

Xaa Ile Xaa Arg Xaa Xaa Phe Xaa Gly Xaa Xaa Xaa Xaa Xaa Xaa Pro
                355                 360                 365

Xaa Xaa Ser Xaa Xaa Xaa Xaa Glu Xaa Xaa Xaa Xaa Xaa Tyr Xaa Asp
                370                 375                 380

Trp Xaa Xaa Xaa Xaa Xaa Xaa Xaa Arg Xaa Ala Xaa Xaa Xaa
385                 390                 395                 400

Val Xaa Gly Asp Xaa Asn Xaa Xaa Cys Pro Xaa Xaa Xaa Xaa Xaa
                405                 410                 415

Xaa Xaa Xaa Xaa Xaa Xaa Xaa Xaa Xaa Xaa Tyr Xaa Phe Glu His
                420                 425                 430

Arg Xaa Ser Xaa Leu Xaa Trp Pro Xaa Trp Met Gly Val Xaa His Gly
                435                 440                 445

Tyr Glu Ile Glu Phe Xaa Phe Gly Xaa Pro Leu Xaa Xaa Xaa Xaa Asn
450                 455                 460

Tyr Thr Xaa Xaa Glu Xaa Xaa Xaa Xaa Xaa Xaa Xaa Xaa Xaa Xaa Trp
465                 470                 475                 480

Xaa Asn Phe Ala Xaa Xaa Gly Xaa Pro Asn Xaa Xaa Xaa Xaa Xaa Xaa
                485                 490                 495

Xaa Xaa Xaa Trp Pro Xaa Xaa Xaa Xaa Xaa Gln Xaa Tyr Xaa Xaa
                500                 505                 510

Leu Xaa Xaa Xaa Xaa Xaa Xaa Xaa Xaa Xaa Leu Arg Ala Xaa Xaa
                515                 520                 525

Cys Xaa Phe Trp Xaa Xaa Phe Xaa Pro Lys Xaa Leu Xaa Xaa Thr Xaa
                530                 535                 540

Xaa Xaa Asp Glu Xaa Glu Xaa
545                 550

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16
```

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 445
<212> TYPE: PRT
<213> ORGANISM: Artificial Sequence
<220> FEATURE:
<223> OTHER INFORMATION: Synthetic construct

<400> SEQUENCE: 20

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Asp Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Phe Cys
                85                  90                  95

Ala Arg Pro Leu Tyr Gly Ser Ser Pro Gly Trp Phe Ala Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240
```

-continued

```
Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 21
<211> LENGTH: 445
<212> TYPE: PRT
<213> ORGANISM: Artificial Sequence
<220> FEATURE:
<223> OTHER INFORMATION: Synthetic construct

<400> SEQUENCE: 21

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Asp Thr Ile Tyr Tyr Ala Asp Thr Val
50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Leu Tyr Gly Ser Ser Pro Gly Trp Phe Ala Tyr Trp Gly
            100                 105                 110

Gln Gly Thr Leu Val Thr Val Thr Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160
```

-continued

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Val Thr Val Pro
            180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
        290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
        370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 22
<211> LENGTH: 443
<212> TYPE: PRT
<213> ORGANISM: Artificial Sequence
<220> FEATURE:
<223> OTHER INFORMATION: Synthetic construct

<400> SEQUENCE: 22

Glu Val Gln Leu Gln Gln Ser Gly Pro Glu Leu Val Lys Thr Gly Ala
1               5                   10                  15

Ser Val Lys Ile Ser Cys Lys Ala Ser Tyr Ser Ser Phe Thr Ser Tyr
            20                  25                  30

Tyr Ile His Trp Val Lys Gln Ser His Gly Lys Ser Leu Glu Trp Ile
        35                  40                  45

Gly Tyr Ile Ser Cys Tyr Asn Gly Ala Thr Thr Tyr Asn Gln Lys Phe
    50                  55                  60

Lys Gly Lys Ala Thr Phe Thr Val Asp Thr Ser Ser Asn Thr Ala Tyr
65                  70                  75                  80

```
Met Gln Phe Asn Ser Leu Thr Ser Glu Asp Ser Ala Val Tyr Tyr Cys
                 85                  90                  95
Ala Arg Trp Phe Gly Ser Thr Gly Ala Met Asp Tyr Trp Gly Gln Gly
            100                 105                 110
Thr Ser Val Thr Val Ser Ser Ala Lys Thr Thr Pro Pro Ser Val Tyr
        115                 120                 125
Pro Leu Ala Pro Gly Ser Ala Ala Gln Thr Asn Ser Met Val Thr Leu
    130                 135                 140
Gly Cys Leu Val Lys Gly Tyr Phe Pro Glu Pro Val Thr Val Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Ser Val Thr Val Pro Ser Ser
            180                 185                 190
Thr Trp Pro Ser Glu Thr Val Thr Cys Asn Val Ala His Pro Ala Ser
        195                 200                 205
Ser Thr Lys Val Asp Lys Lys Ile Val Pro Arg Asp Cys Gly Cys Lys
    210                 215                 220
Pro Cys Ile Cys Thr Val Pro Glu Val Ser Ser Val Phe Ile Phe Pro
225                 230                 235                 240
Pro Lys Pro Lys Asp Val Leu Thr Ile Thr Leu Thr Pro Lys Val Thr
                245                 250                 255
Cys Val Val Val Asp Ile Ser Lys Asp Asp Pro Glu Val Gln Phe Ser
            260                 265                 270
Trp Phe Val Asp Asp Val Glu Val His Thr Ala Gln Thr Gln Pro Arg
        275                 280                 285
Glu Glu Gln Phe Asn Ser Thr Phe Arg Ser Val Ser Glu Leu Pro Ile
    290                 295                 300
Met His Gln Asp Trp Leu Asn Gly Lys Glu Phe Lys Cys Arg Val Asn
305                 310                 315                 320
Ser Ala Ala Phe Pro Ala Pro Ile Glu Lys Thr Ile Ser Lys Thr Lys
                325                 330                 335
Gly Arg Pro Lys Ala Pro Gln Val Tyr Thr Ile Pro Pro Pro Lys Glu
            340                 345                 350
Gln Met Ala Lys Asp Lys Val Ser Leu Thr Cys Met Ile Thr Asp Phe
        355                 360                 365
Phe Pro Glu Asp Ile Thr Val Glu Trp Gln Trp Asn Gly Gln Pro Ala
    370                 375                 380
Glu Asn Tyr Lys Asn Thr Gln Pro Ile Met Asp Thr Asp Gly Ser Tyr
385                 390                 395                 400
Phe Val Tyr Ser Lys Leu Asn Val Gln Lys Ser Asn Trp Glu Ala Gly
                405                 410                 415
Asn Thr Phe Thr Cys Ser Val Leu His Glu Gly Leu His Asn His His
            420                 425                 430
Thr Glu Lys Ser Leu Ser His Ser Pro Gly Lys
        435                 440
```

<210> SEQ ID NO 23
<211> LENGTH: 444
<212> TYPE: PRT
<213> ORGANISM: Artificial Sequence
<220> FEATURE:
<223> OTHER INFORMATION: Synthetic construct

<400> SEQUENCE: 23

-continued

```
Glu Val Gln Leu Gln Gln Ser Gly Pro Glu Val Val Lys Thr Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Ser His Gly Lys Ser Leu Glu Trp Ile
            35                  40                  45

Gly Tyr Ile Ser Cys Tyr Asn Gly Ala Ala Ser Tyr Asn Gln Arg Phe
        50                  55                  60

Lys Gly Lys Ala Thr Phe Thr Val Asp Thr Ser Ser Thr Ala Tyr
65                  70                  75                  80

Met Gln Phe Asn Ser Leu Thr Ser Glu Asp Ser Ala Val Tyr Tyr Cys
                85                  90                  95

Ala Arg Phe Glu Ser Met Thr Thr Gly Ala Met Asp Tyr Trp Gly Gln
            100                 105                 110

Gly Thr Ser Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
            275                 280                 285

Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
        370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
```

His Thr Glu Lys Ser Leu Ser His Ser Pro Gly Lys
                435                 440

<210> SEQ ID NO 24
<211> LENGTH: 439
<212> TYPE: PRT
<213> ORGANISM: Artificial Sequence
<220> FEATURE:
<223> OTHER INFORMATION: Synthetic construct

<400> SEQUENCE: 24

Asp Val Lys Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Phe
            20                  25                  30

Thr Met Ser Trp Val Arg Gln Thr Pro Glu Lys Arg Leu Glu Trp Val
        35                  40                  45

Ala Thr Ile Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Gly Met Tyr Tyr Cys
                85                  90                  95

Thr Arg Asp Ala His Phe Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
    210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
    290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys

```
                340                 345                 350
Asp Lys Val Ser Leu Thr Cys Met Ile Thr Asp Phe Phe Pro Glu Asp
        355                 360                 365

Ile Thr Val Glu Trp Gln Trp Asn Gly Gln Pro Ala Glu Asn Tyr Lys
    370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
        435

<210> SEQ ID NO 25
<211> LENGTH: 442
<212> TYPE: PRT
<213> ORGANISM: Artificial Sequence
<220> FEATURE:
<223> OTHER INFORMATION: Synthetic construct

<400> SEQUENCE: 25

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Ser Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Tyr Gly Lys Asp His Phe Asp Tyr Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Pro
            180                 185                 190

Arg Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
```

```
                260                 265                 270
Phe Val Asp Asp Val Glu Val His Thr Ala Gln Thr Gln Pro Arg Glu
            275                 280                 285
Glu Gln Phe Asn Ser Thr Phe Arg Ser Val Ser Glu Leu Pro Ile Met
        290                 295                 300
His Gln Asp Trp Leu Asn Gly Lys Glu Phe Lys Cys Arg Val Asn Ser
305                 310                 315                 320
Ala Ala Phe Pro Ala Pro Ile Glu Lys Thr Ile Ser Lys Thr Lys Gly
                325                 330                 335
Arg Pro Lys Ala Pro Gln Val Tyr Thr Ile Pro Pro Lys Glu Gln
            340                 345                 350
Met Ala Lys Asp Lys Val Ser Leu Thr Cys Met Ile Thr Asp Phe Phe
            355                 360                 365
Pro Glu Asp Ile Thr Val Glu Trp Gln Trp Asn Gly Gln Pro Ala Glu
        370                 375                 380
Asn Tyr Lys Asn Thr Gln Pro Ile Met Asn Thr Asn Gly Ser Tyr Phe
385                 390                 395                 400
Val Tyr Ser Lys Leu Asn Val Gln Lys Ser Asn Trp Glu Ala Gly Asn
                405                 410                 415
Thr Phe Thr Cys Ser Val Leu His Glu Gly Leu His Asn His His Thr
            420                 425                 430
Glu Lys Ser Leu Ser His Ser Pro Gly Lys
            435                 440

<210> SEQ ID NO 26
<211> LENGTH: 444
<212> TYPE: PRT
<213> ORGANISM: Artificial Sequence
<220> FEATURE:
<223> OTHER INFORMATION: Synthetic construct

<400> SEQUENCE: 26

Gln Val Gln Leu Gln Gln Ser Gly Ala Glu Leu Val Arg Pro Gly Ser
1               5                   10                  15
Ser Val Lys Ile Ser Cys Lys Ala Ser Gly Tyr Ala Phe Ser Asp Tyr
            20                  25                  30
Trp Met Asn Trp Val Lys Gln Arg Pro Gly Gln Gly Leu Glu Trp Ile
        35                  40                  45
Gly Gln Ile Tyr Pro Gly Asp Gly Asp Thr Tyr Tyr Asn Gly Lys Phe
    50                  55                  60
Lys Gly Lys Ala Thr Leu Thr Ala Asp Lys Ser Ser Ser Thr Ala Tyr
65                  70                  75                  80
Met Gln Leu Ser Ser Leu Ile Ser Glu Asp Ser Ala Val Tyr Phe Cys
                85                  90                  95
Ala Arg Ser Arg Pro Leu Leu Asp Tyr Ser Met His Tyr Trp Gly Gln
            100                 105                 110
Gly Ala Ser Val Thr Val Ser Ser Ala Lys Thr Thr Pro Pro Ser Val
        115                 120                 125
Tyr Pro Leu Ala Pro Gly Ser Ala Ala Gln Thr Asn Ser Met Val Thr
    130                 135                 140
Leu Gly Cys Leu Val Lys Gly Tyr Phe Pro Glu Pro Val Thr Val Thr
145                 150                 155                 160
Trp Asn Ser Gly Ser Leu Ser Ser Gly Val His Thr Phe Pro Ala Val
                165                 170                 175
Leu Gln Ser Asp Leu Tyr Thr Leu Ser Ser Ser Val Thr Val Pro Ser
```

```
                180             185             190
Ser Pro Arg Pro Ser Glu Thr Val Thr Cys Asn Val Ala His Pro Ala
            195             200             205

Ser Ser Thr Lys Val Asp Lys Lys Ile Val Pro Arg Asp Cys Gly Cys
        210             215             220

Lys Pro Cys Ile Cys Thr Val Pro Glu Val Ser Ser Val Phe Ile Phe
225             230             235             240

Pro Pro Lys Pro Lys Asp Val Leu Thr Ile Thr Leu Thr Pro Lys Val
            245             250             255

Thr Cys Val Val Val Asp Ile Ser Lys Asp Asp Pro Glu Val Gln Phe
        260             265             270

Ser Trp Phe Val Asp Asp Val Glu Val His Thr Ala Gln Thr Gln Pro
    275             280             285

Arg Glu Glu Gln Phe Asn Ser Thr Phe Arg Ser Val Ser Glu Leu Pro
        290             295             300

Ile Met His Gln Asp Trp Leu Asn Gly Lys Glu Phe Lys Cys Arg Val
305             310             315             320

Asn Ser Ala Ala Phe Pro Ala Pro Ile Glu Lys Thr Ile Ser Lys Thr
            325             330             335

Lys Gly Arg Pro Lys Ala Pro Gln Val Tyr Thr Ile Pro Pro Pro Lys
        340             345             350

Glu Gln Met Ala Lys Asp Lys Val Ser Leu Thr Cys Met Ile Thr Asp
    355             360             365

Phe Phe Pro Glu Asp Ile Thr Val Glu Trp Gln Trp Asn Gly Gln Pro
370             375             380

Ala Glu Asn Tyr Lys Asn Thr Gln Pro Ile Met Asn Thr Asn Gly Ser
385             390             395             400

Tyr Phe Val Tyr Ser Lys Leu Asn Val Gln Lys Ser Asn Trp Glu Ala
            405             410             415

Gly Asn Thr Phe Thr Cys Ser Val Leu His Glu Gly Leu His Asn His
        420             425             430

His Thr Glu Lys Ser Leu Ser His Ser Pro Gly Lys
    435             440
```

<210> SEQ ID NO 27
<211> LENGTH: 443
<212> TYPE: PRT
<213> ORGANISM: Artificial Sequence
<220> FEATURE:
<223> OTHER INFORMATION: Synthetic construct

<400> SEQUENCE: 27

```
Glu Val Gln Leu Gln Gln Ser Gly Pro Glu Leu Val Lys Pro Gly Ala
1               5               10              15

Ser Val Lys Ile Ser Cys Lys Ala Ser Gly Tyr Thr Phe Thr Asp Tyr
            20              25              30

Ser Met His Trp Val Lys Leu Ser His Gly Lys Ser Leu Glu Trp Ile
        35              40              45

Gly Tyr Ile Tyr Pro Tyr Asn Asp Asp Thr Asp Tyr Asn Gln Lys Phe
    50              55              60

Lys Thr Lys Ala Thr Leu Thr Val Asp Ser Ser Ser Ile Thr Tyr
65              70              75              80

Leu Glu Leu Arg Ser Leu Thr Ser Glu Asp Ser Ala Val Tyr Tyr Cys
            85              90              95

Ala Arg Ser Asp Gly Tyr Ser Tyr Tyr Phe Asp Tyr Trp Gly Gln Gly
```

```
            100                 105                 110
Thr Thr Leu Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
        180                 185                 190

Pro Arg Pro Ser Glu Thr Val Thr Cys Asn Val Ala His Pro Ala Ser
    195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asn Thr Asn Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
        435                 440

<210> SEQ ID NO 28
<211> LENGTH: 457
<212> TYPE: PRT
<213> ORGANISM: Artificial Sequence
<220> FEATURE:
<223> OTHER INFORMATION: Synthetic construct

<400> SEQUENCE: 28

Met Glu Cys Asn Trp Ile Leu Pro Phe Ile Leu Ser Val Thr Ser Gly
1               5                   10                  15

Val Tyr Ser Gln Val Gln Leu Gln Gln Ser Gly Ala Glu Leu Ala Arg
```

-continued

```
                20                  25                  30
Pro Gly Ala Ser Val Lys Leu Ser Cys Lys Ala Ser Gly Tyr Thr Phe
            35                  40                  45
Thr Ser Gln Trp Leu Gln Trp Val Lys Gln Arg Pro Gly Gln Gly Leu
            50                  55                  60
Glu Trp Ile Gly Ala Ile Tyr Pro Gly Asp Gly Asp Thr Arg Tyr Thr
65                  70                  75                  80
Gln Lys Phe Lys Gly Lys Ala Thr Leu Thr Ala Asp Lys Ser Ser Ser
                    85                  90                  95
Thr Ala Tyr Met Gln Leu Thr Asn Leu Ala Pro Glu Asp Ser Ala Val
                100                 105                 110
Tyr Tyr Cys Ala Arg Ser Ser Met Asp Tyr Trp Gly Gln Gly Thr Ser
                115                 120                 125
Val Thr Val Ser Ser Ala Lys Thr Thr Pro Pro Ser Val Tyr Pro Leu
            130                 135                 140
Ala Pro Gly Ser Ala Ala Gln Thr Asn Ser Met Val Thr Leu Gly Cys
145                 150                 155                 160
Leu Val Lys Gly Tyr Phe Pro Glu Pro Val Thr Val Thr Trp Asn Ser
                165                 170                 175
Gly Ser Leu Ser Ser Gly Val His Thr Phe Pro Ala Val Leu Gln Ser
            180                 185                 190
Asp Leu Tyr Thr Leu Ser Ser Ser Val Thr Val Pro Ser Ser Thr Trp
            195                 200                 205
Pro Ser Glu Thr Val Thr Cys Asn Val Ala His Pro Ala Ser Ser Thr
            210                 215                 220
Lys Val Asp Lys Lys Ile Val Pro Arg Asp Cys Gly Cys Lys Pro Cys
225                 230                 235                 240
Ile Cys Thr Val Pro Glu Val Ser Val Phe Ile Phe Pro Pro Lys
                245                 250                 255
Pro Lys Asp Val Leu Thr Ile Thr Leu Thr Pro Lys Val Thr Cys Val
            260                 265                 270
Val Val Asp Ile Ser Lys Asp Asp Pro Glu Val Gln Phe Ser Trp Phe
            275                 280                 285
Val Asp Asp Val Glu Val His Thr Ala Gln Thr Gln Pro Arg Glu Glu
            290                 295                 300
Gln Phe Asn Ser Thr Phe Arg Ser Val Ser Glu Leu Pro Ile Met His
305                 310                 315                 320
Gln Asp Trp Leu Asn Gly Lys Glu Phe Lys Cys Arg Val Asn Ser Ala
                325                 330                 335
Ala Phe Pro Ala Pro Ile Glu Lys Thr Ile Ser Lys Thr Lys Gly Arg
                340                 345                 350
Pro Lys Ala Pro Gln Val Tyr Thr Ile Pro Pro Pro Lys Glu Gln Met
            355                 360                 365
Ala Lys Asp Lys Val Ser Leu Thr Cys Met Ile Thr Asp Phe Phe Pro
            370                 375                 380
Glu Asp Ile Thr Val Glu Trp Gln Trp Asn Gly Gln Pro Ala Glu Asn
385                 390                 395                 400
Tyr Lys Asn Thr Gln Pro Ile Met Asp Thr Asp Gly Ser Tyr Phe Val
                405                 410                 415
Tyr Ser Lys Leu Asn Val Gln Lys Ser Asn Trp Glu Ala Gly Asn Thr
            420                 425                 430
Phe Thr Cys Ser Val Leu His Glu Gly Leu His Asn His His Thr Glu
            435                 440                 445
```

Lys Ser Leu Ser His Ser Pro Gly Lys
    450                 455

<210> SEQ ID NO 29
<211> LENGTH: 121
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (9)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (38)..(44)
<223> OTHER INFORMATION: Xaa can be any naturally occurring amino acid
<220> FEATURE:
<221> NAME/KEY: misc_feature
<222> LOCATION: (48)..(50)
<223> OTHER INFORMATION: Xaa can be any naturally occurring amino acid
<220> FEATURE:
<221> NAME/KEY: misc_feature
<222> LOCATION: (52)..(59)
<223> OTHER INFORMATION: Xaa can be any naturally occurring amino acid
<220> FEATURE:
<221> NAME/KEY: misc_feature
<222> LOCATION: (61)..(64)
<223> OTHER INFORMATION: Xaa can be any naturally occurring amino acid
<220> FEATURE:
<221> NAME/KEY: misc_feature
<222> LOCATION: (66)..(68)
<223> OTHER INFORMATION: Xaa can be any naturally occurring amino acid
<220> FEATURE:
<221> NAME/KEY: misc_feature
<222> LOCATION: (70)..(72)
<223> OTHER INFORMATION: Xaa can be any naturally occurring amino acid
<220> FEATURE:
<221> NAME/KEY: misc_feature
<222> LOCATION: (74)..(85)
<223> OTHER INFORMATION: Xaa can be any naturally occurring amino acid
<220> FEATURE:
<221> NAME/KEY: misc_feature
<222> LOCATION: (87)..(88)
<223> OTHER INFORMATION: Xaa can be any naturally occurring amino acid

```
<220> FEATURE:
<221> NAME/KEY: misc_feature
<222> LOCATION: (91)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(109)
<223> OTHER INFORMATION: Xaa can be any naturally occurring amino acid
<220> FEATURE:
<221> NAME/KEY: misc_feature
<222> LOCATION: (115)..(117)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid

<400> SEQUENCE: 29

Xaa Val Xaa Xaa Xaa Ser Gly Xaa Xaa Xaa Xaa Xaa Xaa Gly Xaa
1               5                   10                  15

Ser Xaa Lys Xaa Ser Cys Xaa Ala Ser Xaa Xaa Xaa Phe Xaa Xaa Xaa
                20                  25                  30

Xaa Xaa Xaa Trp Val Xaa Xaa Xaa Xaa Xaa Xaa Xaa Leu Glu Trp Xaa
            35                  40                  45

Xaa Xaa Ile Xaa Xaa Xaa Xaa Xaa Xaa Xaa Tyr Xaa Xaa Xaa Xaa
50                  55                  60

Lys Xaa Xaa Xaa Thr Xaa Xaa Xaa Asp Xaa Xaa Xaa Xaa Xaa Xaa
65                  70                  75                  80

Xaa Xaa Xaa Xaa Xaa Leu Xaa Xaa Glu Asp Xaa Xaa Xaa Tyr Xaa Cys
                85                  90                  95

Xaa Arg Xaa Xaa Xaa Xaa Xaa Xaa Xaa Xaa Xaa Xaa Tyr Trp Gly
            100                 105                 110

Gln Gly Xaa Xaa Xaa Thr Val Xaa Xaa
        115                 120

<210> SEQ ID NO 30
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 30

Xaa Xaa Xaa Phe Xaa Xaa Xaa Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (2)..(8)
<223> OTHER INFORMATION: Xaa can be any naturally occurring amino acid

<400> SEQUENCE: 31

Ile Xaa Xaa Xaa Xaa Xaa Xaa Xaa
1               5

<210> SEQ ID NO 32
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(13)
<223> OTHER INFORMATION: Xaa can be any naturally occurring amino acid

<400> SEQUENCE: 32

Xaa Arg Xaa Xaa Xaa Xaa Xaa Xaa Xaa Xaa Xaa Xaa Xaa Tyr
1               5                   10

<210> SEQ ID NO 33
<211> LENGTH: 121
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
<220> FEATURE:
```

```
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (48)..(50)
<223> OTHER INFORMATION: Xaa can be any naturally occurring amino acid
<220> FEATURE:
<221> NAME/KEY: misc_feature
<222> LOCATION: (53)..(59)
<223> OTHER INFORMATION: Xaa can be any naturally occurring amino acid
<220> FEATURE:
<221> NAME/KEY: misc_feature
<222> LOCATION: (61)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(72)
<223> OTHER INFORMATION: Xaa can be any naturally occurring amino acid
<220> FEATURE:
<221> NAME/KEY: misc_feature
<222> LOCATION: (74)..(77)
<223> OTHER INFORMATION: Xaa can be any naturally occurring amino acid
<220> FEATURE:
<221> NAME/KEY: misc_feature
<222> LOCATION: (79)..(81)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (91)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(109)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid

<400> SEQUENCE: 33

Xaa Val Xaa Xaa Xaa Xaa Ser Gly Xaa Xaa Val Xaa Xaa Gly Xaa
1               5                   10                  15

Ser Xaa Lys Xaa Ser Cys Xaa Ala Ser Xaa Xaa Xaa Phe Xaa Xaa Xaa
            20                  25                  30
```

Xaa Xaa Xaa Trp Val Xaa Gln Xaa Xaa Xaa Lys Xaa Leu Glu Trp Xaa
         35                  40                  45

Xaa Xaa Ile Ser Xaa Xaa Xaa Xaa Xaa Xaa Tyr Xaa Xaa Xaa Xaa
     50                  55                  60

Lys Gly Xaa Xaa Thr Xaa Xaa Xaa Asp Xaa Xaa Xaa Thr Xaa Xaa
 65              70                  75                  80

Xaa Gln Xaa Xaa Ser Leu Xaa Ser Glu Asp Xaa Xaa Xaa Tyr Xaa Cys
             85                  90                  95

Xaa Arg Xaa Xaa Xaa Xaa Xaa Xaa Xaa Xaa Xaa Tyr Trp Gly
         100                 105                 110

Gln Gly Thr Xaa Xaa Thr Val Xaa Xaa
         115                 120

<210> SEQ ID NO 34
<211> LENGTH: 121
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (39)..(41)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (54)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:

```
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (87)..(88)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (99)..(109)
<223> OTHER INFORMATION: Xaa can be any naturally occurring amino acid
<220> FEATURE:
<221> NAME/KEY: misc_feature
<222> LOCATION: (115)..(117)
<223> OTHER INFORMATION: Xaa can be any naturally occurring amino acid

<400> SEQUENCE: 34

Xaa Val Gln Leu Gln Gln Ser Gly Xaa Glu Leu Xaa Xaa Pro Gly Xaa
1               5                   10                  15

Ser Val Lys Xaa Ser Cys Lys Ala Ser Gly Tyr Xaa Phe Xaa Xaa Xaa
            20                  25                  30

Xaa Xaa Xaa Trp Val Lys Xaa Xaa Xaa Gly Xaa Xaa Leu Glu Trp Ile
        35                  40                  45

Gly Xaa Ile Tyr Pro Xaa Xaa Xaa Asp Thr Xaa Tyr Xaa Xaa Lys Phe
    50                  55                  60

Lys Xaa Lys Ala Thr Leu Thr Xaa Asp Xaa Ser Ser Xaa Xaa Xaa Tyr
65                  70                  75                  80

Xaa Xaa Leu Xaa Xaa Leu Xaa Xaa Glu Asp Ser Ala Val Tyr Xaa Cys
                85                  90                  95

Ala Arg Xaa Xaa Xaa Xaa Xaa Xaa Xaa Xaa Xaa Xaa Xaa Tyr Trp Gly
            100                 105                 110

Gln Gly Xaa Xaa Xaa Thr Val Ser Ser
        115                 120

<210> SEQ ID NO 35
<211> LENGTH: 330
<212> TYPE: PRT
<213> ORGANISM: Artificial Sequence
<220> FEATURE:
<223> OTHER INFORMATION: Synthetic construct

<400> SEQUENCE: 35

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 324
<212> TYPE: PRT
<213> ORGANISM: Artificial Sequence
<220> FEATURE:
<223> OTHER INFORMATION: Synthetic construct

<400> SEQUENCE: 36

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45
```

Gly Val His Thr Phe Pro Ala Val Leu Gln Ser Asp Leu Tyr Thr Leu
50 55 60

Ser Ser Ser Val Thr Val Pro Ser Ser Arg Pro Ser Glu Thr Val
65 70 75 80

Thr Cys Asn Val Ala His Pro Ala Ser Ser Thr Lys Val Asp Lys Lys
85 90 95

Ile Val Pro Arg Asp Cys Gly Cys Lys Pro Cys Ile Cys Thr Val Pro
100 105 110

Glu Val Ser Ser Val Phe Ile Phe Pro Pro Lys Pro Lys Asp Val Leu
115 120 125

Thr Ile Thr Leu Thr Pro Lys Val Thr Cys Val Val Val Asp Ile Ser
130 135 140

Lys Asp Asp Pro Glu Val Gln Phe Ser Trp Phe Val Asp Asp Val Glu
145 150 155 160

Val His Thr Ala Gln Thr Gln Pro Arg Glu Glu Gln Phe Asn Ser Thr
165 170 175

Phe Arg Ser Val Ser Glu Leu Pro Ile Met His Gln Asp Trp Leu Asn
180 185 190

Gly Lys Glu Phe Lys Cys Arg Val Asn Ser Ala Ala Phe Pro Ala Pro
195 200 205

Ile Glu Lys Thr Ile Ser Lys Thr Lys Gly Arg Pro Lys Ala Pro Gln
210 215 220

Val Tyr Thr Ile Pro Pro Pro Lys Glu Gln Met Ala Lys Asp Lys Val
225 230 235 240

Ser Leu Thr Cys Met Ile Thr Asp Phe Phe Pro Glu Asp Ile Thr Val
245 250 255

Glu Trp Gln Trp Asn Gly Gln Pro Ala Glu Asn Tyr Lys Asn Thr Gln
260 265 270

Pro Ile Met Asp Thr Asp Gly Ser Tyr Phe Val Tyr Ser Lys Leu Asn
275 280 285

Val Gln Lys Ser Asn Trp Glu Ala Gly Asn Thr Phe Thr Cys Ser Val
290 295 300

Leu His Glu Gly Leu His Asn His His Thr Glu Lys Ser Leu Ser His
305 310 315 320

Ser Pro Gly Lys

<210> SEQ ID NO 37
<211> LENGTH: 324
<212> TYPE: PRT
<213> ORGANISM: Artificial Sequence
<220> FEATURE:
<223> OTHER INFORMATION: Synthetic construct

<400> SEQUENCE: 37

Ala Lys Thr Thr Pro Pro Ser Val Tyr Pro Leu Ala Pro Gly Ser Ala
1 5 10 15

Ala Gln Thr Asn Ser Met Val Thr Leu Gly Cys Leu Val Lys Gly Tyr
20 25 30

Phe Pro Glu Pro Val Thr Val Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Pro Ser Ser Thr Trp Pro Ser Glu Thr Val
65 70 75 80

Thr Cys Asn Val Ala His Pro Ala Ser Ser Thr Lys Val Asp Lys Lys

```
                    85                  90                  95
Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
                195                 200                 205

Ile Glu Lys Thr Ile Ser Lys Thr Lys Gly Arg Pro Lys Ala Pro Gln
            210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
                275                 280                 285

Val Gln Lys Ser Asn Trp Glu Ala Gly Asn Thr Phe Thr Cys Ser Val
            290                 295                 300

Leu His Glu Gly Leu His Asn His His Thr Glu Lys Ser Leu Ser His
305                 310                 315                 320

Ser Pro Gly Lys

<210> SEQ ID NO 38
<211> LENGTH: 332
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
```

```
<222> LOCATION: (40)..(40)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (75)..(79)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (101)..(102)
<223> OTHER INFORMATION: Xaa can be any naturally occurring amino acid
<220> FEATURE:
<221> NAME/KEY: misc_feature
<222> LOCATION: (104)..(108)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (113)..(116)
<223> OTHER INFORMATION: Xaa can be any naturally occurring amino acid
<220> FEATURE:
<221> NAME/KEY: misc_feature
<222> LOCATION: (119)..(123)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
```

```
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (153)..(154)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (192)..(194)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (209)..(211)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
```

-continued

```
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (229)..(230)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (239)..(244)
<223> OTHER INFORMATION: Xaa can be any naturally occurring amino acid
<220> FEATURE:
<221> NAME/KEY: misc_feature
<222> LOCATION: (246)..(247)
<223> OTHER INFORMATION: Xaa can be any naturally occurring amino acid
<220> FEATURE:
<221> NAME/KEY: misc_feature
<222> LOCATION: (253)..(256)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (267)..(268)
<223> OTHER INFORMATION: Xaa can be any naturally occurring amino acid
<220> FEATURE:
<221> NAME/KEY: misc_feature
<222> LOCATION: (273)..(274)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (282)..(283)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (298)..(298)
```

-continued

```
<223> OTHER INFORMATION: Xaa can be any naturally occurring amino acid
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (303)..(304)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (309)..(309)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid

<400> SEQUENCE: 38

Ala Xaa Thr Xaa Xaa Pro Ser Val Xaa Pro Leu Ala Pro Xaa Ser Xaa
1               5                   10                  15

Xaa Xaa Xaa Xaa Xaa Xaa Xaa Xaa Leu Gly Cys Leu Val Lys Xaa Tyr
            20                  25                  30

Phe Pro Glu Pro Val Thr Val Xaa Trp Asn Ser Gly Xaa Leu Xaa Ser
        35                  40                  45

Gly Val His Thr Phe Pro Ala Val Leu Gln Ser Xaa Xaa Leu Tyr Xaa
    50                  55                  60

Leu Ser Ser Xaa Val Thr Val Pro Ser Ser Xaa Xaa Xaa Xaa Xaa Thr
65                  70                  75                  80

Xaa Xaa Cys Asn Val Xaa His Xaa Xaa Ser Xaa Thr Lys Val Asp Lys
                85                  90                  95

Lys Xaa Xaa Pro Xaa Xaa Cys Xaa Xaa Xaa Xaa Xaa Cys Xaa Pro Cys
            100                 105                 110

Xaa Xaa Xaa Xaa Ala Pro Xaa Xaa Xaa Xaa Pro Ser Val Xaa Leu
        115                 120                 125

Phe Pro Pro Lys Pro Lys Xaa Thr Xaa Met Xaa Xaa Arg Thr Xaa Val
130                 135                 140

Thr Cys Val Val Val Asp Xaa Ser Xaa Xaa Asp Pro Glu Val Xaa Phe
145                 150                 155                 160

Xaa Trp Xaa Val Asp Xaa Val Glu Val His Xaa Ala Xaa Thr Xaa Pro
                165                 170                 175

Arg Glu Glu Gln Xaa Asn Ser Thr Xaa Arg Xaa Val Ser Xaa Leu Xaa
            180                 185                 190

Xaa Xaa His Gln Asp Trp Leu Asn Gly Lys Glu Xaa Lys Cys Xaa Val
        195                 200                 205
```

```
Xaa Xaa Xaa Ala Xaa Pro Ala Pro Ile Glu Lys Thr Ile Ser Lys Xaa
        210                 215                 220

Lys Gly Xaa Pro Xaa Xaa Pro Gln Val Tyr Thr Xaa Pro Pro Xaa Xaa
225                 230                 235                 240

Xaa Xaa Xaa Xaa Lys Xaa Xaa Val Ser Leu Thr Cys Xaa Xaa Xaa Xaa
                245                 250                 255

Phe Xaa Pro Xaa Asp Ile Xaa Val Glu Trp Xaa Xaa Asn Gly Gln Pro
        260                 265                 270

Xaa Xaa Asn Tyr Lys Xaa Thr Xaa Pro Xaa Xaa Asp Xaa Asp Gly Ser
        275                 280                 285

Xaa Phe Xaa Tyr Ser Lys Leu Xaa Val Xaa Lys Ser Xaa Trp Xaa Xaa
290                 295                 300

Gly Asn Xaa Phe Xaa Cys Ser Val Xaa His Glu Xaa Leu His Asn His
305                 310                 315                 320

Xaa Thr Xaa Lys Ser Leu Ser Xaa Ser Pro Gly Lys
                325                 330

<210> SEQ ID NO 39

<400> SEQUENCE: 39

000

<210> SEQ ID NO 40
<211> LENGTH: 214
<212> TYPE: PRT
<213> ORGANISM: Artificial Sequence
<220> FEATURE:
<223> OTHER INFORMATION: Synthetic construct

<400> SEQUENCE: 40

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Lys Asn Gly Ser Pro Arg Leu Leu Ile
            35                  40                  45

Lys His Ala Ser Glu Ser Met Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Thr
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205
```

```
Phe Asn Arg Asn Glu Cys
    210

<210> SEQ ID NO 41
<211> LENGTH: 219
<212> TYPE: PRT
<213> ORGANISM: Artificial Sequence
<220> FEATURE:
<223> OTHER INFORMATION: Synthetic construct

<400> SEQUENCE: 41

Asp Val Val Met Thr Gln Thr Pro Leu Thr Leu Ser Val Thr Ile Gly
1               5                   10                  15

Gln Pro Ala Ser Ile Ser Cys Lys Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val His Tyr Cys Glu Gln Gly
                85                  90                  95

Thr His Phe Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 42
<211> LENGTH: 214
<212> TYPE: PRT
<213> ORGANISM: Artificial Sequence
<220> FEATURE:
<223> OTHER INFORMATION: Synthetic construct

<400> SEQUENCE: 42

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Tyr Leu Leu Ile
        35                  40                  45

Tyr Tyr Thr Ser Ser Leu Gln Ser Gly Val Pro Ser Arg Phe Ser Gly
50                  55                  60

Ser Gly Ser Gly Thr Asp Tyr Ser Leu Thr Ile Ser Asn Leu Glu Ser
```

```
                65                  70                  75                  80
Glu Asp Ile Ala Thr Tyr Tyr Cys Gln Gln Tyr Ser Glu Pro Pro Phe
                    85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
    210

<210> SEQ ID NO 43
<211> LENGTH: 214
<212> TYPE: PRT
<213> ORGANISM: Artificial Sequence
<220> FEATURE:
<223> OTHER INFORMATION: Synthetic construct

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Phe Pro Tyr
                    85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
```

-continued

```
              210

<210> SEQ ID NO 44
<211> LENGTH: 220
<212> TYPE: PRT
<213> ORGANISM: Artificial Sequence
<220> FEATURE:
<223> OTHER INFORMATION: Synthetic construct

<400> SEQUENCE: 44

Asp Ile Val Ile Ser Gln Ser Pro Ser Ser Leu Ala Val Ser Ala Gly
1               5                   10                  15

Glu Lys Val Thr Met Ser Cys Lys Ser Ser Gln Ser Leu Leu Asp Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn His Met Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 45
<211> LENGTH: 214
<212> TYPE: PRT
<213> ORGANISM: Artificial Sequence
<220> FEATURE:
<223> OTHER INFORMATION: Synthetic construct

<400> SEQUENCE: 45

Asp Ile Val Met Thr Gln Ser Gln Lys Phe Met Ser Thr Ser Val Gly
1               5                   10                  15

Asp Arg Val Ser Val Thr Cys Lys Ala Ser Gln Ser Val Gly Thr Asn
            20                  25                  30

Val Ala Trp Phe Gln Gln Thr Pro Gly Gln Ser Leu Lys Val Leu Ile
        35                  40                  45

Tyr Ser Ala Ser Asn Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80
```

```
Glu Asp Leu Ala Glu Tyr Phe Cys Gln Gln Phe Asn Ser Tyr Pro Tyr
                85                  90                  95

Thr Phe Gly Gly Gly Thr Lys Leu Ala Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 46
<211> LENGTH: 214
<212> TYPE: PRT
<213> ORGANISM: Artificial Sequence
<220> FEATURE:
<223> OTHER INFORMATION: Synthetic construct

<400> SEQUENCE: 46

Asp Ile Gln Met Thr Gln Ser Ser Ser Phe Ser Val Ser Leu Gly
1               5                   10                  15

Asp Arg Val Thr Ile Thr Cys Lys Thr Ser Glu Asp Ile Tyr Asn Arg
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
    50                  55                  60

Ser Gly Ser Gly Glu Asp Phe Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210
```

-continued

```
<210> SEQ ID NO 47
<211> LENGTH: 214
<212> TYPE: PRT
<213> ORGANISM: Artificial Sequence
<220> FEATURE:
<223> OTHER INFORMATION: Synthetic construct

<400> SEQUENCE: 47

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
    50                  55                  60

Gly Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Arg Phe Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 48
<211> LENGTH: 234
<212> TYPE: PRT
<213> ORGANISM: Artificial Sequence
<220> FEATURE:
<223> OTHER INFORMATION: Synthetic construct

<400> SEQUENCE: 48

Met Val Ser Thr Ala Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
                20                  25                  30

Val Ser Pro Gly Glu Arg Val Arg Leu Ser Cys Arg Ala Ser Gln Ser
            35                  40                  45

Cys Gly Thr Ser Ile Tyr Trp Tyr Gln Gln Arg Thr Asn Gly Ser Pro
    50                  55                  60

Arg Leu Leu Ile Met Tyr Ala Ser Glu Pro Phe Ser Gly Ile Pro Ser
65                  70                  75                  80

Arg Phe Ser Gly Ser Gly Ser Gly Thr Asp Phe Thr Leu Ser Ile Asn
                85                  90                  95
```

```
Ser Val Glu Ser Glu Asp Ile Ala Asp Tyr Tyr Cys Gln Gln Ser Asn
                100                 105                 110

Ser Trp Pro Trp Thr Phe Gly Gly Thr Arg Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
            210                 215                 220

Ile Val Lys Ser Phe Asn Arg Asn Glu Cys
225                 230

<210> SEQ ID NO 49

<400> SEQUENCE: 49

000

<210> SEQ ID NO 50
<211> LENGTH: 108
<212> TYPE: PRT
<213> ORGANISM: Artificial Sequence
<220> FEATURE:
<223> OTHER INFORMATION: Synthetic construct

<400> SEQUENCE: 50

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Lys Asn Gly Ser Pro Arg Leu Leu Ile
        35                  40                  45

Lys His Ala Ser Glu Ser Met Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Thr
                85                  90                  95

Thr Phe Gly Ala Gly Thr Lys Leu Glu Leu Lys Arg
            100                 105

<210> SEQ ID NO 51
<211> LENGTH: 113
<212> TYPE: PRT
<213> ORGANISM: Artificial Sequence
<220> FEATURE:
<223> OTHER INFORMATION: Synthetic construct

<400> SEQUENCE: 51

Asp Val Val Met Thr Gln Thr Pro Leu Thr Leu Ser Val Thr Ile Gly
1               5                   10                  15
```

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val His Tyr Cys Glu Gln Gly
                85                  90                  95

Thr His Phe Pro Leu Thr Phe Gly Ala Gly Thr Lys Leu Glu Leu Lys
            100                 105                 110

Arg

<210> SEQ ID NO 52
<211> LENGTH: 108
<212> TYPE: PRT
<213> ORGANISM: Artificial Sequence
<220> FEATURE:
<223> OTHER INFORMATION: Synthetic construct

<400> SEQUENCE: 52

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Tyr Leu Leu Ile
        35                  40                  45

Tyr Tyr Thr Ser Ser Leu Gln Ser Gly Val Pro Ser Arg Phe Ser Gly
    50                  55                  60

Ser Gly Ser Gly Thr Asp Tyr Ser Leu Thr Ile Ser Asn Leu Glu Ser
65                  70                  75                  80

Glu Asp Ile Ala Thr Tyr Tyr Cys Gln Gln Tyr Ser Glu Pro Pro Phe
                85                  90                  95

Thr Phe Gly Gly Gly Thr Lys Leu Glu Ile Lys Arg
            100                 105

<210> SEQ ID NO 53
<211> LENGTH: 108
<212> TYPE: PRT
<213> ORGANISM: Artificial Sequence
<220> FEATURE:
<223> OTHER INFORMATION: Synthetic construct

<400> SEQUENCE: 53

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Phe Pro Tyr
                85                  90                  95

-continued

```
Thr Phe Gly Gly Gly Thr Lys Leu Glu Ile Lys Arg
            100                 105

<210> SEQ ID NO 54
<211> LENGTH: 114
<212> TYPE: PRT
<213> ORGANISM: Artificial Sequence
<220> FEATURE:
<223> OTHER INFORMATION: Synthetic construct

<400> SEQUENCE: 54

Asp Ile Val Ile Ser Gln Ser Pro Ser Ser Leu Ala Val Ser Ala Gly
1               5                   10                  15

Glu Lys Val Thr Met Ser Cys Lys Ser Ser Gln Ser Leu Leu Asp Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn His Met Tyr Thr Phe Gly Gly Gly Thr Lys Leu Glu Ile
            100                 105                 110

Lys Arg

<210> SEQ ID NO 55
<211> LENGTH: 108
<212> TYPE: PRT
<213> ORGANISM: Artificial Sequence
<220> FEATURE:
<223> OTHER INFORMATION: Synthetic construct

<400> SEQUENCE: 55

Asp Ile Val Met Thr Gln Ser Gln Lys Phe Met Ser Thr Ser Val Gly
1               5                   10                  15

Asp Arg Val Ser Val Thr Cys Lys Ala Ser Gln Ser Val Gly Thr Asn
            20                  25                  30

Val Ala Trp Phe Gln Gln Thr Pro Gly Gln Ser Leu Lys Val Leu Ile
        35                  40                  45

Tyr Ser Ala Ser Asn Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Phe Asn Ser Tyr Pro Tyr
                85                  90                  95

Thr Phe Gly Gly Gly Thr Lys Leu Ala Ile Lys Arg
            100                 105

<210> SEQ ID NO 56
<211> LENGTH: 108
<212> TYPE: PRT
<213> ORGANISM: Artificial Sequence
<220> FEATURE:
<223> OTHER INFORMATION: Synthetic construct

<400> SEQUENCE: 56

Asp Ile Gln Met Thr Gln Ser Ser Ser Ser Phe Ser Val Ser Leu Gly
1               5                   10                  15
```

-continued

Asp Arg Val Thr Ile Thr Cys Lys Thr Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
 50                  55                  60

Ser Gly Ser Gly Glu Asp Phe Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Ile Lys Arg
            100                 105

<210> SEQ ID NO 57
<211> LENGTH: 108
<212> TYPE: PRT
<213> ORGANISM: Artificial Sequence
<220> FEATURE:
<223> OTHER INFORMATION: Synthetic construct

<400> SEQUENCE: 57

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
 50                  55                  60

Gly Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Arg Phe Pro Leu
                85                  90                  95

Thr Phe Gly Ala Gly Thr Lys Leu Glu Leu Lys Arg
            100                 105

<210> SEQ ID NO 58
<211> LENGTH: 128
<212> TYPE: PRT
<213> ORGANISM: Artificial Sequence
<220> FEATURE:
<223> OTHER INFORMATION: Synthetic construct

<400> SEQUENCE: 58

Met Val Ser Thr Ala Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
            20                  25                  30

Val Ser Pro Gly Glu Arg Val Arg Leu Ser Cys Arg Ala Ser Gln Ser
        35                  40                  45

Cys Gly Thr Ser Ile Tyr Trp Tyr Gln Gln Arg Thr Asn Gly Ser Pro
 50                  55                  60

Arg Leu Leu Ile Met Tyr Ala Ser Glu Pro Phe Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Ser Asn

```
                100             105             110
Ser Trp Pro Trp Thr Phe Gly Gly Gly Thr Arg Leu Glu Ile Lys Arg
        115                 120                 125

<210> SEQ ID NO 59
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(15)
<223> OTHER INFORMATION: Xaa can be any naturally occurring amino acid
<220> FEATURE:
<221> NAME/KEY: misc_feature
<222> LOCATION: (17)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (45)..(52)
<223> OTHER INFORMATION: Xaa can be any naturally occurring amino acid
<220> FEATURE:
<221> NAME/KEY: misc_feature
<222> LOCATION: (55)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (89)..(93)
```

<223> OTHER INFORMATION: Xaa can be any naturally occurring amino acid
<220> FEATURE:
<221> NAME/KEY: misc_feature
<222> LOCATION: (95)..(102)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid

<400> SEQUENCE: 59

Asp Xaa Xaa Xaa Xaa Gln Xaa Xaa Xaa Xaa Xaa Xaa Xaa Xaa Gly
1               5                   10                  15

Xaa Xaa Xaa Xaa Xaa Xaa Cys Xaa Xaa Ser Xaa Xaa Xaa Xaa Xaa
                20                  25                  30

Xaa Xaa Xaa Xaa Xaa Xaa Xaa Xaa Trp Xaa Xaa Gln Xaa Xaa Xaa Xaa
            35                  40                  45

Xaa Xaa Xaa Xaa Leu Ile Xaa Xaa Xaa Xaa Xaa Xaa Xaa Gly Xaa
        50                  55                  60

Pro Xaa Arg Phe Xaa Gly Xaa Gly Ser Gly Xaa Asp Xaa Xaa Leu Xaa
65                  70                  75                  80

Ile Xaa Xaa Xaa Xaa Xaa Glu Asp Xaa Xaa Xaa Xaa Xaa Cys Xaa Xaa
                85                  90                  95

Xaa Xaa Xaa Xaa Xaa Xaa Thr Phe Gly Xaa Gly Thr Xaa Leu Xaa Xaa
            100                 105                 110

Lys Arg

<210> SEQ ID NO 60
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(12)
<223> OTHER INFORMATION: Xaa can be any naturally occurring amino acid

<400> SEQUENCE: 60

Xaa Xaa Xaa Xaa Xaa Xaa Xaa Xaa Xaa Xaa Xaa Xaa
1               5                   10

<210> SEQ ID NO 61
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Can be absent

<400> SEQUENCE: 61

Xaa Xaa Xaa Xaa

```
<210> SEQ ID NO 62
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid

<400> SEQUENCE: 62

Xaa Xaa Xaa Xaa Xaa Xaa Xaa Xaa Thr
1               5

<210> SEQ ID NO 63
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (17)..(21)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (28)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (45)..(52)
<223> OTHER INFORMATION: Xaa can be any naturally occurring amino acid
<220> FEATURE:
<221> NAME/KEY: misc_feature
<222> LOCATION: (55)..(57)
<223> OTHER INFORMATION: Xaa can be any naturally occurring amino acid
<220> FEATURE:
<221> NAME/KEY: misc_feature
<222> LOCATION: (59)..(61)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
```

-continued

```
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (89)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(102)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid

<400> SEQUENCE: 63

Asp Xaa Xaa Xaa Xaa Gln Xaa Xaa Xaa Leu Xaa Xaa Xaa Xaa Gly
1               5                   10                  15

Xaa Xaa Xaa Xaa Xaa Ser Cys Xaa Xaa Ser Gln Xaa Xaa Xaa Xaa
            20                  25                  30

Xaa Xaa Xaa Xaa Xaa Xaa Xaa Xaa Trp Xaa Xaa Gln Xaa Xaa Xaa Xaa
        35                  40                  45

Xaa Xaa Xaa Xaa Leu Ile Xaa Xaa Xaa Ser Xaa Xaa Xaa Ser Gly Xaa
    50                  55                  60

Pro Xaa Arg Phe Xaa Gly Ser Gly Ser Gly Thr Asp Xaa Xaa Leu Xaa
65                  70                  75                  80

Ile Xaa Xaa Xaa Xaa Xaa Glu Asp Xaa Xaa Xaa Xaa Cys Xaa Gln
            85                  90                  95

Xaa Xaa Xaa Xaa Xaa Xaa Thr Phe Gly Xaa Gly Thr Lys Leu Glu Xaa
            100                 105                 110

Lys Arg

<210> SEQ ID NO 64
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
```

```
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(40)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (45)..(52)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (58)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (89)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (96)..(100)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
```

<222> LOCATION: (109)..(109)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid

<400> SEQUENCE: 64

Asp Ile Xaa Xaa Thr Gln Ser Xaa Xaa Xaa Xaa Ser Xaa Xaa Xaa Gly
1               5                   10                  15

Xaa Arg Val Xaa Xaa Cys Xaa Xaa Ser Xaa Xaa Xaa Xaa Xaa Xaa Xaa
            20                  25                  30

Xaa Xaa Xaa Xaa Xaa Xaa Xaa Xaa Trp Xaa Gln Gln Xaa Xaa Xaa Xaa
        35                  40                  45

Xaa Xaa Xaa Xaa Leu Ile Xaa Xaa Ala Xaa Xaa Xaa Xaa Xaa Gly Xaa
    50                  55                  60

Pro Xaa Arg Phe Xaa Gly Xaa Gly Ser Gly Xaa Asp Phe Thr Leu Xaa
65                  70                  75                  80

Ile Xaa Xaa Xaa Xaa Xaa Glu Asp Xaa Xaa Xaa Tyr Xaa Cys Gln Xaa
                85                  90                  95

Xaa Xaa Xaa Xaa Pro Xaa Thr Phe Gly Xaa Gly Thr Xaa Leu Xaa Xaa
                100                 105                 110

Lys Arg

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70
<211> LENGTH: 106
<212> TYPE: PRT
<213> ORGANISM: Artificial Sequence
<220> FEATURE:
<223> OTHER INFORMATION: Synthetic construct

<400> SEQUENCE: 70

Thr Val Ala Ala Pro Ser Val Phe Ile Phe Pro Pro Ser Asp Glu Gln
1               5                   10                  15

```
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 71
<211> LENGTH: 107
<212> TYPE: PRT
<213> ORGANISM: Artificial Sequence
<220> FEATURE:
<223> OTHER INFORMATION: Synthetic construct

<400> SEQUENCE: 71

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 72
<211> LENGTH: 106
<212> TYPE: PRT
<213> ORGANISM: Artificial Sequence
<220> FEATURE:
<223> OTHER INFORMATION: Synthetic construct

<400> SEQUENCE: 72

```
Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```

```
<210> SEQ ID NO 73
<211> LENGTH: 107
<212> TYPE: PRT
<213> ORGANISM: Artificial Sequence
<220> FEATURE:
<223> OTHER INFORMATION: Synthetic construct

<400> SEQUENCE: 73

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 74
<211> LENGTH: 107
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (35)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
```

```
<222> LOCATION: (45)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (92)..(95)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 74

Xaa Xaa Xaa Ala Ala Pro Xaa Val Xaa Ile Phe Pro Pro Ser Xaa Glu
1               5                   10                  15

Gln Leu Xaa Ser Gly Xaa Ala Ser Val Val Cys Xaa Leu Asn Asn Phe
            20                  25                  30

Tyr Pro Xaa Xaa Xaa Xaa Val Xaa Trp Lys Xaa Asp Xaa Xaa Xaa Xaa
        35                  40                  45

Xaa Xaa Xaa Xaa Xaa Ser Xaa Thr Xaa Gln Asp Ser Lys Asp Ser
    50                  55                  60

Thr Tyr Ser Xaa Ser Ser Thr Leu Thr Leu Xaa Lys Xaa Xaa Tyr Glu
65                  70                  75                  80

Xaa His Xaa Xaa Tyr Xaa Cys Glu Xaa Thr His Xaa Xaa Xaa Xaa Ser
            85                  90                  95

Pro Xaa Xaa Lys Ser Phe Asn Arg Xaa Glu Cys
            100                 105

<210> SEQ ID NO 75
<211> LENGTH: 27
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MISC_FEATURE
<222> LOCATION: (7)..(26)
<223> OTHER INFORMATION: amino acids at positions 7-26 may be present or
      absent
<220> FEATURE:
<221> NAME/KEY: MISC_FEATURE
<222> LOCATION: (12)..(26)
<223> OTHER INFORMATION: amino acids at positions 12-26 may be present
      or absent
<220> FEATURE:
<221> NAME/KEY: MISC_FEATURE
<222> LOCATION: (17)..(26)
<223> OTHER INFORMATION: amino acids at positions 17-26 may be present
      or absent
<220> FEATURE:
<221> NAME/KEY: MISC_FEATURE
<222> LOCATION: (22)..(26)
<223> OTHER INFORMATION: amino acids at positions 22-26 may be present
      or absent

<400> SEQUENCE: 75

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25
```